(12) United States Patent
Kiesel et al.

(10) Patent No.: US 8,373,860 B2
(45) Date of Patent: Feb. 12, 2013

(54) TRANSMITTING/REFLECTING EMANATING LIGHT WITH TIME VARIATION

(75) Inventors: Peter Kiesel, Palo Alto, CA (US); Markus Beck, Muenster (DE); Noble M. Johnson, Menlo Park, CA (US); Michael Bassler, Mainz (DE)

(73) Assignee: Palo Alto Research Center Incorporated, Palo Alto, CA (US)

( * ) Notice: Subject to any disclaimer, the term of this patent is extended or adjusted under 35 U.S.C. 154(b) by 395 days.

(21) Appl. No.: 12/762,702

(22) Filed: Apr. 19, 2010

(65) Prior Publication Data

US 2010/0201988 A1    Aug. 12, 2010

Related U.S. Application Data

(63) Continuation-in-part of application No. 12/024,490, filed on Feb. 1, 2008, now Pat. No. 7,701,580.

(51) Int. Cl.
*G01N 21/25* (2006.01)
(52) U.S. Cl. .......................................... 356/417
(58) Field of Classification Search ........... 356/417–418
See application file for complete search history.

(56) References Cited

U.S. PATENT DOCUMENTS

| | | |
|---|---|---|
| 2,708,389 A | 5/1955 | Kavanagh |
| 3,357,230 A | 12/1967 | Topaz |
| 3,797,911 A | 3/1974 | Kogelnik et al. |
| 3,915,573 A | 10/1975 | Knoll et al. |
| 3,958,252 A | 5/1976 | Kashio |
| 3,973,118 A | 8/1976 | LaMontagne |
| 4,081,277 A | 3/1978 | Brault et al. |
| 4,131,899 A | 12/1978 | Christou |
| 4,427,296 A | 1/1984 | Demarest et al. |
| 4,455,089 A | 6/1984 | Yeung et al. |
| 4,514,257 A | 4/1985 | Karlsson et al. |
| 4,573,796 A | 3/1986 | Martin et al. |
| 4,715,672 A | 12/1987 | Duguay et al. |
| 4,764,670 A | 8/1988 | Pace et al. |
| 4,793,705 A | 12/1988 | Shera |
| 4,820,042 A | 4/1989 | Barger |

(Continued)

FOREIGN PATENT DOCUMENTS

| | | |
|---|---|---|
| EP | 0678881 | 11/1995 |
| EP | 1653217 | 5/2006 |

(Continued)

OTHER PUBLICATIONS

Office communication in U.S. Appl. No. 11/698,409, mailed Jun. 11, 2010, 21 pages.

(Continued)

*Primary Examiner* — Kara E Geisel
(74) *Attorney, Agent, or Firm* — Hollingsworth Davis, LLC

(57) ABSTRACT

A filter arrangement can transmit and/or reflect light emanating from a moving object so that the emanating light has time variation, and the time variation can include information about the object, such as its type. For example, emanating light from segments of a path can be transmitted/reflected through positions of a filter assembly, and the transmission functions of the positions can be sufficiently different that time variation occurs in the emanating light between segments. Or emanating light from a segment can be transmitted/reflected through a filter component in which simpler transmission functions are superimposed, so that time variation occurs in the emanating light in accordance with superposition of two simpler non-uniform transmission functions. One or more mask arrangements can be configured to receive the emanating light and in response provide encoded emanating light.

5 Claims, 46 Drawing Sheets

U.S. PATENT DOCUMENTS

| | | |
|---|---|---|
| 4,957,371 A | 9/1990 | Pellicori et al. |
| 4,959,674 A | 9/1990 | Khri-Yakub et al. |
| 4,976,542 A | 12/1990 | Smith |
| 5,080,462 A | 1/1992 | Goto |
| 5,144,498 A | 9/1992 | Vincent |
| 5,151,585 A | 9/1992 | Siebert |
| 5,166,755 A | 11/1992 | Gat |
| 5,243,614 A | 9/1993 | Wakata et al. |
| 5,281,305 A | 1/1994 | Lee et al. |
| 5,305,082 A | 4/1994 | Bret |
| 5,312,535 A | 5/1994 | Waska et al. |
| 5,324,401 A | 6/1994 | Yeung et al. |
| 5,370,842 A | 12/1994 | Miyazaki et al. |
| 5,394,244 A | 2/1995 | Tsai |
| 5,414,508 A | 5/1995 | Takahashi et al. |
| 5,434,667 A | 7/1995 | Hutchins et al. |
| 5,437,840 A | 8/1995 | King et al. |
| 5,445,934 A | 8/1995 | Fodor et al. |
| 5,528,045 A * | 6/1996 | Hoffman et al. ............. 356/418 |
| 5,572,328 A | 11/1996 | Fouckhardt et al. |
| 5,666,195 A | 9/1997 | Shultz et al. |
| 5,674,698 A | 10/1997 | Zarling et al. |
| 5,682,038 A | 10/1997 | Hoffman |
| 5,760,900 A | 6/1998 | Ito et al. |
| 5,777,329 A | 7/1998 | Westphal et al. |
| 5,784,507 A | 7/1998 | Holm-Kennedy et al. |
| 5,792,663 A | 8/1998 | Fry et al. |
| 5,793,485 A | 8/1998 | Gourley |
| 5,798,222 A | 8/1998 | Goix |
| 5,801,831 A | 9/1998 | Sargoytchev |
| 5,825,792 A | 10/1998 | Villeneuve et al. |
| 5,864,641 A | 1/1999 | Murphy et al. |
| 5,872,655 A | 2/1999 | Seddon et al. |
| 5,876,674 A | 3/1999 | Dosoretz et al. |
| 5,880,474 A | 3/1999 | Norton et al. |
| 5,933,233 A | 8/1999 | Gunther |
| 5,945,676 A | 8/1999 | Khalil et al. |
| 5,953,138 A | 9/1999 | Ellis |
| 5,958,122 A | 9/1999 | Fukuda et al. |
| 5,982,478 A | 11/1999 | Ainsworth et al. |
| 5,982,534 A | 11/1999 | Pinkel et al. |
| 6,040,578 A | 3/2000 | Malin et al. |
| 6,049,727 A | 4/2000 | Crothall |
| 6,066,243 A | 5/2000 | Anderson et al. |
| 6,091,502 A | 7/2000 | Weigl et al. |
| 6,108,463 A | 8/2000 | Herron et al. |
| 6,116,718 A | 9/2000 | Peeters et al. |
| 6,122,536 A | 9/2000 | Sun et al. |
| 6,137,117 A | 10/2000 | Feldstein et al. |
| 6,169,604 B1 | 1/2001 | Cao |
| 6,187,592 B1 | 2/2001 | Gourley |
| 6,192,168 B1 | 2/2001 | Feldstein et al. |
| 6,216,022 B1 | 4/2001 | Tyrrell et al. |
| 6,249,346 B1 | 6/2001 | Chen et al. |
| 6,275,628 B1 | 8/2001 | Jones et al. |
| 6,285,504 B1 | 9/2001 | Diemeer |
| 6,295,130 B1 | 9/2001 | Sun et al. |
| 6,306,933 B1 | 10/2001 | Eiger et al. |
| 6,307,623 B1 | 10/2001 | Papuchon et al. |
| 6,310,690 B1 | 10/2001 | Cao et al. |
| 6,353,475 B1 | 3/2002 | Jensen et al. |
| 6,399,405 B1 | 6/2002 | Chen et al. |
| 6,405,073 B1 | 6/2002 | Crowley et al. |
| 6,429,022 B1 | 8/2002 | Kunz et al. |
| 6,438,397 B1 | 8/2002 | Bosquet et al. |
| 6,459,080 B1 | 10/2002 | Yin et al. |
| 6,468,702 B1 | 10/2002 | Yi et al. |
| 6,483,959 B1 | 11/2002 | Singh et al. |
| 6,490,034 B1 | 12/2002 | Woias et al. |
| 6,505,775 B1 | 1/2003 | Gu et al. |
| 6,514,460 B1 | 2/2003 | Fendrock |
| 6,519,037 B2 | 2/2003 | Jung et al. |
| 6,525,308 B1 | 2/2003 | Schmidt-Hattenberger |
| 6,558,945 B1 | 5/2003 | Kao |
| 6,577,780 B2 | 6/2003 | Lockhart |
| 6,580,507 B2 | 6/2003 | Fry et al. |
| 6,603,548 B2 | 8/2003 | Church et al. |
| 6,608,679 B1 | 8/2003 | Chen et al. |
| 6,628,390 B1 | 9/2003 | Johnson |
| 6,630,999 B2 | 10/2003 | Shroder |
| 6,639,679 B2 | 10/2003 | Frojdh |
| 6,665,113 B2 | 12/2003 | Aso et al. |
| 6,694,158 B2 | 2/2004 | Polak |
| 6,697,542 B2 | 2/2004 | Patzman et al. |
| 6,700,664 B1 | 3/2004 | Honda et al. |
| 6,710,871 B1 | 3/2004 | Goix |
| 6,736,484 B2 | 5/2004 | Nakamura |
| 6,742,884 B2 | 6/2004 | Wong et al. |
| 6,755,983 B2 | 6/2004 | Yudasaka |
| 6,759,713 B2 | 7/2004 | Chabinyc et al. |
| 6,768,555 B2 | 7/2004 | Lin et al. |
| 6,781,690 B2 | 8/2004 | Armstrong et al. |
| 6,785,002 B2 | 8/2004 | Zarrabian et al. |
| 6,795,190 B1 | 9/2004 | Paul et al. |
| 6,796,710 B2 | 9/2004 | Yates et al. |
| 6,800,849 B2 | 10/2004 | Staats |
| 6,806,925 B2 | 10/2004 | Ishii et al. |
| 6,809,865 B2 | 10/2004 | Chen |
| 6,815,125 B1 | 11/2004 | Okabe et al. |
| 6,816,257 B2 | 11/2004 | Goix |
| 6,830,856 B2 | 12/2004 | Tsai et al. |
| 6,838,361 B2 | 1/2005 | Takeo |
| 6,839,140 B1 | 1/2005 | O'Keefe et al. |
| 6,856,718 B2 | 2/2005 | Kane et al. |
| 6,865,198 B2 | 3/2005 | Taubman |
| 6,867,420 B2 | 3/2005 | Mathies et al. |
| 6,867,868 B1 | 3/2005 | Barbarossa |
| 6,870,149 B2 | 3/2005 | Berezin |
| 6,872,320 B2 | 3/2005 | Wong et al. |
| 6,872,588 B2 | 3/2005 | Chabinyc et al. |
| 6,887,713 B2 | 5/2005 | Nelson et al. |
| 6,890,050 B2 | 5/2005 | Ready et al. |
| 6,906,792 B2 | 6/2005 | Ortyn et al. |
| 6,934,435 B2 | 8/2005 | Kane |
| 6,952,603 B2 | 10/2005 | Gerber et al. |
| 6,972,261 B2 | 12/2005 | Wong et al. |
| 6,983,176 B2 | 1/2006 | Gardner et al. |
| 7,011,630 B2 | 3/2006 | Desai et al. |
| 7,024,236 B2 | 4/2006 | Ford et al. |
| 7,034,933 B2 | 4/2006 | Walker et al. |
| 7,046,357 B2 | 5/2006 | Weinberger et al. |
| 7,064,836 B2 | 6/2006 | Bechtel et al. |
| 7,106,441 B2 | 9/2006 | Sun et al. |
| 7,130,321 B2 | 10/2006 | Spinelli et al. |
| 7,149,396 B2 | 12/2006 | Schmidt et al. |
| 7,195,465 B2 | 3/2007 | Kane et al. |
| 7,195,797 B2 | 3/2007 | Mearini et al. |
| 7,248,361 B2 | 7/2007 | Kiesel et al. |
| 7,252,360 B2 | 8/2007 | Hersch et al. |
| 7,259,856 B2 | 8/2007 | Kachanov et al. |
| 7,268,868 B2 | 9/2007 | Kiesel et al. |
| 7,274,011 B2 | 9/2007 | Tennant et al. |
| 7,277,569 B2 | 10/2007 | Bruce et al. |
| 7,291,824 B2 | 11/2007 | Kiesel et al. |
| 7,305,112 B2 | 12/2007 | Curry et al. |
| 7,310,153 B2 | 12/2007 | Kiesel et al. |
| 7,315,667 B2 | 1/2008 | Schmidt et al. |
| 7,355,699 B2 | 4/2008 | Gilbert et al. |
| 7,358,476 B2 | 4/2008 | Kiesel et al. |
| 7,365,022 B2 | 4/2008 | Wong et al. |
| 7,386,199 B2 | 6/2008 | Schmidt et al. |
| 7,387,892 B2 | 6/2008 | Kiesel et al. |
| 7,391,517 B2 | 6/2008 | Trebbia et al. |
| 7,420,677 B2 | 9/2008 | Schmidt et al. |
| 7,433,552 B2 | 10/2008 | Kiesel et al. |
| 7,440,101 B2 | 10/2008 | Auer et al. |
| 7,456,953 B2 | 11/2008 | Schmidt et al. |
| 7,466,409 B2 | 12/2008 | Scherer et al. |
| 7,471,399 B2 | 12/2008 | Kiesel et al. |
| 7,479,625 B2 | 1/2009 | Kiesel et al. |
| 7,502,123 B2 | 3/2009 | Schmidt et al. |
| 7,522,786 B2 | 4/2009 | Kiesel et al. |
| 7,529,438 B2 | 5/2009 | Schmidt et al. |
| 7,545,513 B2 | 6/2009 | Kiesel et al. |
| 7,547,904 B2 | 6/2009 | Schmidt et al. |
| 7,554,673 B2 | 6/2009 | Kiesel et al. |
| 7,633,629 B2 | 12/2009 | Kiesel et al. |

| 7,641,777 B2 | 1/2010 | Joseph et al. |
| 7,701,580 B2 | 4/2010 | Bassler et al. |
| 7,763,856 B2 | 7/2010 | Kiesel et al. |
| 7,817,254 B2 | 10/2010 | Hegyi et al. |
| 7,817,276 B2 | 10/2010 | Kiesel et al. |
| 7,879,390 B2 | 2/2011 | Salleo et al. |
| 2002/0155485 A1 | 10/2002 | Kao |
| 2003/0000835 A1 | 1/2003 | Witt et al. |
| 2003/0020915 A1 | 1/2003 | Schueller et al. |
| 2003/0027082 A1 | 2/2003 | Wong et al. |
| 2003/0077660 A1 | 4/2003 | Pien et al. |
| 2003/0081302 A1 | 5/2003 | Kane et al. |
| 2003/0137672 A1 | 7/2003 | Moriya et al. |
| 2003/0161024 A1 | 8/2003 | Zhang et al. |
| 2003/0178555 A1 | 9/2003 | Fang |
| 2003/0179383 A1 | 9/2003 | Chen et al. |
| 2003/0189711 A1 | 10/2003 | Orr et al. |
| 2003/0191377 A1 | 10/2003 | Robinson et al. |
| 2003/0197754 A1 | 10/2003 | Nakamura |
| 2003/0231272 A1 | 12/2003 | Nakamura et al. |
| 2003/0235924 A1 | 12/2003 | Adams et al. |
| 2004/0002225 A1 | 1/2004 | Wong et al. |
| 2004/0031684 A1 | 2/2004 | Witt |
| 2004/0032584 A1 | 2/2004 | Honda et al. |
| 2004/0038386 A1 | 2/2004 | Zesch et al. |
| 2004/0057050 A1 | 3/2004 | Beck et al. |
| 2004/0067167 A1 | 4/2004 | Zhang et al. |
| 2004/0109659 A1 | 6/2004 | Aylward et al. |
| 2004/0110099 A1 | 6/2004 | Kozawa et al. |
| 2004/0132214 A1 | 7/2004 | Lin et al. |
| 2004/0141884 A1 | 7/2004 | Unno et al. |
| 2004/0145738 A1 | 7/2004 | Sun et al. |
| 2004/0175734 A1 | 9/2004 | Stahler et al. |
| 2004/0178523 A1 | 9/2004 | Kim et al. |
| 2004/0223135 A1 | 11/2004 | Ortyn et al. |
| 2004/0223881 A1 | 11/2004 | Cunningham et al. |
| 2004/0228375 A1 | 11/2004 | Ghosh et al. |
| 2004/0248318 A1 | 12/2004 | Weinberger et al. |
| 2004/0253835 A1 | 12/2004 | Kawase |
| 2005/0042615 A1 | 2/2005 | Smith et al. |
| 2005/0068526 A1 | 3/2005 | Avrutsky |
| 2005/0084203 A1 | 4/2005 | Kane |
| 2005/0099624 A1 | 5/2005 | Staehr et al. |
| 2005/0128479 A1 | 6/2005 | Gilbert et al. |
| 2005/0136358 A1 | 6/2005 | Paul et al. |
| 2005/0158868 A1 | 7/2005 | Trebbia et al. |
| 2005/0162648 A1 | 7/2005 | Auer et al. |
| 2005/0162650 A1 | 7/2005 | Yamamoto |
| 2005/0164320 A1 | 7/2005 | McDevitt et al. |
| 2005/0213082 A1 | 9/2005 | DiBernardo et al. |
| 2005/0249605 A1 | 11/2005 | Kane et al. |
| 2005/0255392 A1 | 11/2005 | Tsai et al. |
| 2006/0039070 A1 | 2/2006 | Kiesel et al. |
| 2006/0046312 A1 | 3/2006 | Kiesel et al. |
| 2006/0092413 A1 | 5/2006 | Kiesel et al. |
| 2006/0115749 A1 | 6/2006 | Toyoda |
| 2006/0121555 A1 | 6/2006 | Lean |
| 2006/0138313 A1 | 6/2006 | Tennant et al. |
| 2006/0181710 A1 | 8/2006 | Kachanov et al. |
| 2006/0182659 A1 | 8/2006 | Unlu et al. |
| 2006/0193550 A1 | 8/2006 | Wawro et al. |
| 2006/0203224 A1 | 9/2006 | Sebastian et al. |
| 2006/0268260 A1 | 11/2006 | Liu et al. |
| 2006/0274313 A1 | 12/2006 | Gilbert et al. |
| 2007/0009380 A1 | 1/2007 | Cunningham |
| 2007/0046301 A1 | 3/2007 | Kasapi |
| 2007/0070347 A1 | 3/2007 | Scherer et al. |
| 2007/0076210 A1 | 4/2007 | Kiesel et al. |
| 2007/0116609 A1 | 5/2007 | Baeuerle et al. |
| 2007/0145236 A1 | 6/2007 | Kiesel et al. |
| 2007/0145249 A1 | 6/2007 | Kiesel et al. |
| 2007/0146701 A1 | 6/2007 | Kiesel et al. |
| 2007/0146704 A1 | 6/2007 | Schmidt et al. |
| 2007/0146888 A1 | 6/2007 | Schmidt et al. |
| 2007/0147189 A1 | 6/2007 | Schmidt et al. |
| 2007/0147726 A1 | 6/2007 | Kiesel et al. |
| 2007/0147728 A1 | 6/2007 | Schmidt et al. |
| 2007/0165225 A1 | 7/2007 | Trainer |
| 2007/0172969 A1 | 7/2007 | Wong et al. |
| 2007/0186791 A1 | 8/2007 | Kim et al. |
| 2007/0201025 A1 | 8/2007 | Greenwald |
| 2008/0013092 A1 | 1/2008 | Maltezos et al. |
| 2008/0013877 A1 | 1/2008 | Schmidt et al. |
| 2008/0095985 A1 | 4/2008 | Frey et al. |
| 2008/0181827 A1 | 7/2008 | Bassler et al. |
| 2008/0183418 A1 | 7/2008 | Bassler et al. |
| 2008/0186483 A1 | 8/2008 | Kiesel et al. |
| 2008/0186488 A1 | 8/2008 | Kiesel et al. |
| 2008/0186492 A1 | 8/2008 | Kiesel et al. |
| 2008/0186494 A1 | 8/2008 | Kiesel et al. |
| 2008/0186500 A1 | 8/2008 | Schmidt et al. |
| 2008/0186503 A1 | 8/2008 | Kiesel et al. |
| 2008/0186504 A1 | 8/2008 | Kiesel et al. |
| 2008/0186508 A1 | 8/2008 | Kiesel et al. |
| 2008/0187011 A1 | 8/2008 | Kiesel et al. |
| 2008/0197272 A1 | 8/2008 | Kiesel et al. |
| 2008/0299327 A1 | 12/2008 | Salleo et al. |
| 2009/0016672 A1 | 1/2009 | Schmidt et al. |
| 2009/0016690 A1 | 1/2009 | Schmidt et al. |
| 2009/0190121 A1 | 7/2009 | Hegyi et al. |
| 2009/0194705 A1 | 8/2009 | Bassler et al. |
| 2009/0195773 A1 | 8/2009 | Kiesel et al. |
| 2009/0195852 A1 | 8/2009 | Bassler et al. |
| 2009/0220189 A1 | 9/2009 | Kiesel et al. |
| 2010/0201988 A1 | 8/2010 | Kiesel et al. |

FOREIGN PATENT DOCUMENTS

| EP | 1800752 | 6/2007 |
| EP | 1801562 | 6/2007 |
| EP | 1801564 | 6/2007 |
| EP | 1950552 | 7/2008 |
| WO | WO 95/20144 A1 | 7/1995 |
| WO | WO 99/54730 A1 | 10/1999 |
| WO | WO 00/62050 | 4/2000 |
| WO | WO02/25269 | 3/2002 |
| WO | WO2004/033059 | 4/2004 |
| WO | WO2004/083820 | 9/2004 |
| WO | WO2005/108963 | 11/2005 |
| WO | WO2006/133360 | 12/2006 |
| WO | WO2007069840 | 6/2007 |

OTHER PUBLICATIONS

Bracewell, R.N., The Fourier Transform and Its Applications, 2nd Ed., McGraw-Hill, 1978, Table of Contents and pp. 24-50, 98-126, and 177-188.

Mandy, F., Bese, A., Barnabe, P., Solajic, Z., Bergeron, M., Janossy, G., "A compact, affordable and portable CD4 T-cell machine", Int. Conf. AIDS 2002, Jul. 7-12, 2002, 1 pg.

Janossy, G., Jani, I., Bradley, N. J., Bikoue, A., Pitfield, T., Glencross, D., "Affordable CD4+-T-Cell Counting by Flow Cytometry: CD45 gating for Volumetric Analysis", Clinical and Diagnostic Laboratory Immunology, Sep. 2002, p. 1085-1094.

Adams, M.L., Enzelberger, M., Quake, S., and Scherer, A., "Microfluidic integration on detector arrays for absorption and fluorescence micro-spectrometers", Sensors and Actuators, 2003, pp. 25-31.

Shapiro, H. M., Practical Flow Cytometry, Fourth Edition, Wiley-Liss, 2003, Table of Contents and pp. 49-59, 124-183, 191-197, 345, and 364-366.

Imade, G.E., Badung, B., Pam, S., Agbaji, O., Egah, D., Sagay, A.S., Sankale, J.-L., Kapiga, S., Idoko, J., Kanki, P., "Comparison of a New, Affordable Flow Cytometric Method and the Manual Magnetic Bead Technique for CD4 T-Lymphocyte Counting in a Northern Nigerian Setting", Clinical and Diagnostic Laboratory Imm., Jan. 2005, p. 224-227.

"Flow Cytometry", printed from www.wellscenter.iupui.edu/MMIA on Jan. 29, 2008, 4 pages.

Bassler, M., Schmidt, O., Kiesel, P., and Johnson, N., "Class Identification of Bio-Molecules Based on Multi-Color Native Fluorescence Spectroscopy", International Journal of High Speed Electronics and Systems, vol. 17, No. 4 (2007), p. 671-680.

Hoffman, R. A., "Flow Cytometry: Instrumentation, Applications, Future Trends and Limitations", Springer Series on Fluorescence, vol. 6, 2008, pp. 307-342.

Kiesel, P., Bassler, M., Beck, M., and Johnson, N., "Spatially modulated fluorescence emission from moving particles", Applied Physics Letters, vol. 94, 041107, 2009, 3 pages.

Kiesel, P., Beck, M., Johnson, N., "Abstract Q10.00005: Hand-held flow cytometer for point of care CD4 testing", APA Mar. Meeting 2010, vol. 55, No. 2, 3 pages.

"Optical Chopper—SR540—Optical Chopper System", Stanford Research Systems, on/before Oct. 21, 2008, 2 pages.

Office communication in U.S. Appl. No. 11/702,470, mailed Apr. 25, 2008, 22 pages.

Amendment in U.S. Appl. No. 11/702,470, submitted Jul. 25, 2008, 21 pages.

Office communication in U.S. Appl. No. 11/702,470, mailed Oct. 31, 2008, 22 pages.

Office communication in U.S. Appl. No. 12/023,436, mailed Dec. 23, 2008, 15 pages.

Office communication in U.S. Appl. No. 12/024,490, mailed Dec. 24, 2008, 12 pages.

Office communication in U.S. Appl. No. 12,022,485, mailed Jan. 16, 2009, 18 pages.

Amendment in U.S. Appl. No. 11/702,470, submitted Jan. 30, 2009, 22 pages.

Amendment in U.S. Appl. No. 12/023,436, submitted Mar. 23, 2009, 22 pages.

Amendment in U.S. Appl. No. 12/024,490, submitted Mar. 24, 2009, 32 pages.

Amendment in U.S. Appl. No. 12/022,485, submitted Apr. 15, 2009, 30 pages.

Notice of Allowance and Fee(s) Due in U.S. Appl. No. 11/702,470, mailed Apr. 24, 2009, 15 pages.

Office communication in U.S. Appl. No. 12/023,436, mailed Jun. 12, 2009, 20 pages.

Office communication in U.S. Appl. No. 12/024,490, mailed Jul. 22, 2009, 16 pages.

Office communication in U.S. Appl. No. 12/022,485, mailed Jul. 31, 2009, 5 pages.

Response to Restriction Requirement in U.S. Appl. No. 12/022,485, submitted Aug. 27, 2009, 20 pages.

Amendment in U.S. Appl. No. 12/023,436, submitted Sep. 3, 2009, 29 pages.

Amendment After Final Rejection in U.S. Appl. No. 12/024,490, submitted Sep. 22, 2009, 28 pages.

Office communication in U.S. Appl. No. 12/024,490, mailed November 2, 2009, 14 pages.

Office communication in U.S. Appl. No. 11/698,409, mailed Nov. 17, 2009, 18 pages.

Office communication in U.S. Appl. No. 12/025,394, mailed Jan. 22, 2010, 19 pages.

Office communication in U.S. Appl. No. 12/023,436, mailed Feb. 5, 2010, 16 pages.

Amendment in U.S. Appl. No. 12/023,436, submitted Mar. 23, 2010, 24 pages.

Office communication in U.S. Appl. No. 12/023,436, mailed Apr. 16, 2010, 8 pages.

Amendment in U.S. Appl. No. 12/025,394, submitted Apr. 22, 2010, 17 pages.

Amendment in U.S. Appl. No. 11/698,409, submitted May 17, 2010, 16 pages.

"4-Channel Optical Transceiver Applying 3-Dimensional Polymeric Waveguide", FIND, vol. 24, No. 4, 2006, pp. 1-5.

Adams et al., "Microfluidic Integration on Detector Arrays for Absorption and Fluorescence Micro-spectrometer", Sensors and Actuators, 2003, pp. 25-31.

Agilent Technologies, "Agilent 83453B High-Resolution Spectrometer—Technical Specifications", Feb. 2005, pp. 1-8.

Agilent Technologies "Developing Technology: HPLC-Chip/MS", May 25, 2011, 2 pages.

Bassler et al., "Class Identification of Bio-Molecules Based on Multicolor Native Fluorescence Spectroscopy", Optics, East 2006, Session SA201, 2006. (abstract only).

Becker et al., "Polymer Microfabrication Methods for Microfluidic Analytical Applications", Electrophoresis, vol. 21, 2000, pp. 12-26. (abstract only).

Bernini et al., "Silicon Micromachined Hollow Optical Waveguides for Sensing applications", IEEE Journal on Selected Topics in Quantum Electronics, vol. 8, No. 1, Jan./Feb. 2002, pp. 106-110. (abstract only).

Bhatta et al., "Rapid Identification of Microorganisms by Intrinsic Fluorescence", Proc. of SPIE, vol. 5699, 2005, pp. 9-18.

Cheung et al., "Impedance Spectroscopy Flow Cytometry: On-Chip Label-Free Cell Differentiation", Cytometry Part A, vol. 65A, 2005, pp. 124-132.

Cunningham et al., "Label-Free Assays on the Bind System", Journal of Biomolecular Screening, vol. 9, No. 6, 2004, pp. 481-490.

Devasenathipathy et al., "3 Electrokinetic Flow Diagnostics", in Breuer K.S. Ed. Micro-and Nano-Scale Diagnostic Techniques, Springer Verlag, New York, 2003, pp. 121-166.

Fuhr, Measuring with Light, Sensors Magazine Online, May 2000, 11 pages.

Fuji-Keizai USA, "Biosensor Market, R&D and Commercial Implication", 2004, 5 pages.

Henry et al., "Wavelength Response of Thin-Film Optical Position-Sensitive Detectors", J. Opt. A: Pure Appl. Opt., Vole. 4, 2002, pp. 527-534. (abstract only).

Holmes et al., "Label-Free Differential Leukocyte Counts Using a Microfabricated, Single-Cell Impedance Spectrometer", Sensors, 2007 IEEE, pp. 1452-1455. (abstract only).

Johnson et al., "Introductions to Photonic Crystals: Bloch's Theorem, Band Diagrams, and Gaps (But No Defects)", Feb. 3, 2003, 16 pages.

Johnson, "Photonic Crystals: Periodic Surprises in Electromagnetism", printed from ab-initio.mit.edu on Oct. 5, 2006, 29 pages.

Jones et al., "Dielectrophoretic Liquid Actuation Nanodroplet Formation", Journal of Applied Physics, vol. 89, No. 2, 2001, pp. 1441-1448. (abstract only).

Kalvaram et al., "Precision moulding techniques for optical waveguide devices", SPIE, vol. 3135, 1997, pp. 2-11. (abstract only).

Kiesel et al., "Spatially Modulated Emission Advances Point-of-Care Diagnostics", Laser Focus World, Nov. 2010, pp. 47-50.

Konsziela, "Accurately Measure Laser Spectral Characteristics", 2006, 5 pages.

Kim et al., "Polymer-Planar-Lightwave-Circuit-Type Variable Optical Attenuator Fabricated by Hot Embossing Process" ETRI Journal, vol. 27, No. 1, Feb. 2004, pp. 122-125.

Law et al., "Low-Voltage Superlattice Asymmetric Fabry-Perot Reflection Modulator", IEEE Phot. Tech. Lett, vol. 3, No. 4, Apr. 1991, pp. 324-326. (abstract only).

Liang et al., "Refractive Index Measurement of Single Living Cell Using a Biophotonic Chip for Cancer Diagnosis Applications", 9$^{th}$ International Conference on Miniaturized Systems for Chemistry and Life Sciences, Oct. 2005, pp. 464-466.

Liu et al., "Nanowell Surface Enhanced Raman Scattering Arrays Fabricated by Soft-Lithography for Label-Free Biomolecular Detections in Integrated Microfluidics", Applied Physics Letters, vol. 87, 2005, pp. 1-3.

McNichols et al., "Optical Glucose Sensing in Biological Fluids: An Overview", Journal of Biomedical Optics, vol. 5, No. 1, Jan. 2000, pp. 5-16. (abstract only).

Schaefer et al., "Accuracy of Position Detection Using a Position-Sensitive Detector", IEEE Transactions on Instrumentation and Measurement, vol. 47, No. 4, Aug. 1998, pp. 914-919. (abstract only).

Schmidt et al., "Guiding Light in Fluids", applied Physics Letters, vol. 88, 2006, pp. 151109-1-1151109-14.

Schmidt et al., "Enhanced light-target interaction using a novel anti-resonant waveguide concept", SPIE Proc. 6094, 2006, pp. 80-89.

Schmidt et al., "Fluorescence Spectrometer-on-a-fluidic-chip", Lab Chop, 2007. (abstract only).

Seamer et al., "Sheath Fluid control to Permit Stable Flow in Rapid Mix Flow Cytometry", Cytometry, vol. 5699, 2005, pp. 75-79.

Sims et al., "Analysis of Single Mammalian Cells On-Chip", Lab Chip., vol. 7, Issue 4, Apr. 2007, pp. 423-440. (Abstract only).

Singh et al., "Analysis of cellular Structure by Light Scattering Measurements in a New Cytometer Design Based on a Liquid-Core Waveguide", IEEE Proceedings Nanobiotechnology, vol. 151, No. 1, Feb. 2004, pp. 10-16. (abstract only).

Sivaprakasam et al., "Multiple UV Wavelength Excitation and Fluorescence of Bioaerosols", 2$^{nd}$ Joint conference on Point Detections, Williamsburg, VA 2004, 10 pages.

Spear et al., "Low noise position sensitive detector for optical probe beam deflection measurements", Rev. Sci. Instrum., vol. 67, No. 7, Jul. 1996, pp. 2481-2484. (abstract only).

SRU Biosystems, Inc., "Bind Biosensor TM Technology", Apr. 3, 2004 excerpt, 1 page.

Udd, "Good Sense", SPIE's OEMagazine, Aug. 2002, pp. 27-29.

Vogel, "Tunable Liquid Crystal Fabry-Perot Filters", Institute for Electrical and Optical Communication Engineering, University of Stuttgart, 2002, 10 pages. (abstract only).

Vollmer et al., "Multiplexed DNA Quantification by Spectroscopic Shift of Two Microsphere Cavities", Biophysical Journal, vol. 85, Sep. 2005, pp. 1974-1979.

Weismann et al., "Singlemode polymer waveguides for optical backplanes", Electronics Letters, vol. 32, No. 25, Dec. 5, 1996, pp. 2329-2330. (abstract only).

File History for U.S. Appl. No. 12/023,436.

File History for U.S. Appl. No. 12/025,394.

File History for U.S. Appl. No. 12/024,490.

File History for U.S. Appl. No. 11/698,409.

File History for U.S. Appl. No. 11/702,470.

File History for U.S. Appl. No. 12/022,485.

File History for U.S. Appl. No. 13/113,021.

File History for EP Application No. 09151643.5 as retrieved from the European Patent Office electronic file system on Oct. 24, 2012, 119 pages.

* cited by examiner $|X_1 - X_2| \leq 10\mu m$ $|Y_1 - Y_2| \leq 10\mu m$ $|Z_1 - Z_2| \leq 10\mu m$

TRANSMITTING/REFLECTING EMANATING LIGHT WITH TIME VARIATION

CLAIM FOR PRIORITY

Pursuant to 37 C.F.R. §§1.52(b)(2) and 1.78, this application claims priority as a Continuation-in-Part Application under 35 U.S.C. §120 to U.S. Non-provisional patent application Ser. No. 12/024,490, filed Feb. 1, 2008, now U.S. Pat. No. 7,701,580, the entire contents of which are expressly incorporated herein by reference.

CROSS REFERENCE TO RELATED APPLICATIONS

The following patent documents, each of which is hereby incorporated by reference in its entirety, might be regarded as related to this application: U.S. Pat. Nos. 7,701,580; 7,365,022; 7,547,904; 7,420,677; 7,358,476; 7,433,552; 7,386,199; 7,502,123; 7,471,399; 7,817,276; 7,545,513; 7,554,673; 7,522,811; 7,529,438; 7,817,254; and 7,763,856, and Patent Application Publications US 2008/0183418; US 2008/0181827; and US 2008/0299327.

BACKGROUND OF THE INVENTION

The present invention relates generally to techniques that transmit and/or reflect light emanating from objects. More specifically, techniques can use filter arrangements to transmit and/or reflect such light with time variation, such as where the objects are moving relative to the filter arrangements.

Various techniques have been proposed for using light emanating from objects. For example, U.S. Pat. No. 7,358,476 describes a fluidic structure with a channel along which is a series of sensing components to obtain information about objects traveling within the channel, such as droplets or other objects carried by fluid. A sensing component includes a set of cells that photosense a range of photon energies that emanate from objects. A processor can receive information about objects from the sensing components and use it to obtain spectral information. Similar techniques are described, for example, in U.S. Pat. Nos. 7,547,904, 7,420,677, and 7,386,199.

Also, various flow cytometry techniques have been proposed.

It would be advantageous to have improved techniques for using light emanating from objects, including improved techniques for transmitting and/or reflecting such light with time variation.

SUMMARY OF THE INVENTION

The invention provides various exemplary embodiments, including methods and apparatus. In general, the embodiments involve transmitting and/or reflecting emanating light through filter arrangements to obtain time variation.

All the above described disadvantages are overcome and a number of advantages are realized by a first aspect that relates to an article of manufacture comprising: a fluid-engaging structure, wherein the fluid-engaging structure includes (a) a channel that in use can contain fluid and through which objects can move; (b) one or more bounding parts that bound the channel, and wherein at least one of the one or more bounding parts include one or more light transmissive portions, wherein at least one of the one or more light transmissive portions is configured to receive excitation light and provide the received excitation light, and wherein excitation light enters the channel and interacts with an object resulting in emanating light; and (c) one or more mask arrangements configured to receive at least part of the emanating light and in response, provide encoded emanating light, wherein the one or more mask arrangements and the channel are further configured so that the encoded emanating light includes time variation resulting from relative movement between the one or more mask arrangements and the object, the time variation including information about the object.

According to the first aspect, the a method of using the article of manufacture is provided comprising causing an object to move through the channel in a fluid; causing the excitation light to enter the channel through the one or more light transmissive portions and interact with the object, resulting in the emanating light from the object; receiving the emanating light at a first of the one or more mask arrangements; and providing the encoded emanating light with the time variation including the information about the object in response to the received emanating light.

Still further according to the first aspect, the fluid is water and the object includes at least one of e. coli, giardia, cryptosporidium, and bacillus endospore, and the fluid is human blood and the object includes at least one of CD4 lymphocytes and CD4 monocytes.

According to the first aspect, the method further comprises receiving the encoded emanating light at a photosensitive surface of a large area photosensor; and providing an electrical signal by the large area photosensor, in response to the received encoded emanating light, the electrical signal indicating one or more sensed time-varying waveforms, and wherein at least one of the one or more sensed time-varying waveforms indicating the information about the object. According to the first aspect, a host structure includes the large area photosensor, the host structure being separate from and useable with the fluid-engaging structure, the method further comprising operating circuitry in the host structure to respond to the electrical signal by providing data indicating the information about the object.

According to the first aspect, the host structure includes one of a handheld device, the handheld device configured to monitor discrete samples of fluid and objects, and an in-line device, the in-line device configured to substantially continuously monitor the fluid and objects, and wherein the fluid-engaging structure further comprises: a first of the one or more mask arrangements configured to receive at least part of the emanating light and in response provide encoded emanating light to received emanating light, and is located on a first portion of the bounding parts; one or more mirrors, at least one of the one or more minors configured to substantially reflect the excitation light through the one or more light transmissive portions; and an internal reflecting surface, wherein the internal reflecting surface is configured to re-transmit the reflected excitation light into the channel with the fluid and objects, and wherein the article of manufacturing is configured for use with a host structure, and wherein the host structure includes: at least one excitation light source; a filter configured to receive and filter the encoded emanating light; and a photo-sensor configured to receive the filtered encoded emanating light and detect time variation resulting from relative movement between the one or more mask arrangements and the objects, the time variation including information about the objects, and wherein the photo-sensor is further configured to provide an electrical signal indicating one or more sensed time-varying waveforms.

Still further according to the first aspect, the article of manufacture is configured to be disposable, the excitation light source includes one of a light emitting diode and laser diode, and the photo sensor is one of a large area photo sensor and a PIN diode. According to the first aspect, the article of manufacturing is configured for use with a host structure, and wherein the host structure comprises: at least one excitation light source; at least one filter configured to receive and filter the encoded emanating light; and a photo-sensor configured to receive the filtered encoded emanating light and detect time variation resulting from relative movement between the one or more mask arrangements and the objects, the time variation including information about the objects, and wherein the photo-sensor and the at least one filter configured to receive and filter the encoded emanating light are located on a first exterior side of the one or more bounding parts of the fluid-engaging structure, and the at least one excitation light source is located substantially directly opposite that of the photo-sensor and the at least one filter configured to receive and filter the encoded emanating light.

According to the first aspect, the article of manufacturing is configured for use with a host structure, and wherein the host structure comprises: at least one excitation light source; at least one filter configured to receive and filter the encoded emanating light; and a photo-sensor configured to receive the filtered encoded emanating light and detect time variation resulting from relative movement between the one or more mask arrangements and the objects, the time variation including information about the objects, and wherein the photo-sensor and the at least one filter configured to receive and filter the encoded emanating light are located on a first exterior side of the one or more bounding parts of the fluid-engaging structure, and the at least one excitation light source is located substantially adjacent to that of the photo-sensor and the at least one filter configured to receive and filter the encoded emanating light.

Still further according to the first aspect, the fluid-engaging structure further comprises: at least two mirrors, wherein a first mirror is configured to substantially reflect first excitation light from a first excitation light source through the one or more light transmissive portions, and a second mirror is configured to substantially reflect second excitation light from a second excitation light source through the one or more light transmissive portions; and an internal reflecting surface, wherein the internal reflecting surface is configured to re-transmit the first reflected excitation light into the channel with the fluid and objects, and the internal reflecting surface is configured to re-transmit the second reflected excitation light into the channel with the fluid and objects, and wherein the re-transmitted first and second excitation light interacts with the object resulting in a combined emanating light; and a first of the one or more mask arrangements is located on a first portion of the bounding parts, wherein, the first of the one or more mask arrangements is configured to receive at least part of the combined emanating light at a first range of photon energies and, in response, provide encoded combined emanating light at the first range of photon energies.

According to the first aspect, the article of manufacturing further comprises a host structure, the host structure including the first excitation light source configured to transmit the first excitation light; the second excitation light source configured to transmit the second excitation light; a first photo-sensor; a second photo-sensor; a second of the one or more mask arrangements, and wherein the second of the one or more mask arrangements is configured to receive at least part of the combined emanating light and, in response, provide encoded combined emanating light at a second range of photon energies; a first filter located substantially adjacent to the first photo-sensor, wherein the first filter is configured to pass a first portion of the encoded combined emanating light that corresponds to the first range of photon energies to the first photo-sensor; and a second filter located substantially adjacent to the second photo-sensor, wherein the second filter is configured to pass a second portion of the encoded combined emanating light that corresponds to the second range of photon energies to the second photo-sensor.

According to the first aspect, the first photo-sensor is configured to receive the filtered first portion of the encoded combined emanating light that corresponds to the first range of photon energies and detect time variation resulting from relative movement between the one or more mask arrangements and the objects, the time variation including information about the objects, and wherein the first photo-sensor is further configured to provide a first set of electrical signals indicating one or more sensed time-varying waveforms to host structure circuitry, and the second photo-sensor is configured to receive the filtered second portion of the encoded combined emanating light that corresponds to the second range of photon energies and detect time variation resulting from relative movement between the one or more mask arrangements and the objects, the time variation including information about the objects, and wherein the second photo-sensor is further configured to provide a second set of electrical signals indicating one or more sensed time-varying waveforms to host circuitry.

According to the first aspect, the first and second excitation light sources includes one of a laser diode and light emitting diode, and the host structure further comprises: an optical device for re-directing encoded combined emanating light at either a first range of photon energies or at a second range of photon energies.

According to the first aspect, the fluid-engaging structure further comprises: a first receptacle for accepting the fluid, and the objects within the fluid; a second receptacle for accepting the fluid and the objects within the fluid following passage through the channel; and a vacuum spring-loaded syringe configured to compel movement of the fluid and the objects through the channel, and to energize an excitation light source upon release of the spring.

According to the first aspect, the fluid-engaging structure comprises: a first of the one or more mask arrangements is configured to receive at least part of the emanating light and, in response, provide color-dependent encoded emanating light and is located on a first portion of the bounding parts, and wherein the fluid engaging structure is configured for use with a host structure, and wherein the host structure includes: at least one excitation light source; a filter configured to receive and filter the color-dependent encoded emanating light; and a photo-sensor configured to receive the filtered color-dependent encoded emanating light and detect time variation resulting from relative movement between the one or more mask arrangements and the objects, the time variation including information about the objects, and wherein the photo-sensor is further configured to provide an electrical signal indicating one or more sensed time-varying waveforms.

Still further according to the first aspect, the fluid-engaging structure comprises: a first of the one or more mask arrangements configured to receive at least part of the emanating light and, in response, provide first color-dependent encoded emanating light and is located on a first portion of the bounding parts; a second of the one or more mask arrangements configured to receive at least part of the emanating light and, in response, provide second color-dependent encoded emanating light and is located on a second portion of the bounding parts, and wherein the fluid engaging structure is configured for use with a host structure, and wherein the host structure includes: a first excitation light source; a second excitation light source; a first filter configured to receive and filter the first color-dependent encoded emanating light, the first filter located substantially adjacent to the first of the one or more mask arrangements; a second filter configured to receive and filter the second color-dependent encoded emanating light, the second filter located substantially adjacent to the second of the one or more mask arrangements; a first photo-sensor located substantially adjacent to the first filter, and wherein the first photo-sensor is configured to receive the first filtered color-dependent encoded emanating light and detect time variation resulting from relative movement between the one or more mask arrangements and the objects, the time variation including information about the objects, and wherein the first photo-sensor is further configured to provide a first electrical signal indicating one or more sensed time-varying waveforms; and a second photo-sensor located substantially adjacent to the second filter, and wherein the second photo-sensor is configured to receive the second filtered color-dependent encoded emanating light and detect time variation resulting from relative movement between the one or more mask arrangements and the objects, the time variation including information about the objects, and wherein the second photo-sensor is further configured to provide a second electrical signal indicating one or more sensed time-varying waveforms.

A second aspect that overcomes all of the above described disadvantages and provides a number of advantages includes an article of manufacture comprising: a host structure, wherein the host structure includes (a) at least one excitation light source; (b) one or more support parts structured to support a fluid-engaging structure on the host structure, wherein the fluid-engaging structure includes a channel that in use can contain fluid and through which objects can move; one or more bounding parts that bound the channel, and wherein at least one of the one or more bounding parts include one or more light transmissive portions, wherein at least one of the one or more light transmissive portions is configured to receive excitation light and provide the received excitation light, and wherein excitation light enters the channel and interacts with an object resulting in emanating light; and one or more mask arrangements configured to receive at least part of the emanating light and, in response, provide encoded emanating light, and wherein the one or more mask arrangements and the channel are further configured so that the encoded emanating light includes time variation resulting from relative movement between the one or more mask arrangements and the object, the time variation including information about the object; (c) at least one filter configured to receive and filter the encoded emanating light; (d) at least one photo-sensor configured to receive the filtered encoded emanating light and detect time variation resulting from relative movement between the one or more mask arrangements and the objects, the time variation including information about the objects, and wherein the photo-sensor is further configured to provide a first electrical signal indicating one or more sensed time-varying waveforms; and (e) circuitry configured to receive the first electrical signals and which is further configured to provide second electrical signals in response to the first electrical signals resulting from photo-sensing of the encoded emanating light, and wherein the second electrical signals indicate the information about the objects.

According to the second aspect, the host structure is configured for use as a point-of-care apparatus, the excitation light source includes one of a light emitting diode and laser diode, the at least one photo-sensor is one of a large area photo sensor and a PIN diode, and the photo-sensor and the at least one filter configured to receive and filter the encoded emanating light are located on a first exterior side of the one or more bounding parts of the fluid-engaging structure, and the at least one excitation light source is located substantially directly opposite that of the photo-sensor and the at least one filter configured to receive and filter the encoded emanating light.

Still further according to the second aspect, the at least one photo-sensor and the at least one filter configured to receive and filter the encoded emanating light are located on a first exterior side of the one or more bounding parts of the fluid-engaging structure, and the at least one excitation light source is located substantially adjacent to that of the photo-sensor and the at least one filter configured to receive and filter the encoded emanating light, and the host structure further comprises: a first excitation light source configured to transmit first excitation light; a second excitation light source configured to transmit the second excitation light, and wherein the fluid-engaging structure is configured to provide combined emanating light resulting from interaction between the first excitation light and the objects, and the second excitation light and the objects, and wherein the fluid-engaging structure further includes a first of the one or more mask arrangements that is located on a first portion of the bounding parts, and wherein, the first of the one or more mask arrangements is configured to receive at least part of the combined emanating light at a first range of photon energies and, in response, provide encoded combined emanating light, the host structure further comprising; a first photo-sensor; a second photo-sensor; a second of the one or more mask arrangements, and wherein the second of the one or more mask arrangements is configured to receive at least part of the combined emanating light and, in response, provide encoded combined emanating light at a second range of photon energies; a first filter located substantially adjacent to the first photo-sensor, wherein the first filter is configured to pass a first portion of the encoded combined emanating light that corresponds to the first range of photon energies to the first photo-sensor; and a second filter located substantially adjacent to the second photo-sensor, wherein the second filter is configured to pass a second portion of the encoded combined emanating light that corresponds to the second range of photon energies to the second photo-sensor.

According to the second aspect, the first photo-sensor is configured to receive the filtered first portion of the encoded combined emanating light that corresponds to the first range of photon energies and detect time variation resulting from relative movement between the one or more mask arrangements and the objects, the time variation including information about the objects, and wherein the first photo-sensor is further configured to provide a first set of electrical signals indicating one or more sensed time-varying waveforms to host structure circuitry, and the second photo-sensor is configured to receive the filtered second portion of the encoded combined emanating light that corresponds to the second range of photon energies and detect time variation resulting from relative movement between the one or more mask arrangements and the objects, the time variation including information about the objects, and wherein the second photo-sensor is further configured to provide a second set of electrical signals indicating one or more sensed time-varying waveforms to host circuitry.

Still further according to the second aspect, the first and second excitation light sources includes one of a laser diode and light emitting diode, and the host structure further comprises: an optical device for re-directing encoded combined emanating light at either a first range of photon energies or at a second range of photon energies. Still further according to the second aspect, the filter is further configured to receive and filter color-dependent encoded emanating light, and wherein the photo-sensor is further configured to receive the filtered color-dependent encoded emanating light and detect time variation resulting from relative movement between the one or more mask arrangements and the objects, the time variation including information about the objects, and wherein the photo-sensor is further configured to provide an electrical signal indicating one or more sensed time-varying waveforms.

According to the second aspect, the host structure comprises: a first excitation light source; a second excitation light source; a first filter configured to receive and filter first color-dependent encoded emanating light provided by the fluid-engaging structure, the first filter located substantially adjacent to a first of the one or more mask arrangements located on the fluid-engaging structure; a second filter configured to receive and filter second color-dependent encoded emanating light provided by the fluid engaging structure, the second filter located substantially adjacent to a second of the one or more mask arrangements located on the fluid-engaging structure; a first photo-sensor located substantially adjacent to the first filter, and wherein the first photo-sensor is configured to receive the first filtered color-dependent encoded emanating light and detect time variation resulting from relative movement between the one or more mask arrangements and the objects, the time variation including information about the objects, and wherein the first photo-sensor is further configured to provide a first electrical signal indicating one or more sensed time-varying waveforms; and a second photo-sensor located substantially adjacent to the second filter, and wherein the second photo-sensor is configured to receive the second filtered color-dependent encoded emanating light and detect time variation resulting from relative movement between the one or more mask arrangements and the objects, the time variation including information about the objects, and wherein the second photo-sensor is further configured to provide a third electrical signal indicating one or more sensed time-varying waveforms, and wherein the circuitry is further configured to receive the first electrical signals and the third electrical signals, and which is further configured to provide fourth electrical signals in response to the first and third electrical signals resulting from photosensing of the encoded emanating light, and wherein the fourth electrical signals indicate the information about the objects.

According to the second aspect, the host structure further comprises: a slot, wherein the slot is configured to receive the fluid-engaging structure, to provide a substantially lossless light-interface between a first excitation light source and the fluid engaging structure, and to further provide a substantially lossless light-interface between a first photosensor and the fluid engaging structure.

Still further according to the second aspect, the host structure further comprises: a second photosensor; and a second excitation light source, and wherein the slot is configured to provide a substantially lossless light-interface between the second excitation light source and the fluid engaging structure, and to further provide a substantially lossless light-interface between the second photosensor and the fluid engaging structure, and the host structure further comprises: an interface board configured to accept data entries by a user of the article of manufacture; and a display, wherein the display is configured to display data about the fluid to the user of the article of manufacture, and wherein the host structure is further configured to be one of either a hand-held unit, or an in-line unit.

According to the second aspect, a method of using the article of manufacture is provided comprising: receiving the fluid-engaging structure, wherein the fluid engaging structure includes the fluid and objects; determining information about the objects within the fluid; and displaying the information about the objects within the fluid to the user of the article of manufacture. According to the second aspect, the step of receiving the fluid-engaging structure comprises: locating the fluid-engaging structure in a slot in the host structure, wherein the slot is configured to secure temporarily the fluid-engaging structure to the host structure, provide a first light-interface between a first excitation light source on the host structure and the fluid engaging structure, and further provide a second light-interface between a first photosensor on the host structure and the fluid engaging structure, and wherein substantially no fluid in the fluid-engaging structure contacts the host structure. According to the second aspect, the step of determining information about the objects within the fluid comprises: receiving filtered encoded emanating light from the fluid-engaging structure by a photo-sensor, wherein the encoded emanating light includes time variation resulting from relative movement between the one or more mask arrangements of the fluid-engaging structure and the object, the time variation including information about the object; detecting time variation resulting from relative movement between the one or more mask arrangements and the objects by the photo-sensor; providing a first electrical signal from the photo-sensor that indicates one or more sensed time-varying waveforms; and receiving by host circuitry the first electrical signals; and providing second electrical signals in response to the first electrical signals, wherein the second electrical signals indicate the information about the objects, and the information includes at least one of a type of the object, a quantity of the objects, a velocity of the objects, and a color of the objects.

A third aspect that overcomes all of the above described disadvantages and provides a number of advantages includes an article of manufacture comprising: a host structure, wherein the host structure includes a first excitation light source; a second excitation light source; one or more support parts structured to support a fluid-engaging structure on the host structure, wherein the fluid-engaging structure includes a channel that in use can contain fluid and through which objects can move; one or more bounding parts that bound the channel, and wherein at least one of the one or more bounding parts include one or more light transmissive portions, wherein at least one of the one or more light transmissive portions is configured to receive excitation light and provide the received excitation light, and wherein excitation light enters the channel and interacts with an object resulting in emanating light; a first mask arrangement configured to receive at least part of the emanating light and, in response, provide encoded emanating light, and wherein the first filter arrangement and channel are further configured so that the encoded emanating light includes time variation resulting from relative movement between the first mask arrangement and the object, the time variation including information about the object; a first filter configured to receive and filter the encoded emanating light from the first mask arrangement; and a first photo-sensor configured to receive the filtered encoded emanating light from the first filter and detect time variation resulting from relative movement between the one or more mask arrangements and the object, the time variation including information about the objects, and wherein the first photo-sensor is further configured to provide a first electrical signal indicating one or more sensed time-varying waveforms; a first electrical interconnection; and a second mask arrangement configured to receive at least part of the emanating light, and, in response, provide encoded emanating light, and wherein the second mask arrangement and channel are further configured so that the encoded emanating light includes time variation resulting from relative movement between the second mask arrangement and the object, the time variation including information about the object; a second filter configured to receive and filter the encoded emanating light from the second filter arrangement; and a second photo-sensor configured to receive the filtered encoded emanating light from the second filter and detect time variation resulting from relative movement between the second mask arrangement and the object, the time variation including information about the object, and wherein the second photo-sensor is further configured to provide a third electrical signal indicating one or more sensed time-varying waveforms; and circuitry configured to receive the first and third electrical signals and which is further configured to provide fourth electrical signals in response to the first and third electrical signals resulting from photosensing of the encoded emanating light, and wherein the fourth electrical signals indicate the information about the object.

According to the third aspect, the host structure is configured for use as a point-of-care apparatus, the excitation light source includes one of a light emitting diode and laser diode, and the at least one photo-sensor is one of a large area photo sensor and a PIN diode.

These and other features and advantages of exemplary embodiments of the invention are described below with reference to the accompanying drawings.

DETAILED DESCRIPTION

Figure 1:
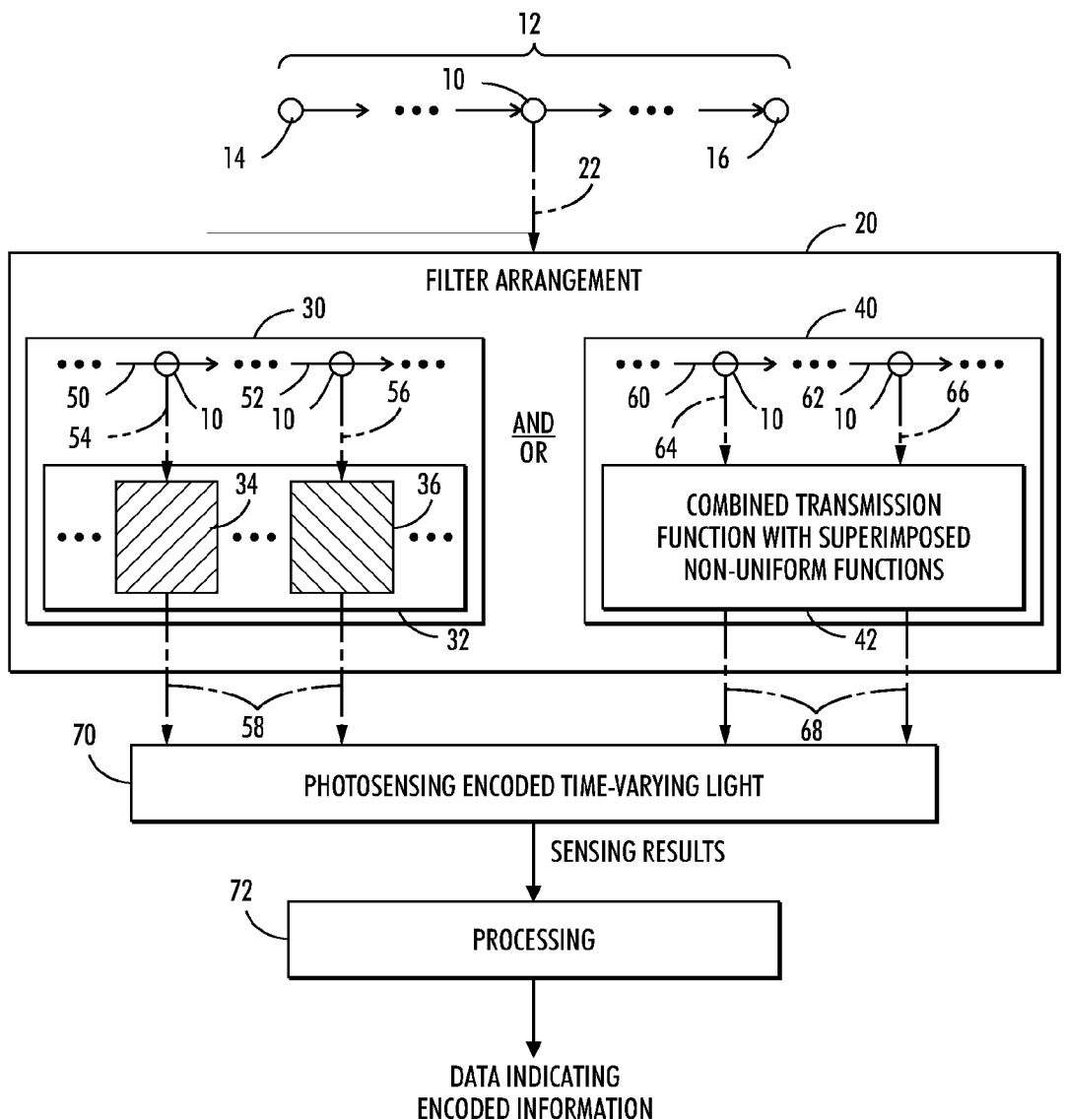
FIG. 1 is a schematic diagram showing features of techniques in which a filter arrangement transmits and/or reflects light emanating from an object with time variation.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. Light that can include information is sometimes referred to herein as an "optical signal".

The term "sensing" is used herein in the most generic sense of obtaining information from a physical stimulus; sensing therefore includes actions such as detecting, measuring, and so forth. A "sensor" is a device that performs sensing. Data or other signals that indicate or include results of sensing are sometimes referred to herein as "sensing results".

"Photosensing" is sensing of light. A "photosensor" is accordingly an electronic device that performs photosensing. More specifically, if optical signals include information, a photosensor that receives the optical signals may be able to sense the information and provide sensing results that indicate or include the information. A surface at which photosensing occurs is referred to herein as a "photosensitive surface".

The various exemplary implementations described below address problems that arise in obtaining information about a moving object such as a biological cell, a virus, a molecule, or a submolecular complex, such as in flow cytometry. Flow cytometry has become an indispensable tool in clinical diagnostics, such as in diagnosing cancer, AIDS, and infectious diseases during outbreaks, and also in microbiology and other areas. The cost and size of existing cytometers preclude their use in field clinics, water monitoring, agriculture/veterinary diagnostics, and rapidly deployable biothreat detection.

A number of commercially available flow cytometers use multiple excitation sources, each focused on a well-defined location or region separate from the others. Light emitted from each source's region is typically analyzed with a series of beam splitters, filters, and photomultiplier tubes (PMTs) in order to detect and distinguish differently stained cells or cells that concurrently carry multiple dyes. Cells are typically stained in solution with different dyes prior to insertion into a cytometer, and the measurement takes place in a fluidic channel in which cells traverse a detection region, typically at a speed of up to several meters per second. In the detection region, focused laser light (typically with an elliptical focus of 80 µm×40 µm) excites the dyes on the cells. The resulting fluorescent light can be collected by a microscope lens, sorted by band pass filters, and detected by PMTs or avalanche photodiodes (APDs). For each spot excitation, a respective set of filters and detectors is needed, which is costly and leads to bulky devices with strict requirements necessary to maintain optical alignment. Since the detection region is small and objects traverse it rapidly (typical dwell times are around 10 µsec), such flow cytometers have serious signal-to-noise (S/N) ratio issues for weakly fluorescing cells. These issues become more acute if multiple targets must be characterized and distinguished in some way, such as by counting.

A major cost in flow cytometry applied in clinical diagnostics is cost of reagents (e.g. antibodies and conjugated dyes). There are two ways to reduce the amount of consumables: First, one can reduce the required amount of analyte, e.g. by employing microfluidic techniques; and second, one can reduce the amount of consumable per analyte volume. Reducing amounts used would, however, reduce fluorescent intensity. It would be valuable to be able to overcome this constraint with a cost-effective and reliable technique to detect and distinguish weakly emitting cells.

Previous proposals to address these problems have involved spatially modulated single-color excitation to improve S/N ratios and to shift the detection limit toward weaker emitting cells. Spatial resolution can be maintained or improved in comparison with previous flow cytometry techniques, because fluorescing light is spatially modulated over a comparably large detection region; this is helpful because spatial resolution affects maximum detection or count rate of a device. But single-color techniques are limited, whether excitation is performed in a black/white approach or with a single-color interference pattern from a light source. Also, single-color techniques can encounter problems with wavelength sensitivity and bleaching of dyes. Because of low wavelength sensitivity, many flow cytometers with filter-PMT combinations are also constrained to use dyes with substantially different fluorescence wavelengths.

In addressing such problems, some exemplary implementations described below employ filter arrangements that transmit or reflect emanating light with one or both of two techniques: A filter assembly is used that provides different transmission functions in different segments of an object's path and/or a filter component is used that has a combined transmission function in which a set of simpler non-uniform transmission functions are superimposed. Such techniques make it possible to provide several different transmission functions in sequence within relatively short part of an object's path, so that the object's emanating light is relatively constant across the different transmission functions. These techniques also allow much greater variation in filter arrangements than would be possible with binary, black/white masks or single color masks. In addition, these techniques can be implemented to maintain higher spatial resolution and to allow higher photon flux on a photosensor. Time variation of emanating light resulting from such filters may provide sufficient information to make spectral characterization of particles feasible. Use of multiple colors may be compatible with particle identification based on native fluorescence; in particular, patterned filter arrangements allow for detection of differences in emission spectra and even the very small differences that occur in native fluorescence spectra might be detectable. It may also enable advanced color monitoring in printing applications by detecting even small differences in the reflection spectra of color spots while they are moving past interdigitated or otherwise patchworked or patterned filter arrangements.

The term "photon" refers herein to a quantum of light, and the term "photon energy" refers herein to the energy of a photon. Light can be described as having a "photon energy distribution" or, more commonly, a "spectrum", meaning the combination of photon energies that are included in the light; highly monochromatic light, for example, has a photon energy distribution or spectrum with one peak energy value.

Light can also be described as provided by a "light source," which, unless otherwise specified, refers herein to any device, component, or structure that can provide light of the type described; examples of light sources relevant to the below-described implementations include various kinds of pulsed and unpulsed lasers and laser structures, laser diodes (LDs), light emitting diodes (LEDs), superluminescent LEDs (SLEDs), resonant cavity LEDs, sources of broadband light that is spectrally filtered such as with a monochromator, and so forth.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where the speed of light in a medium M is a constant $c_M$ less than c, then M has an index of refraction $n_M=c/c_M$.

Where light changes direction in a way that can be illustrated or approximated as a vertex between an incoming ray and an outgoing ray that are both on one side of a surface, the change may be referred to as a "reflection"; similarly, to "reflect" light is to cause the light to change its direction of propagation approximately at such a surface, referred to herein as a "reflection surface". Similarly, where light changes direction in a way that can be illustrated or approximated as a vertex between an incoming ray and an outgoing ray that are on opposite sides of a surface between two media with different indices of refraction, the change may be referred to as a "refraction"; similarly, to "refract" light is to cause the light to change its direction of propagation approximately at such a surface, referred to herein as a "refraction surface". In many practical applications, both reflection and refraction occur at a surface, which may be referred to herein as a "partially reflecting surface".

Where light propagates at less than c, it may be useful to obtain an "optical distance" of propagation; for any segment of length d in which speed of propagation is constant $\epsilon^* c$, where $\epsilon = 1/n_{EFF} \leq 1$ and $n_{EFF}$ is an effective index of refraction for the segment, optical distance $D(\epsilon) = d/\epsilon$. An optical distance may be referred to herein as an "optical thickness", such as where light is propagating through a thickness of material.

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

The term "electrical signal" is used herein to encompass any signal that transfers information from one position or region to another in an electrical, electronic, electromagnetic, or magnetic form. Electrical signals may be conducted from one position or region to another by electrical or magnetic conductors, but the broad scope of electrical signals also includes light and other electromagnetic forms of signals and other signals transferred through non-conductive regions due to electrical, electronic, electromagnetic, or magnetic effects. In general, the broad category of electrical signals includes both "analog" and "digital" signals: An "analog" electrical signal includes information in the form of a continuously variable physical quantity, such as voltage; a "digital" electrical signal, in contrast, includes information in the form of discrete values of a physical characteristic, which could also be, for example, voltage.

Some implementations of filter arrangements described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In the implementations described below, structures, systems, or parts or components of structures or systems may sometimes be referred to as "attached" to each other or to other structures, systems, parts, or components or visa versa, and operations are performed that "attach" structures, systems, or parts or components of structures or systems to each other or to other things or visa versa; the terms "attached", "attach", and related terms refer to any type of connecting that could be performed in the context. One type of attaching is "mounting", which occurs when a first part or component is attached to a second part or component that functions as a support for the first. In contrast, the more generic term "connecting" includes not only "attaching" and "mounting", but also making other types of connections such as electrical connections between or among devices or components of circuitry. A combination of one or more parts connected in any way is sometimes referred to herein as a "structure".

Some of the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

A structure may be described by its operation, such as a "support structure" that can operate as a support as described above; other examples are defined below. In addition, a structure may be characterized by the nature of its parts or the way in which they are connected; for example, a "layered structure" is a structure that includes one or more layers, and the terms "partial structure" and "substructure" refer to structures that are in turn parts of other structures.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry, and a given hardware component can similarly be replaced by equivalent processor operations controlled by software.

Circuitry can be described based on its operation or other characteristics. For example, circuitry that performs control operations is sometimes referred to herein as "control circuitry" and circuitry that performs processing operations is sometimes referred to herein as "processing circuitry".

In general, sensors, processors, and other such items may be included in a system in which they are operated automatically or partially automatically. As used herein, the term "system" refers to a combination of two or more parts or components that can perform an operation together. A system may be characterized by its operation; for example, an "object distinguishing system" is a system that operates somehow to distinguish objects.

Within a system, device, or other article, components and parts may be referred to in a similar manner. One component of an object distinguishing system, for example, can be described as an "encoding component", in some cases referred to as an "encoding arrangement", in either case meaning that the component or arrangement operates to encode information; similarly, a system can include an "filter component", in some cases referred to as an "filter arrangement", in either case meaning that the component or arrangement operates to perform filtering, as explained in greater detail below; various other components are described below. In addition, a component or part may be identified by characteristics other than its operation.

In FIG. 1, object 10 is one of series 12 of objects 14 through 16 that travel along respective paths past filter arrangement 20. The term "path" is used herein in the general sense of a series of positions and/or configurations that a moving and/or varying object can have during its motion and/or variation. For generality, a part of a path is sometimes referred to herein as a "segment", which could encompass any continuous series of one or more positions and/or configurations within a path.

As object 10 travels past arrangement 20, light emanates from it, such as by emission, scattering (including, e.g. reflection), or transmission, and a portion of the emanating light is received by filter arrangement 20, as indicated by arrow 22. In general, the emanating light includes light within an application's range of photon energies, meaning that techniques as in FIG. 1 can be successfully used in a given application, e.g. flow cytometry, bio-chip readout, or any suitable kind of analyte detection, even though emanating light might also include photon energies that are outside the application's range and that might not interact with filter arrangement 20 in the same way as light in the application's range.

The term "object" is used herein in the general sense of any distinguishable thing about which information can be obtained by a sensor and included in its sensing results. In some implementations, sensors can obtain information about objects by receiving signals from them; for example, signals in the form of light can emanate from an object, whether through emission (e.g. radiation, fluorescence, incandescence, chemoluminescence, bioluminescence, other forms of luminescence, etc.), scattering (e.g. reflection, deflection, diffraction, refraction, etc.), or transmission, and can be sensed by a photosensor. The light "emanates from" or is simply "from" the object, and may be referred to herein as "emanating light". An object from which light is emanating may be referred to herein as a "light-emanating object". In other implementations, sensors can obtain information about objects in other ways, some of which are mentioned herein.

Examples of objects that could occur in implementations as described below include droplets, small volumes of fluid, single molecules, agglomerated molecules, molecule clusters, cells, viruses, bacteria, lengthy polymers such as DNA or protein chains, submolecular complexes such as tags on DNA or protein chains, microparticles, nanoparticles, beads or other small particles that can bind and carry specific chemicals or other analytes, emulsions, any such type of object in an array such as an array of sample wells, and a distinguishable region of a surface such as a small area of a sheet of paper or other image-bearing medium; a distinguishable region, could, for example, be a colored spot. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be a "scattering component" of a droplet. An analyte (i.e. a chemical species being investigated) in a droplet or other object can act as a fluorescent, absorbent, or scattering component. Analyte that is otherwise homogeneously distributed, for example, can be localized by binding to carrier beads, resulting in a moving object that emanates light or provides other signals in a way that depends on the analyte.

With respect to a light-emanating object, the expressions "characteristic of an object" and "emanating light including information" have related meanings: The term "characteristic" refers to a trait, quality, or property of an object that can be measured and that persists with a given value or within a given range or other subset of possible values while light that "includes information about the characteristic" is emanating from the object. In appropriate implementations, characteristics of an object could include mass, volume, density, cross-section or other shape, chemical composition, position, speed, acceleration, direction of movement, spin axis, directional or angular velocity or momentum, net charge, charge polarity, absorption spectrum, emission spectrum, scattering spectrum, and so forth. Therefore, emanating light "includes" information about a characteristic of an object if information included in the emanating light indicates a value, range, or other measure of the characteristic. Similar terminology can apply to types of signals other than emanating light.

Emanating light or other types of signals can "include information" in many ways, some of which are described below in relation to specific implementations. Various criteria could be used to determine whether emanating light or another type of signal includes specified information, and such criteria can be referred to as "encoding criteria". Some encoding criteria, for example, involve comparison of magnitude of a signal with noise magnitude, e.g. signal-to-noise (S/N) ratios, because S/N ratio can affect whether specified information can be recovered from sensing results obtained by photosensing emanating light. Other types of encoding criteria could be used as appropriate. Where emanating light or another type of signal satisfies an appropriate encoding criterion for specified information, the light or signal may be said to "encode" the information.

Similarly, sensing results, whether from photosensing emanating light or from another type of sensing, can "include information" in many ways, and similar encoding criteria could be applied as with signals. Where sensing results indicate one or more time-varying waveforms, the sensing results can be referred to as having "encoded time variation".

The term "waveform" is used herein in the general sense of any set of values that varies over one or more dimensions, whether continuous or discrete, whether analog or digital, and whether measured or obtained in any other way; a "time-varying waveform" is a waveform that varies over a time dimension. Some of the time-varying waveforms described below in relation to exemplary implementations include intensity values, but the expression "time-varying waveforms" also encompasses other values that vary over time, including purely numerical values with no specified units or other physical significance. A "sensed time-varying waveform" is a time-varying waveform that is indicated by sensing results obtained over time. For example, if a photosensor provides sensed quantities that indicate intensity of received light, its sensing results could indicate a time-varying waveform indicating intensity sensed over time.

In a system in which sensing results, emanating light, or other signals can include information about characteristics of objects, an object "travels" or is caused "to travel" if the object has a succession of positions over time with respect to one or more parts or components of the system or one or more patterns or other features of the system's environment such that information about the object's traveling, e.g. about speed or other rate of displacement, can be included in the emanating light or other signals. An object that travels is sometimes also referred to herein as "moving" or as having "motion" or "movement", but an object's traveling may result from any appropriate motion of the object and/or motion of parts or components of the system or patterns or other features of its environment. In other words, motion of an object includes any relative movement between the object and parts or components of a system or patterns or features of the system's environment, such as an encoding or sensing component of the system or a pattern of excitation or of filtering or another environmental pattern or feature.

A moving object's path is treated herein as providing a directional orientation as follows: A direction parallel or approximately parallel to the path is sometimes referred to as a "longitudinal" or "lengthwise" direction, while a direction perpendicular or approximately perpendicular to the path is sometimes referred to as a "radial", "lateral", or "transverse" direction. The lengthwise direction in which the object is moving is sometimes referred to as "forward" or "downstream", while the opposite direction is sometimes referred to as "backward" or "upstream". A radial direction away from the path is "out" or "outward", while a radial direction toward the path is "in" or "inward". Light propagating toward the path may be referred to as "incoming" or "incident", while light propagating away from the path may be referred to as "outgoing". A component or arrangement of components is "along" the path if it is disposed near the path and has some extent in a longitudinal direction. A component or arrangement of components is "around" the path if, in a plane transverse to the path, it intersects multiple radial directions, at least two of which are separated by approximately 180 degrees of arc. A direction that similarly goes around the path is sometimes referred to herein as a "rotation" direction. In general, it should be understood that the above directional orientation is arbitrary and only for ease of description, and that a moving object's path may have any appropriate orientation.

Emanating light that includes information about an object's traveling is sometimes referred to herein as "motion-affected" light, as including "motion-dependent information", or as having "motion-dependent encoding". For example, an object could travel by being conveyed in fluid, such as liquid, gas, or aerosol, along a path in which it emanates light that is transmitted and/or reflected by a filter arrangement to include information about the object's motion, thus becoming motion-affected light; in such a case the object may be referred to as being "carried" by fluid. In another example, an object contained in or otherwise supported by a support structure could travel due to relative scanning movement between the support structure and a filter component or another component such as a photosensor, and it could emanate light that is transmitted and/or reflected so that it becomes motion-affected light.

The term "optical filter" or simply "filter" refers herein to a light-transmissive or light-reflective part or component that transmits and/or reflects light in accordance with a respective criterion, sometimes referred to herein as a filter's "type". For example, one general category of filters is "band pass filters", referring to types of filters that, across some application's range of photon energies, e.g. a range of wavelengths or frequencies such as the visible range, preferentially transmit and/or reflect light within a subrange, sometimes referred to as a "band"; a band pass filter's type can therefore be specified by specifying the band or subrange of photon energies in which it transmits and/or reflects. A "blocking filter", which does not transmit or reflect any light in an application's range, can be viewed as a band pass filter with a band of zero bandwidth, while a "transparent filter", which transmits and/or reflects all light in an application's range, can be viewed as a band pass filter with a band that includes the entire range.

Filters can be combined and configured in many different ways, and all such combinations and configurations of one or more filters are encompassed herein by the general term "filter arrangement". A filter arrangement can include, for example, one or more "filter components", one or more "filter assemblies", and/or one or more "filter elements"; while the term "filter component" is generic, referring to any component that operates as a filter, the terms "filter assembly" and "filter element" are related and therefore a bit more specific, in that a filter assembly is a filter component that includes one or more filter elements, while a filter element is a filter component that generally does not include other filter elements within it. In general, filter elements and filter assemblies are sometimes also referred to as "masks". Also, the terms "transmit" and "reflect" and related words, as used herein, include each other unless otherwise specified, and terms such as "transmit/reflect" or "transmitting/reflecting" encompass transmission without reflection, reflection without transmission, and concurrent transmission and reflection.

Filter elements of various kinds could be included in filter assemblies, filter components, filter arrangements, and other combinations and configurations of filters, in a wide variety of ways. Within a given configuration of filters, relationships between filters can be described in a number of ways. For example, light can pass through a "sequence" of filters, meaning that specified light passes through the filters in a sequence: If a "radial sequence" of filters is along a path, for example, emanating light can pass through each of the filters in the sequence, beginning with the first and, after passing through each preceding filter, passing through the following filter; of course, light that is blocked by a preceding filter in a radial sequence would not reach its following filter. If a "longitudinal sequence" of filters is along a path, on the other hand, light emanating at each of a sequence of segments of on the path passes through a respective filter in the longitudinal sequence.

Several other categories of filters are described below in relation to exemplary implementations, including shadow masks, periodic masks, chirp masks, random masks, and so forth, and various other categories could be identified. As used herein, the term "random" refers to a pattern that is non-periodic over the entire length of a longitudinal sequence of filters; in contrast, a "periodic" filter assembly has at least one pattern that repeats more than once across the assembly's longitudinal length; and "chirp" patterns meet the above definition of random but can, with linearly varying time scaling, meet the above definition of periodic, in effect being a sequence of periods of linearly changing frequency or wavelength. A "shadow mask" is not a band pass filter, but rather an intensity-based filter assembly that, within a photon energy range of interest, transmits/reflects light of all energies, but with different parts of the filter transmitting/reflecting the light at different intensities, such as black and white and/or different gray scales. Any of these types of filter assemblies can be used to obtain "spatially modulated" emanating light, meaning emanating light that varies in time depending on position of an object from which it is emanating.

As used herein, the term "white", in a given implementation, refers to light with a spectrum that approximates maximum intensities across the implementation's full range of photon energies (which could be broad band, a combination of red, green, and blue, or another appropriate combination); the term "black" refers to the opposite of white, i.e. minimum available intensities across the full range, with the ideal being no light and therefore zero intensities. In emanating spectra, for example, light without maximal intensities across the full range as in white may be characterized as having a "gray level", such as one of the gray levels between white and black, or as having a "color", such as if it includes predominantly photon energies in a subrange, e.g. one of the colors in the visible range of wavelengths or in the infrared or ultraviolet ranges, or possibly a combination of such colors. Spectra that are neither black nor white are sometimes referred to herein as "non-binary spectra". Filter arrangement 20 includes either or both of two specified combinations or configurations of filters: Filter component 30 includes filter assembly 32 in which positions 34 and 36 have different transmission functions as indicated by different cross-hatching, while filter component 40 has a combined transmission function, represented by box 42, in which two or more different non-uniform transmission functions are superimposed. As a result of the differences in transmission functions, information can be encoded in time variation of emanating light from objects such as object 10.

As used herein, the term "transmission function" refers to a function that indicates, for some appropriate position or set of positions, the relationship of output and input light of a light-transmissive and/or light-reflective component such as a filter or filter assembly. A position's transmission function could indicate, for example, ratio of output intensity to input intensity at the position across a range of photon energies, sometimes referred to herein as the transmission function's "transmission spectrum"; a band pass filter, for example, could have approximately the same transmission spectrum at substantially all of its positions. A position could have any of a variety of other kinds of transmission functions, including, for example, an "intensity ratio", indicating the ratio of the position's output intensity to its input intensity, where the same intensity ratio applies to all photon energies across the relevant range; in the simple case in which each position of a filter has either an intensity ratio of zero or one, each position's transmission function could be one of a pair of binary values, such as black/white, ON/OFF, one/zero, or the like.

Further, a band pass filter or other filter element or assembly has a "uniform transmission function" if substantially all its positions have transmission functions that are approximately the same, and such a transmission function may be said to be "approximately uniform" for light transmitted/reflected through the filter element or assembly. Conversely, a filter element or assembly has a "non-uniform transmission function" if its transmission function is not approximately uniform; examples include periodic, random, and chirp filters as described above.

Transmission functions can, of course, be different from each other in various ways. For example, transmission functions of two positions can differ in "color", meaning that the positions have different transmission spectra; transmission functions with transmission spectra that have the same shape across a relevant range can differ in "intensity", meaning that they have different intensity ratios. Similar terminology can be applied to uniform transmission functions for filter elements, components, or assemblies. In FIG. 1, elements 34 and 36 have transmission functions that are different from each other. Also, simpler transmission functions that are superimposed to provide a combined transmission function can have different transmission functions; in FIG. 1, two of the simpler transmission functions superimposed to provide combined transmission function 42 are non-uniform and different from each other.

Different transmission functions can also be combined in a number of ways. For example, in a longitudinal sequence of filters, transmission functions are similarly combined into a sequence. In a stack or other radial sequence of filters or filter assemblies, on the other hand, transmission functions can be "superimposed", meaning that both transmission functions are applied to light passing through the component, resulting in a combined transmission function in which simpler transmission functions are superimposed. As used herein, a transmission function is "simpler" than a combined transmission function in which it is superimposed with at least one other transmission function, except in cases where the combined transmission function and all of the superimposed transmission functions have the same spectral shape or where the superimposed transmission functions have related shapes that result in uniform loss of detail when superimposed in specific phase relationships; although there are many abstract examples of superpositions that result in uniform loss of detail (e.g. two square waves of the same period and at opposite phase would have a flat line superposition) simplifying superpositions are very unlikely to occur between transmission functions with disparate shapes, such as random and periodic, random and chirped, chirped and periodic, and so forth—some detail might be lost locally in such cases, but most detail is preserved. Simpler transmission functions can be superimposed to obtain a combined transmission function in various ways other than a stack or radial sequence; for example, as described below in relation to some exemplary implementations, a single filter assembly can have a combined transmission function that is "stack-equivalent", meaning that it is approximately equivalent to a stack of filter components with simpler transmission functions. In some cases, including certain types of reflective filters, a stack-equivalent filter assembly can be equivalent to a combination of simpler filters without regard to the order in which they are superimposed, so that it is equivalent to a number of different stacks in which the simpler filters are in different orders.

As shown within combination 30, when object 10 is in segment 50 or segment 52 of its path, respective portions of emanating light are transmitted/reflected through positions 34 and 36 of filter assembly 32, as indicated respectively by arrows 54 and 56. Because of the different transmission functions, this transmitting/reflecting operation encodes information in time variation of the emanating light, represented by arrows 58. Specifically, if the emanating light from segments 50 and 52 has the same intensity or spectrum, the output light from positions 34 and 36 can affect its intensity or spectrum differently, and this difference can indicate, for example, the time at which object 10 moved between segment 50 and segment 52. In the illustrated example, segment 50 precedes segment 52 along the path of object 10, so that the portion of emanating light from segment 50 is transmitted/reflected according to the transmission function of position 34 before the portion of emanating light from segment 52 is transmitted/reflected according to the transmission function of position 36.

In some exemplary implementations below, for example, a filter assembly can have a longitudinal sequence of band pass filter elements with bands of different colors. As a result, output light from filter elements of different colors will have different intensities, depending on the spectrum of light emanating from an object, so that time variation of the output light encodes information about the emanating light's spectrum, i.e. about the type of the object. In other examples, information about speed or other displacement rate and position can be encoded by longitudinal filter sequences.

As shown within component 40, on the other hand, as object 10 passes through each of a series of segments that includes segments 60 and 62, respective portions of emanating light are transmitted/reflected with combined transmission function 42, as indicated by respective arrows 64 and 66. Because at least two of the simpler transmission functions that are superimposed in function 42 are non-uniform and different from each other, this transmitting/reflecting operation also encodes information in time variation of the emanating light, represented by arrows 68. If the emanating light from each segment in the series has the same intensity or spectrum, the output light from function 42 will be encoded in accordance with both of the simpler non-uniform transmission functions. In other words, information in accordance with both of the simpler transmission functions will be concurrently encoded in time variation of the emanating light.

In some exemplary implementations below, for example, a stack or stack-equivalent filter assembly combines a periodic or chirp transmission function that can encode information about an object's position, speed, or other displacement rate with a random transmission function that can encode information about an object's spectrum or type. Emanating light passing through the filter assembly is concurrently encoded with both types of information.

As suggested by the words "AND/OR" between combination 30 and component 40, the two are not mutually exclusive, and could be implemented together. As described below in relation to some exemplary implementations, a single filter assembly could encode information in time variation of emanating light in both of the ways illustrated for combination 30 and component 40.

The operation in box 70 photosenses the emanating light that has information encoded in its time variation, represented by arrows 58 and 68. This operation can be implemented with any suitable photosensing component, some of which are described below. In general, sensing results from photosensing take the form of analog or digital electrical signals, depending on the structure and circuitry included in the photosensing component. The operation in box 72 uses the sensing results from box 70 to obtain data indicating some or all of the encoded information, and can therefore be referred to as a "decoding" operation. The results of decoding can be used in a wide variety of ways, some of which are described below in relation to specific implementations.

Information about an object, as obtained in FIG. 1, can be used for a wide variety of purposes. In exemplary implementations described below, such information can, for example, be used to distinguish objects. In some applications, such as where the distinguished objects are registration marks in documents or other images, appropriate subsequent operations can be controlled based on the results of distinguishing objects.

Filtering arrangement 20 in FIG. 1 could be implemented in many different ways, some of which are described below. In some exemplary implementations below, for example, a filter component includes positions that have different transmission functions. In others, a filter assembly has a combined transmission function with superimposed simpler, non-uniform transmission functions. These techniques can be implemented together. As a result of these techniques, emanating light will have time variation due to different transmission functions, and the time variation of the emanating light can encode information about the object's spectral interactions such as the spectra in which it and other similar objects absorb, fluoresce, or otherwise interact with light, i.e. about the type of the object.

Figure 2:
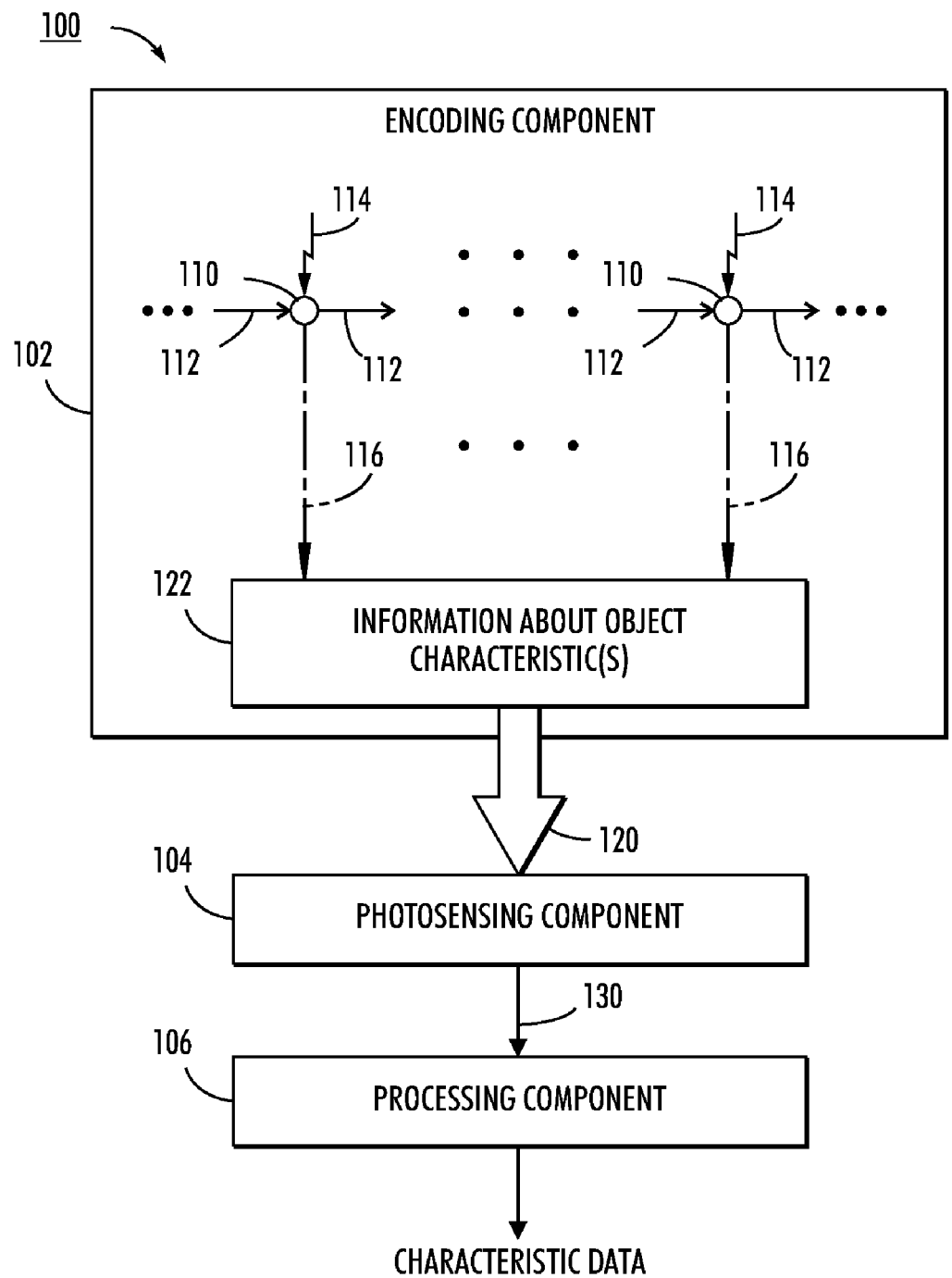
FIG. 2 is a schematic diagram showing components of a system in which light emanating from an object can include information about characteristics of the object.

FIG. 2 schematically illustrates general features of system 100, a system in which light emanating from a moving object can include information about characteristics of the object and in which features described above in relation to FIG. 1 can be implemented. As with other exemplary implementations described below, system 100 involves a combination of parts or components. Encoding component 102 illustratively provides output light that includes information about one or more object characteristics. Photosensing component 104 responds to the output light, providing sensing results such as electrical output signals with information in a form that can be communicated to processing component 106, possibly after conversion to other forms, e.g. for storage, transmission, and processing, such as optical or other electromagnetic signal forms. Processing component 106 can use the sensing results from photosensing component 104 to obtain and/or provide characteristic data indicating information about one or more object characteristics.

Object 110 illustratively travels in a direction indicated by arrows 112, passing through a succession of positions, two of which are illustrated. In some positions, object 110 can receive excitation, illustrated by arrows 114, and, in response, light as illustrated by arrows 116 can emanate, such as from fluorescence of a dye or other "tag" attached to object 110 or from native fluorescence or autofluorescence of object 110 itself, e.g. due to ultraviolet light or other excitation of intrinsic cell material or other material in object 110; except as otherwise noted, however, implementations described herein can additionally or alternatively employ chemofluorescence, biofluorescence, absorption, scattering, or other phenomena that do not require concurrent excitation. More generally, excitation could take any appropriate form and is not limited to illumination, and excitation and emanation need not be concurrent or otherwise coincident, but could have any appropriate relationship in space and time. Some examples of excitation are described below in relation to exemplary implementations.

Arrow 120 represents output light from encoding component 102. Box 122 between arrows 116 and arrow 120 illustrates that information about one or more characteristics of object 110 is included in the output light. As described below in relation to exemplary implementations, this information can be encoded in a variety of ways, including, for example, patterning excitation and/or patterning emanating light to obtain encoded output light represented by arrow 120.

Arrow 120 points to photosensing component 104, indicating that at least part of the encoded output light is illustratively sensed by component 104 to obtain sensing results. Based on the sensing results, component 104 provides electrical output signals represented by arrow 130. The electrical output signals can also include at least some of the information about object characteristics from box 120. As a result, processing component 106 can, in response to the electrical output signals, obtain and/or provide characteristic data indicating information about object characteristics.

Figure 3:
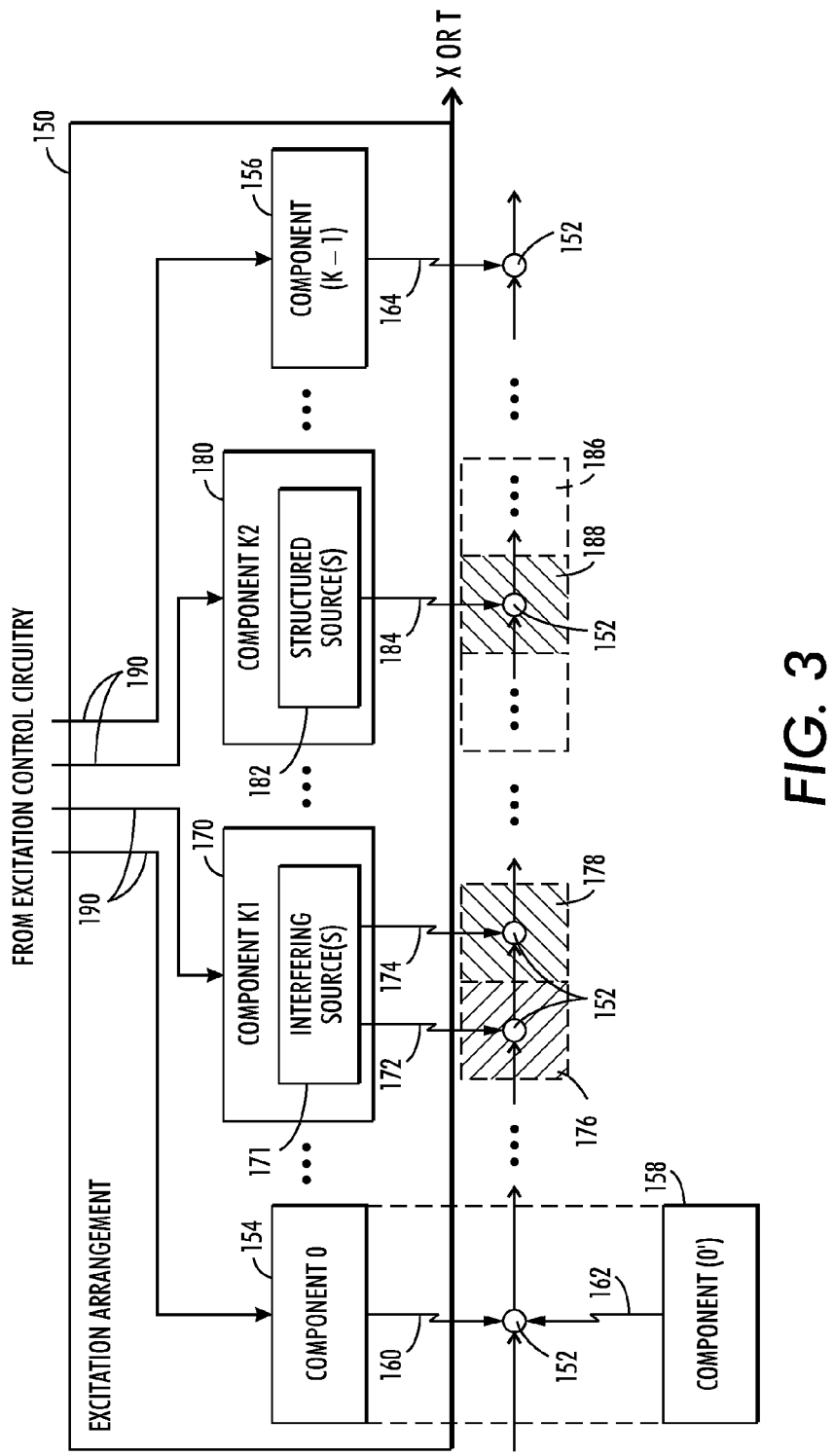
FIG. 3 is a schematic diagram of an excitation arrangement in an encoding component as in FIG. 2.
Figure 4:
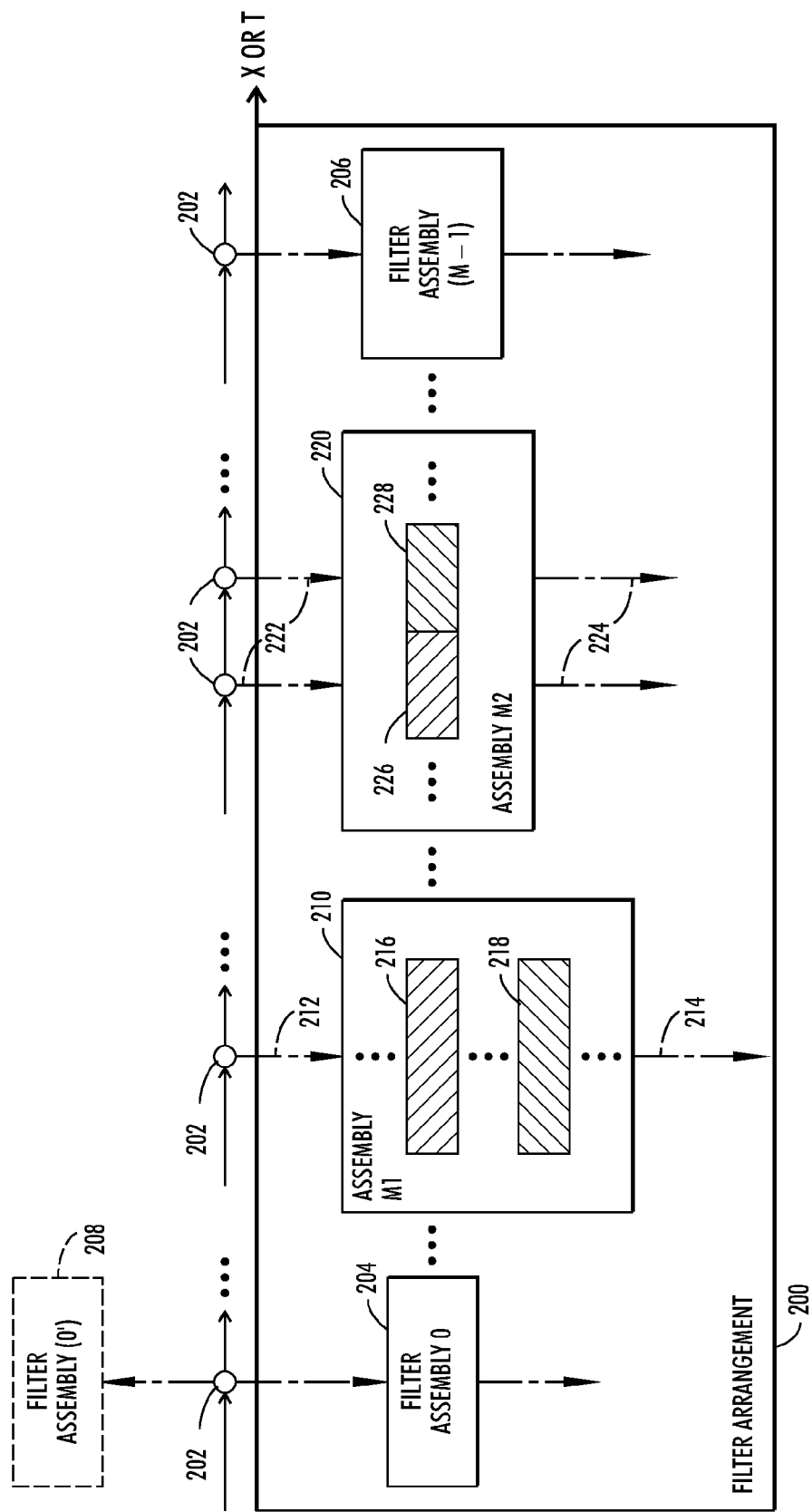
FIG. 4 is a schematic diagram of a filter arrangement in an encoding component as in FIG. 2.
Figure 5:
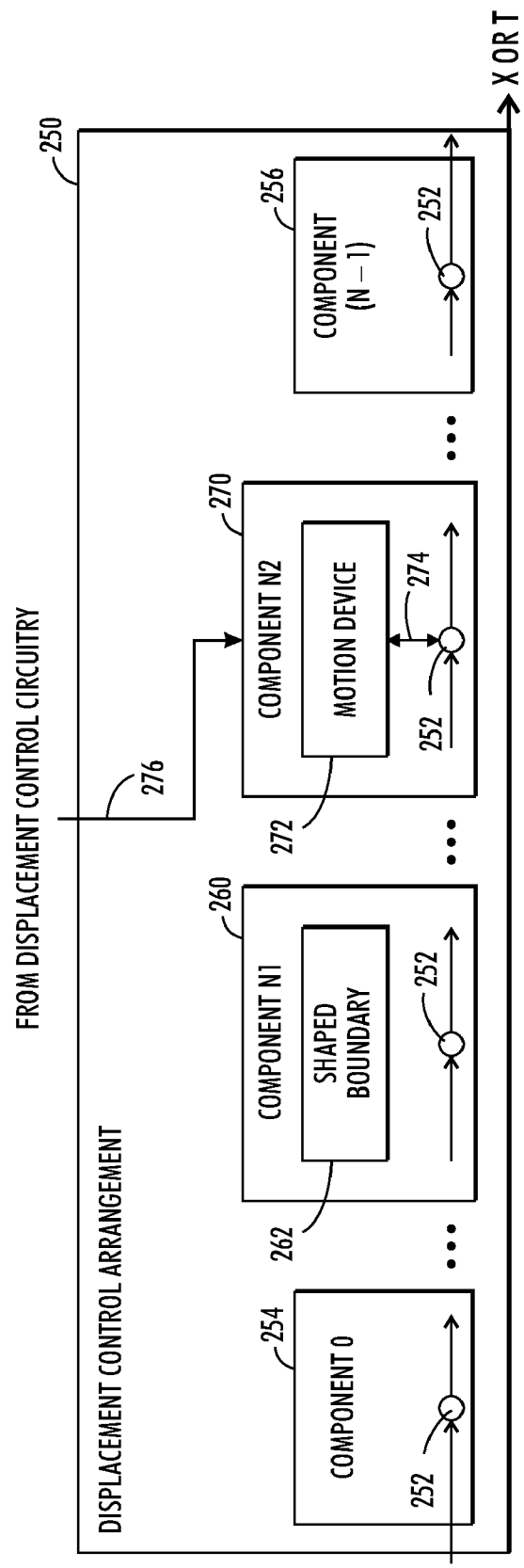
FIG. 5 is a schematic diagram of a displacement control arrangement in an encoding component as in FIG. 2.

Each of components 102, 104, and 106 in FIG. 2 could be implemented in a wide variety of different ways. FIGS. 3-5 illustrate several general features of implementations of encoding component 102, each of which involves an arrangement along a path traveled by a moving object.

In FIG. 3, excitation arrangement 150 is along a path traveled by moving object 152 as it emanates light within an encoding component such as component 102 in FIG. 2. As suggested by the one-dimensional coordinate axis labeled "x OR t", the path can be treated either as extending in space, such as along an x-direction, or as occurring over time, t; unless otherwise indicated hereafter in relation to a specific exemplary implementation, the x-direction refers to an object's path and therefore might not in some cases follow a straight line relative to the environment. Although the speed or other rate of displacement of object 152 may vary as it travels along the path, information about its speed or other rate of displacement can be sufficient to allow an approximate mapping between its x-direction positions and times t; more generally, mapping between an object's x-direction positions and times t can be based on any suitable system, such as with trigger detection techniques as described in U.S. Pat. No. 7,358,476, incorporated herein by reference in its entirety, or from other techniques, including obtaining information such as a trigger signal from an object's encoded signal.

Although excitation components could be positioned in any appropriate way along a path, the exemplary implementations described below generally involve arrangements of one or more excitation components along the x OR t axis, and FIG. 3 shows several exemplary components within a sequence of K excitation components 154 through 156, with component 154 labeled "0" and component 156 labeled "(K-1)". Excitation components need not, however, be arranged on only one side of the path, but rather could be positioned at any suitable positions around the path, depending on how excitations from different components interact. Also, two or more excitation components could be at the same position or in overlapping position ranges along the x OR t axis, but displaced in a rotation direction; a configuration of excitation components that are sufficiently displaced in a rotation direction so that they are around the path is illustrated by component 158, representing a possible position of another excitation component labeled "(0')" in arrangement 150, on the opposite side of the path traveled by object 152 from component 154.

Arrow 160 schematically represents excitation from component 154, while arrow 162 represents excitation from component 158. Similarly, arrow 164 represents excitation from component 156. Although excitation from components 154 and 158 can be provided concurrently to object 152, as suggested by arrows 160 and 162, excitation from component 156, represented by arrow 164, is provided at a subsequent position and time of object 152.

Excitation component 170, labeled "k1", illustratively includes one or more interfering light sources 171, resulting in two or more different types of excitation, with two types represented by arrows 172 and 174. The excitation represented by arrow 172 occurs while object 152 travels along a segment of the path through region 176, while the type of excitation represented by arrow 174 occurs while object 152 travels along a subsequent segment of the path through region 178. Regions 176 and 178 therefore form a pattern in space, an example of "spatially patterned excitation" used herein to refer to excitation that occurs in a pattern in space, i.e. a "spatial pattern"; spatially patterned excitation could, for example, include multiple periods of a spatial pattern. In particular, the excitation in region 176 has a different photon energy spectrum than the excitation in region 178, so that regions 176 and 178 could be described as having "different colors" of excitation. Several specific examples in which spatially patterned excitation includes regions of different colors are described below in relation to exemplary implementations; as will be understood from some of the examples, the x-direction of a path as shown in FIG. 3 may not follow a straight line, so that regions 176 and 178 may not in fact be oriented along a straight line through components 154 through 156—in some implementations, regions 176 and 178 could each extend parallel to such a line and the path could go back and forth between regions 176 and 178.

Excitation component 180, labeled "k2", illustratively includes one or more structured light sources 182. In other words, light sources 182 are structured to provide spatially patterned excitation, represented by spatial pattern 186. In the illustrated example, arrow 184 represents excitation provided in region 188, one of a pattern of regions through which object 152 passes while receiving excitation from component 180. The complete pattern of regions is represented in FIG. 3 by pattern 186.

FIG. 3 also illustrates lines 190 through which each of components 154 through 156 can receive control signals from excitation control circuitry (not shown). For example, one or more of the components in excitation arrangement 150 could include trigger detecting circuitry (not shown) as described above, and the excitation control circuitry could, in response to the trigger detecting circuitry, provide control signals causing the component to provide excitation, either in a steady state or time-varying manner. As described below in relation to exemplary implementations, time-varying excitation can encode information in a way similar to spatially patterned excitation.

Additional description of excitation techniques is set forth in co-pending U.S. Pat. No. 7,763,856, incorporated herein by reference in its entirety.

In FIG. 4, filter arrangement 200 is similarly along a path traveled by moving object 202 as it emanates light within an encoding component such as component 102 in FIG. 2. Filter arrangement 200 includes a combination of one or more filter assemblies along the path traveled by object 202.

Although filter assemblies could be positioned in any appropriate way along a path, the exemplary implementations described below generally involve arrangements of filter assemblies along the x OR t axis, and FIG. 4 shows several exemplary cross sections of filters within a sequence of M filter assemblies 204 through 206, with each cross section being taken parallel to the x OR t axis and with assembly 204 labeled "0" and assembly 206 labeled "(M-1)". Filter assemblies need not, however, be arranged on only one side of the path as shown, but rather could be positioned at any suitable positions around the path, depending on directional intensity variations of emanating light. Also, two or more filter assemblies could be at the same position or in overlapping position ranges along the x OR t axis, but displaced in a rotation direction; a configuration of filter assemblies that are sufficiently displaced in a rotation direction so that they are around the path is suggested by box dashed-line box 208 in FIG. 4, representing a possible position of another filter assembly labeled "(0')" in arrangement 200, on the opposite side of the path traveled by object 202 from filter assembly 204.

Filter assembly 210, labeled "m1", illustratively includes a radial sequence of filters through which light emanating from object 202, represented by arrow 212, can pass, with the output light from filter assembly 210 being represented by arrow 214. Filter assembly 210 could include any appropriate number of filters, with filters 216 and 218 being shown in FIG. 4.

The overall sequence of filter assemblies 204 through 206 illustrates a longitudinal sequence. Further, filter assembly 220 includes a longitudinal sequence of filters through which light emanating from object 202, represented by arrows 222, can pass, with the output light from filter assembly 220 being represented by arrows 224. Filter assembly 220 could include any appropriate number of filters in any appropriate longitudinal sequence, with adjacent filters 226 and 228 being shown in FIG. 4. Each of filters 226 and 228 could, for example, be a band pass filter, with the bands of filters 226 and 228 being sufficiently different to provide useful information about an emanation spectrum of object 202. Such a filter assembly is sometimes referred to herein as a "spatially patterned filter", because the filters it includes can be treated collectively as a single filter that has a pattern that varies as a function of position. Several examples of spatially patterned filters are described below in relation to exemplary implementations, and one or both of filters 216 and 218 in assembly 210 could also be implemented as a spatially patterned filter.

In the specific example of filter assembly 220, output light per arrows 224 can include encoded information from filters 226 and 228, and the encoded information can be recovered by photosensing the output light and performing appropriate operations on the sensing results. In general, filters 226 and 228 and other filters in filter assembly 220 can have any suitable lengths in the x OR t direction that allow recovery of the encoded information by photosensing and signal processing, including lengths smaller than the apparent extent of object 202 in the x OR t direction that may result in some loss of resolution analogous to blurriness or smearing. As described in relation to some exemplary implementations below, however, each of filters 226 and 228 can have length in the x OR t direction greater than or equal to an apparent extent of object 202 in the x OR t direction, while the lengths of filters 226 and 228 (and other filters in assembly 220) can be sufficiently small that characteristics of object 202 indicated by emanating light do not change while object 202 is traveling past assembly 220. In some specific implementations, filters 226 and 228 have parallel sides extending in a direction transverse to the path, and an assembly of such filters is sometimes referred to herein as a "striped filter" in which each stripe can be specified by filter type and its length (or width) in the lengthwise direction.

In the specific example of filter assembly 220, output light per arrows 224 can include encoded information from filters 226 and 228, and the encoded information can be recovered by photosensing the output light and performing appropriate operations on the sensing results. In general, filters 226 and 228 and other filters in filter assembly 220 can have any suitable lengths in the x OR t direction that allow recovery of the encoded information by photosensing and signal processing, including lengths smaller than the apparent extent of object 202 in the x OR t direction that may result in some loss of resolution analogous to blurriness or smearing. As described in relation to some exemplary implementations below, however, each of filters 226 and 228 can have length in the x OR t direction greater than or equal to an apparent extent of object 202 in the x OR t direction, while the lengths of filters 226 and 228 (and other filters in assembly 220) can be sufficiently small that characteristics of object 202 indicated by emanating light do not change while object 202 is traveling past assembly 220. In some specific implementations, filters 226 and 228 have parallel sides extending in a direction transverse to the path, and an assembly of such filters is sometimes referred to herein as a "striped filter" in which each stripe can be specified by filter type and its length (or width) in the lengthwise direction.

Filter arrangements similar to those shown in FIG. 4 may find application not only in fluidic implementations as described below but also in implementations in which objects in an array move relative to other components due, for example, to scanning movement. One such area of application is in image scanning, such as with scanning sheets of paper or other media that can bear images. In particular, object 202 could be a colored spot on a sheet of paper or other medium, and a filter arrangement could be used to obtain information about small differences in color of light emanating from object 202, e.g. color of reflected light in response to broadband illumination. Such information could be used to obtain position and/or color of object 202; for example, if object 202 is a registration mark with a color unique to registration marks, its color could be accurately distinguished from spots of other colors using techniques as described herein and its position could be obtained with sufficient accuracy to allow registration of the sheet, whether for image sensing or for printing or another operation on the sheet. Very high accuracy sensing of color is sometimes referred to as "hyperspectral color sensing".

In FIG. 5, displacement control arrangement 250 is similarly along a path traveled by moving object 252 as it emanates light within an encoding component such as component 102 in FIG. 2. Displacement control arrangement 250 includes a combination of one or more displacement control components, each of which is illustratively shown enclosing a respective segment of the path traveled by object 252. It would, of course, be possible to implement display control components in other ways, such as where an object travels along a path that is not enclosed within a channel or fluidic structure.

Although displacement control components could be positioned in any appropriate way along a path, the exemplary implementations described below generally involve arrangements of displacement control components along the x OR t axis, and FIG. 5 shows several exemplary components within a sequence of control components 254 through 256, with component 254 labeled "0" and component 256 labeled "(N-1)". Although each displacement control component in the sequence illustratively contains a respective segment of the path, it may be possible to implement displacement control components that affect displacement in overlapping segments of a path or that interact in other ways.

Control component 260, labeled "n1", illustratively includes shaped boundary 262, meaning that a boundary that extends partially or completely around the path, such as the boundary of a fluidic channel, has a shape that affects or controls displacement of object 252 as it travels along the path, such as by affecting its speed or other rate of displacement. Several examples of boundary shapes are described below in relation to exemplary implementations.

Control component 270, labeled "n2", illustratively includes motion device 272. Device 272 can illustratively cause lateral motion of a boundary in its segment of the path, as suggested by bidirectional arrows 274. Line 276 shows that device 272 can receive control signals from displacement control circuitry (not shown). Component 270 could also include trigger detecting circuitry (not shown), and the displacement control circuitry could respond to the trigger detecting circuitry by initiating operation of device 272, either in a steady state or time-varying manner. Examples of how device 272 could be implemented are described below in relation to specific implementations.

Figure 6:
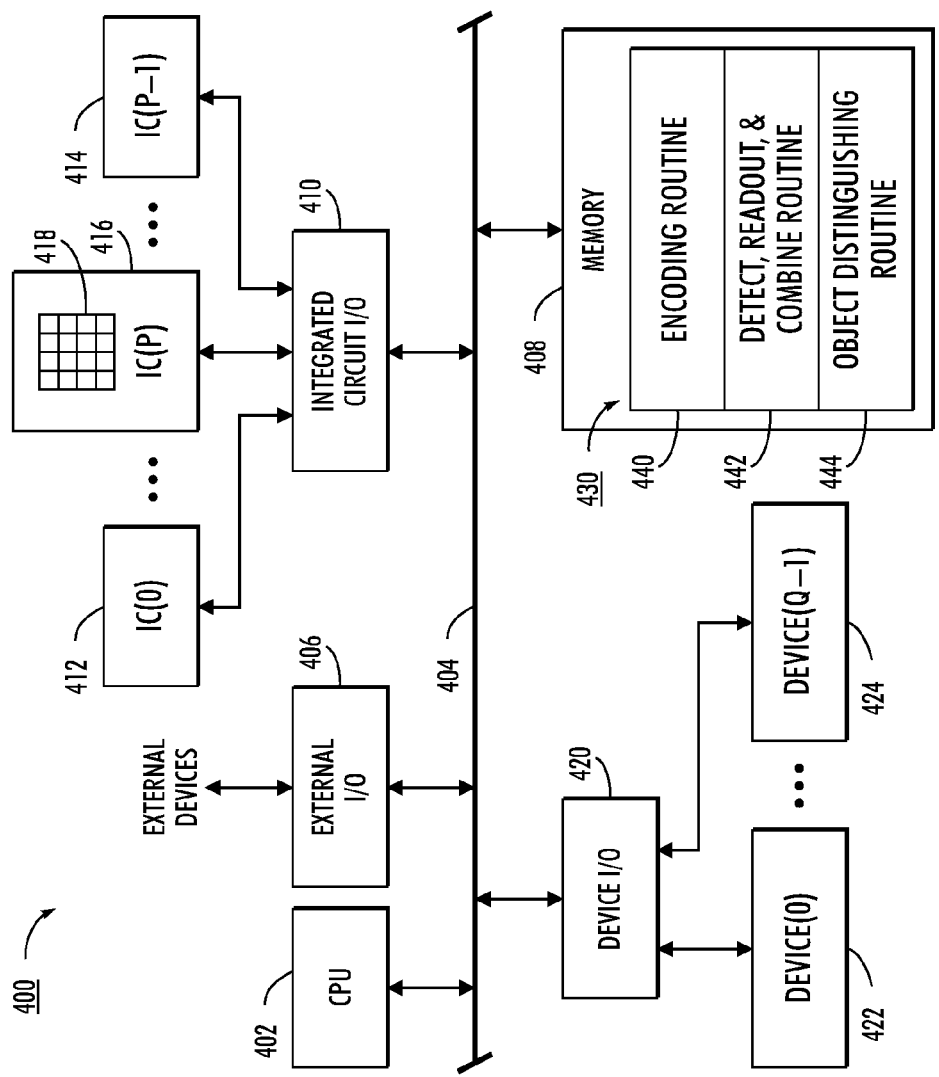
FIG. 6 is a schematic block diagram of a system in which components as in FIG. 2 can be implemented.

FIG. 6 illustrates system 400, an exemplary system that could implement components as in system 100 in FIG. 2. Although system 400 illustratively includes central processing unit (CPU) 402 connected to various components through bus 404, a wide variety of other architectures could be employed, including any appropriate combination of hardware and software, as well as specialized hardware components such as application specific integrated circuits (ASICs) for one or more of the illustrated components or in place of a software component executed by CPU 402. Furthermore, CPU 402 could be the CPU component of any suitable machine such as a laptop or desktop computer, a specialized computer for system 400, and CPU 402 and other digital components as shown could be replaced by other specialized circuitry, such as an analog signal processor; in a relatively simple application, CPU 402 could be implemented with a single digital signal processor or a CPU of a laptop or other personal computer receiving time-varying signals. On the other hand, in some applications, it may prove advantageous to implement all signal processing with analog circuitry, including operations that compare time-varying waveforms and that obtain their derivatives or other related waveforms, making it possible to replace substantially all the digital components as shown if appropriate.

System 400 also includes external input/output (I/O) component 406 and memory 408, both connected to bus 404. External I/O 406 permits CPU 402 to communicate with devices outside of system 400.

Additional components connected to bus 404 are within or connected to system 400. In the illustrated implementation of system 400, IC I/O 410 is a component that permits CPU 402 to communicate with ICs such as photosensing ICs; M ICs are illustrated in FIG. 6 by a series extending from IC(0) 412 to IC (P-1) 414. ICs 412 through 414 illustratively include IC(p) 416 with a photosensor array 418, which includes photosensing cells. Similarly, device I/O 420 is a component permitting CPU 402 to communicate with various devices in system 400, such as sensing and control devices; Q devices in system 400 are represented in FIG. 6 by device (0) 422 through device (Q-1) 424. In addition to excitation components as described above in relation to FIG. 3 and displacement control components as described above in relation to FIG. 5, devices 422 through 424 can include fluidic devices such as pumps, metering electrodes, smart gates, and other devices for gating and bifurcating, valves, flow or pressure sensors, and so forth. Such fluidic devices could be implemented in various ways; smart gates, for example, could be implemented with MEMS style microgates or by using electromagnetic forces, which are effective because most particles are charged such that an electric field can be used to direct them as desired in a channel.

Memory 408 illustratively includes program memory 430 although instructions for execution by CPU 402 could be provided in various other forms of software or hardware, on or off of CPU 402. The routines stored in program memory 430 illustratively include encoding routine 440; detect, readout, and combine routine 442; and object distinguishing routine 444. In addition, program memory 430 can also store a number of subroutines (not shown) that CPU 402 can call in executing routines 440, 442, and 444.

CPU 402 executes encoding routine 440 to encode information in light emanating from a moving object as it travels a path, i.e. information about characteristics of the object. In doing so, routine 440 can provide receive input signals from and provide output signals to devices 422 through 424. For example, to obtain appropriate motion of the object, CPU 402 can receive signals from sensors, perform computations to determine what fluidic operations are necessary, and then provide signals to activate pumps, metering electrodes, gates, and valves to produce appropriate relative movement between an object and other components of system 400 along its path. CPU 402 can also receive signals from trigger detecting devices and perform computations to determine what control signals to provide to excitation components, motion devices, or other components or devices in order to perform appropriate encoding in emanating light. Several examples of techniques that can be performed by encoding routine 400 are described below in relation to exemplary implementations.

In executing routine 442, CPU 402 can, for example, perform pre-sensing readout, obtain object information and sensing periods, perform sensing readout with sensing periods and analog adjustment, digitally adjust sensing results and store quantities for an object, and combine the quantities for an object to produce its characteristic data. Routine 442 could, for example, call a subroutine implemented as described in U.S. Pat. Nos. 7,358,476 and 7,547,904, each of which is incorporated herein by reference in its entirety. Such a subroutine can be implemented for single objects moving past arrays or for spaced multiple objects moving past arrays, provided spacings between objects are sufficient to avoid interference. Also, such a subroutine can follow a general strategy of performing a series of readout operations, after which information for an object is combined and its characteristic data is provided, although it would also be possible to provide the information from each readout operation immediately.

Figure 7:
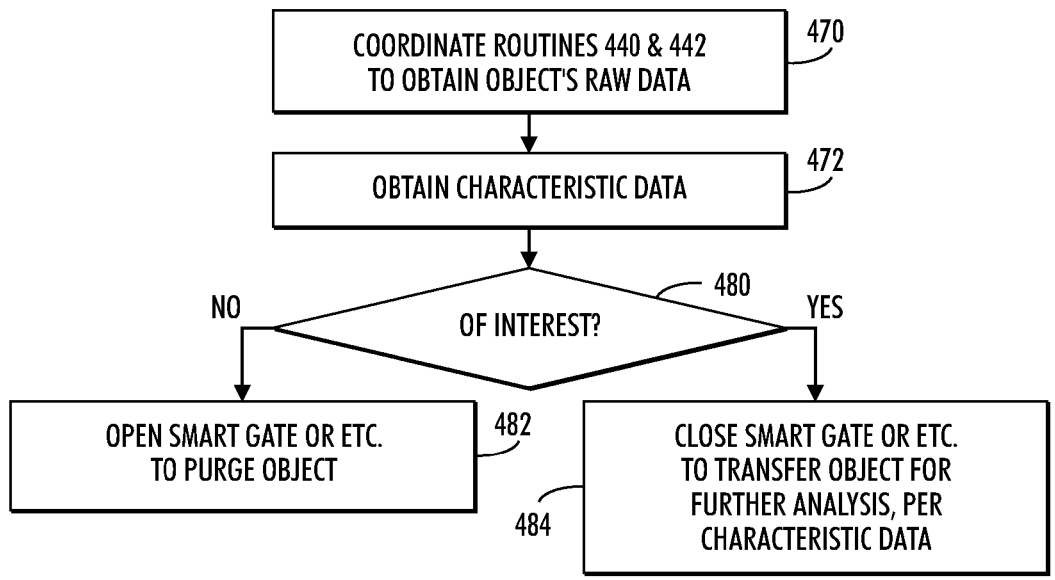
FIG. 7 is a flow chart showing general operations in an implementation of an object distinguishing routine as in FIG. 6.

FIG. 7 illustrates an example of how object distinguishing routine 444 in FIG. 6 could be implemented, using each object's raw data from routine 442 before it is used to obtain characteristic data for the object. Routine 444 can begin with the operation in box 470, which coordinates routines 440 and 442 as described above, obtaining an object's raw data, such as a data structure with photosensed quantities obtained from ICs 412 through 414.

The operation in box 472 receives the raw data from box 470, such as in the form of a handle or other item of data necessary to access a data structure. The operation in box 472 then uses the raw data to obtain the object's characteristic data, such as in one of the ways described below in relation to exemplary implementations. For example, an appropriate comparison technique could be used to obtain a comparison result indicating an object's type or other characteristic. The characteristic data from box 472 can indicate whether the object is of interest for further analysis, such as because it may be suspicious or harmful or, on the other hand, because it may be of interest for more refined analysis.

The operation in box 480 branches based on whether the object is of interest. If not, the operation in box 482 opens a smart gate or provides appropriate control signals to perform another operation to purge the object from the system. But if the object is of interest, the operation in box 484 ensures that the smart gate is closed or provides control signals for other suitable operations to transfer the object downstream so that a more refined or detailed analysis or other further analysis can be performed, possibly after concentration of the object with other similar objects by appropriate fluidic devices.

Figure 8:
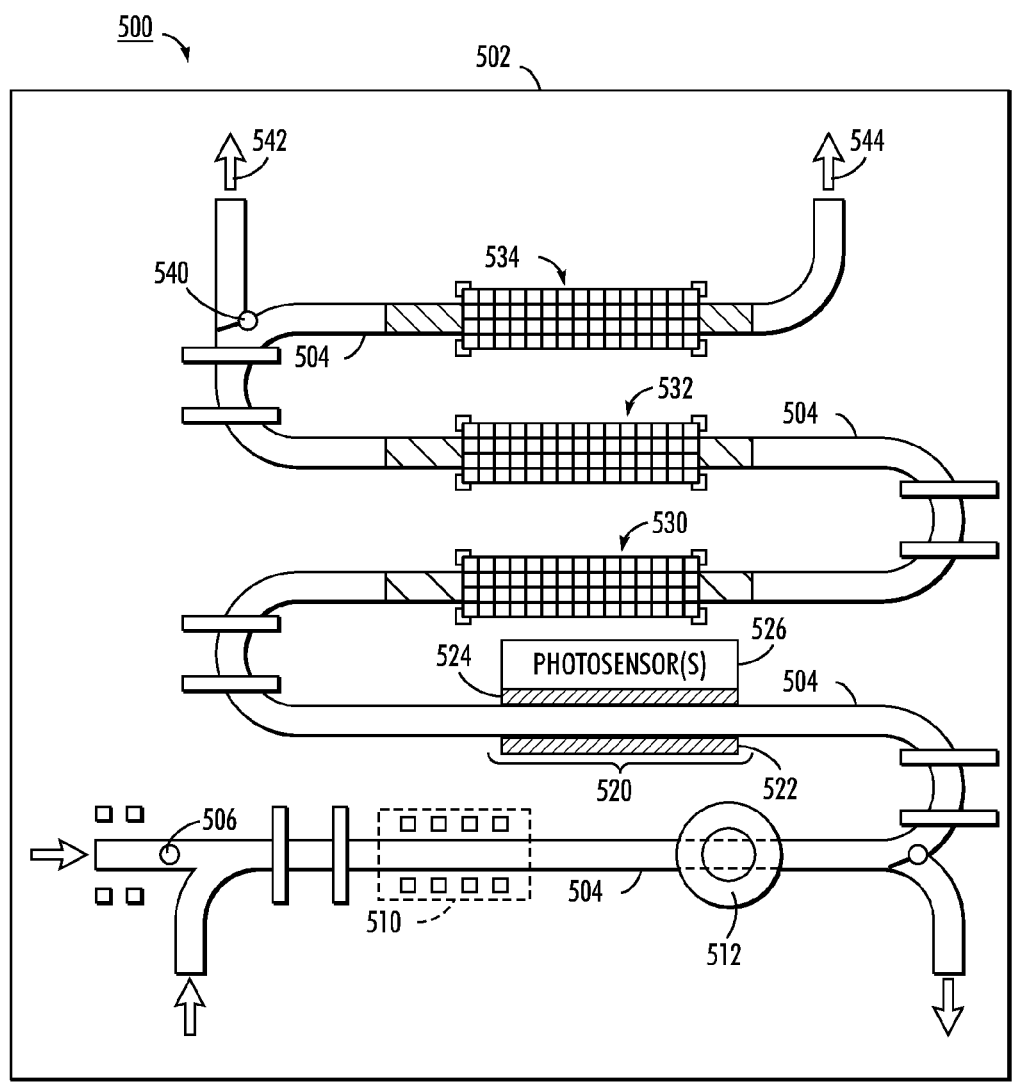
FIG. 8 is a schematic diagram of an analyzer in a fluidic structure, where the analyzer includes a system that can be implemented as in FIGS. 6 and 7.

FIG. 8 illustrates an application of a system as in FIGS. 6 and 7 in analyzer 500 on support structure 502, a fluidic structure. Defined in support structure 502 is serpentine channel 504 through which object 506 can travel, carried by fluid such as liquid, gas, or aerosol or moved in some other appropriate way. Object 506 can, for example, be a biological cell or another object of any of the types mentioned above.

The manner in which object 506 enters channel 504 and is carried by fluid can be the same as described in U.S. Pat. Nos. 7,358,476 and 7,547,904, each of which is incorporated herein by reference in its entirety. As explained there, object 506 can be carried through channel 504 by operation of propulsion components and can be purged or otherwise caused to exit, together with fluid that is carrying it, from one of several outlets, such as through toggling of valves. While in channel 504, object 506 can travel through a series of sensing components, each of which can obtain information about object 506.

The first two sensing components after object 506 enters channel 504 are illustratively Coulter counter 510, an electrically based particle size detector, and Mie scatter sensor 512, also a particle size detector. Information about object 506 from Coulter counter 510 and Mie scatter sensor 512 can be used in obtaining information about its other characteristics.

The next sensing component along channel 504 is emanating light encoder/photosensor 520, shown schematically in a cross-sectional view along an axis similar to the x OR t axis in FIGS. 3-5, although it would typically be implemented instead with components above and below channel 504, similarly to other sensing components described below. The schematic illustration of encoder/photosensor 520 includes excitation/displacement component 522, filter component 524, and photosensing component 526, all of which might be implemented in a variety of ways, including some of those described above and below.

After passing through encoder/photosensor 520, object 506 could be characterized without obtaining further information, or, as in the illustrated implementation, object 506 can continue through subsequent sensing components, illustratively including components 530, 532, and 534. These could, for example, include first and second fluorescence sensing components and a Raman scatter sensing component. Information obtained from any combination of the sensing components can be used to distinguish between types of objects, such as different types of biological cells, or to distinguish objects from environment or background. Based on such a distinction, valve 540 at a bifurcation junction can be toggled between two positions, with object 506 exiting as indicating by arrow 542 if valve 540 is in one position and exiting as indicated by arrow 544 if valve 540 is in another position.

The fluidic implementation in FIG. 8 is merely illustrative of a wide variety of implementations of the techniques described herein. For example, any appropriate fluidic or nonfluidic techniques could be used with a wide variety of different types of objects and various types of relative motion to gather various types of information about object characteristics.

Figure 9:
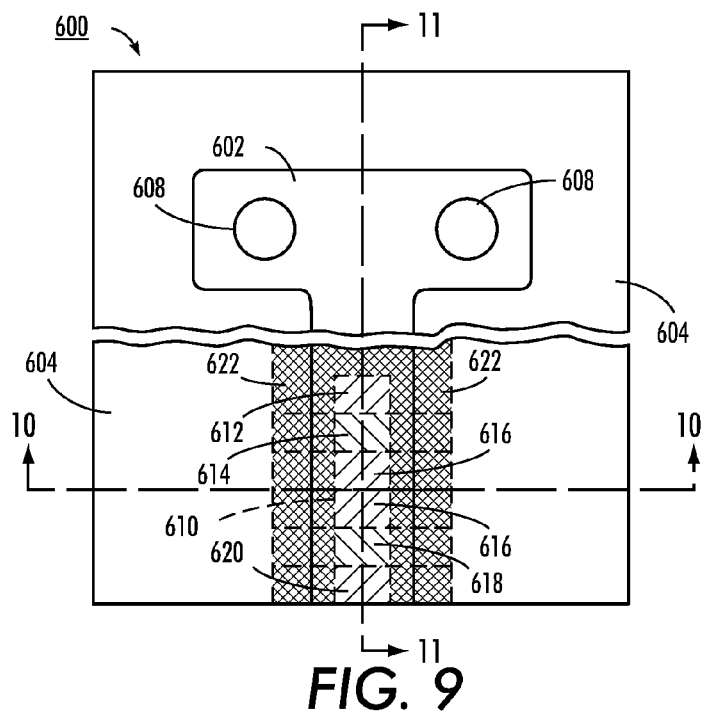
FIG. 9 is a top view of an article that can include a filter arrangement and that can be included in an encoding component as in FIG. 2.

FIG. 9 illustrates an example of article 600 with components that could be operated similarly to encoder/photosensor 520 in FIG. 8. Some features of article 600 can be understood from description in U.S. Pat. No. 7,529,438, incorporated herein by reference in its entirety. For example, article 600 includes a "fluidic structure", used herein to refer to a structure that depends for its operation on fluid positioning or fluid flow, such as, for liquids or gases, in response to pressure or, for liquids, as a result of surface tension effects; in general, the term "fluid" is used herein to encompass all media that can flow, including liquids, gases, aerosols, and so forth. The related term "channel" refers herein to any tube or other enclosed passage within a fluidic structure through which fluid flows during operation. A channel is therefore an example of a "fluidic region", used herein to refer to a region that can contain fluid. An operation "positions" fluid in a channel if it changes the fluid's position in any way that leaves the fluid in the channel.

A channel or portion of a channel through which objects can travel along paths are treated herein as having the directional orientation described above in relation to a path. In addition, a "cross section" lies in a plane perpendicular to a direction in which a local net flow of fluid through the channel or portion can occur; a direction in which a cross section extends can be referred to as a "transverse direction" or a "lateral direction." A channel or portion with approximately uniform cross section and substantially linear longitudinal direction can be referred to as "straight", and the channels and portions described herein are generally straight unless otherwise indicated.

In order to contain fluid, a channel or other fluidic region is typically "bounded", meaning that surfaces or surface areas bound it on at least some sides. A "boundary" of a channel or portion is the surface or combination of surfaces within which fluid contained in the channel is confined. A "port" is an opening that extends through the boundary of a channel or portion such that fluid can enter or exit through the port; in general, a port is relatively small compared to the length of the channel or portion, and the boundary is treated as extending across the port as if the port did not exist.

As described below, article 600 can include two light-transmissive components, and FIG. 9 shows article 600 in a top view through one light-transmissive component. In this view, the inner region between the light-transmissive components includes two main portions, channel portion 602 that can contain fluid and non-channel portion 604 that surrounds channel portion 602; channel portion 602 is illustratively shaped like a "T", but could instead have an L-shape or any other suitable shape, including a serpentine shape as in FIG. 8. Ports 608 are openings through one of the light-transmissive components, allowing entry and exit of fluid into and out of channel portion 602.

FIG. 9 also shows filter assembly 610 in dashed outline. Filter assembly 610 is illustratively a spatially patterned filter with a longitudinal sequence of band pass filters that includes filters 612, 614, 616, 618, and 620. Filters 612, 616, and 620 are illustratively cross-hatched similarly to each other to indicate that they have the same or approximately the same band, while filters 614 and 618 are also cross-hatched similarly to each other, illustrating that they also have the same or approximately the same band, a band that is different than that of filters 612, 616, and 620. In other words, filter assembly 610 is a striped filter in which each of filters 612 through 620 can be specified by the band that it passes and its length in the x-direction in FIG. 9.

Surrounding filter assembly 610, blocking material 622 is structured and positioned to provide an aperture. Blocking material 622 can, for example, be a material with approximately zero light transmission that prevents scattering and reflection of light, also preventing light entering filter assembly 610 from nearby fluorescing objects. Blocking material 622 can be produced during the same operation that produces filters 612 through 620 and can in effect be part of filter assembly 610.

Figure 10:
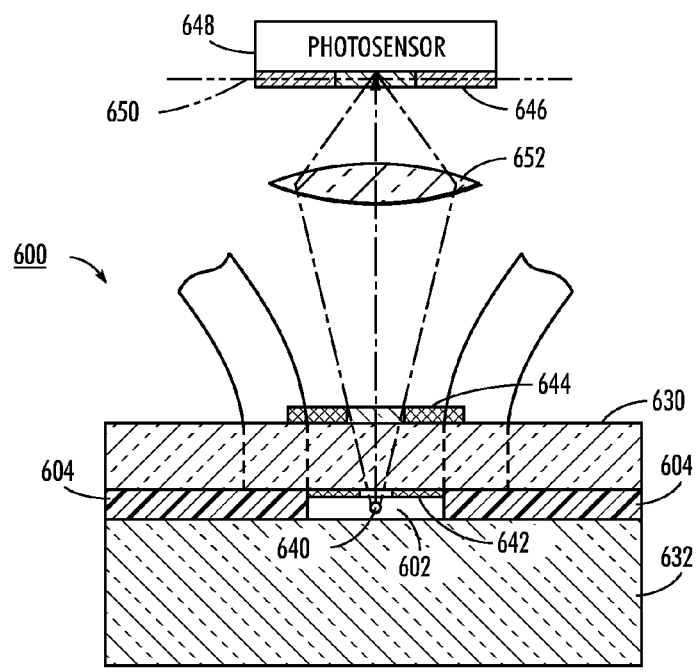
FIG. 10 is a cross-sectional view of an implementation of an article similar to that in FIG. 9, taken along the line 10-10.

The cross section in FIG. 10 shows how light-transmissive components 630 and 632 are separated by material in non-channel portion 604. For example, components 630 and 632 can each include quartz or another suitable material such as glass or acrylic with an appropriate thickness; in a successful implementation, for example, component 630 has a thickness of approximately 0.3 mm, while component 632 has a thickness of approximately 1.0 mm or less; depending on the application, on stability of materials used, and size of objects being characterized, suitable thicknesses might range from a few millimeters down to 0.1 mm or even less. The optimum distance between them is determined primarily by the size of objects being characterized. For biological cells with typical dimensions of 10 µm, for example, the distance can be approximately 20 to 50 µm, maintained by material in non-channel portion 604, which could, for example, be a suitable photoresist material such as SU-8 or another polymer material. Alternatively, a wall (not shown) could be formed around channel portion 602, and non-channel portion 604 could then be filled with epoxy material that seals a lateral boundary around channel portion 602. Various other techniques could be used to produce a similar fluidic structure, including hot embossing, nano-imprinting, or injection molding, and channel portion 602 can have appropriate dimensions, such as for waveguiding as described in U.S. Pat. No. 7,529,438, incorporated herein by reference in its entirety.

FIG. 10 also shows object 640 from which light is illustratively emanating upward, as illustrated by an emission cone. Although the emission cone is illustratively shown as a single cone, the actual emission cone would depend on angles of total internal reflection at surfaces through which emanating light is transmitted in article 600. FIG. 10 illustrates three alternative filter assembly positions, with filter assembly 642 facing channel portion 602, on the lower surface of component 630; with filter assembly 644 being outside of channel 602 on the upper surface of component 630; and with filter assembly 646 being spaced apart from the upper surface of component 630, adjacent photosensor 648, which could, as in other implementations, be a single, large area photosensor (such as a photo-diode, an avalanche photo-diode (APD), or a photo-multiplier tube (PMT)), or an appropriate array of photosensing cells whose sensed quantities can be combined to obtain a single photosensed quantity, such as an intensity value for a sensing period. As suggested in FIG. 10, the emission cone from object 640 is imaged onto image plane 650 extending through filter assembly 646 by optical component 652, illustratively shown as a single lens, but which could be any suitable lens, lens system, or other optical component, some examples of which are described in co-pending U.S. patent application Ser. No. 11/698,409, entitled "Method and System Implementing Spatially Modulated Excitation or Emission for Particle Characterization with Enhanced Sensitivity", incorporated herein by reference in its entirety.

The emission cone for filter assembly 642 includes the range of angles of incident light that are not totally reflected by the surface of assembly 64. Similarly, the emission cone of filter assembly 644 is determined by the range of angles within which emanating light is not subject to total internal reflection at the surface between component 630 and assembly 644. The emission cone for filter assembly 646 is similar to that for filter assembly 644, but can occupy a smaller area on filter assembly 646 due to the effect of optical element 652.

In one illustrative example, channel portion 602 contains water with an index of refraction n=1.33, and object 640 has a diameter d=7 µm, which would be typical for certain biological cells, e.g. T-lymphocytes. Channel portion 602 has a height between components 630 and 632 of 30 µm and its distance from the lower surface of filter assembly 642 is approximately h=15 µm. Component 630 is acrylic with an index of refraction n=1.48, surrounded by air with an index of refraction n=1. If filter assembly 642 were absent, the escape angle from channel portion 602 to component 630 would be α(escape)=48.75°, which would determine the size of the emission cone in which light from object 640 can leave channel portion 602. The angle of total internal reflection at the upper surface of component 630, on the other hand, can be obtained as α(TIR)=42.51°, which determines the size of the emission cone for light that leaves component 630. The diameter of a disk illuminated by object 640 at the water-acrylic interface can be obtained from D=d+2*h*tan (α(escape))= (7+(2*17.1))µm=41.2 µM, where 17.1 µm is the radius of the maximum emission cone that can pass through component 630 without total internal reflection. The "minimum feature size" ("MFS") for a pattern suitable to detect object 640 at the water-acrylic interface would be equal to D or approximately 40 µm; in general, MFS can be defined for a mask along the path of an emanating particle as the extent in the path's longitudinal direction of the mask's smallest uniform feature (i.e. the smallest transmitting filter element or the smallest blocking filter element, whichever is smaller).

Where photosensor 648 is implemented with a numerical aperture that makes the emission cone smaller, filter assembly 642 can accordingly have a slightly smaller MFS than calculated as above; similarly, in some acrylic implementations of component 630, some light typically leaves component 630 at an angle slightly higher than α(TIR), which could also allow a slightly smaller MFS. In general, however, the MFS of filter assembly 642, if too small, results in passage of light from an object's emission cone around both sides of a feature in assembly 642, so that the time-varying signal of a photosensor, while containing some information, may not accurately indicate information about displacement of the object as it travels along a path past filter assembly 642. Similar considerations apply to filter assemblies 644 and 646, with the MFS of filter assembly 644 necessarily being significantly larger than that of filter assembly 642, but with the MFS of filter assembly 646 possibly being intermediate between those of assemblies 642 and 644, depending on the precision of optical component 652. In implementations without optical components, photosensor 648 could be slightly larger due to spreading of emanating light. For a biological cell on the order of 10 µm, a typical MFS would be in the range of 10-20 µm. The channel width might be an order of magnitude larger, while the channel length might be two orders of magnitude larger, and the width of the filter assembly would depend on the channel width. For example, assembly 642 might be 100 µm wide and approximately 1.0 mm long. At the time of manufacture, a calibration operation could be performed using objects that are, for example, tiny beads with known fluorescence spectra; light emanating from such beads could be measured and used to obtain calibration values necessary to adjust measured values to obtain known intensities for such objects.

Figure 11:
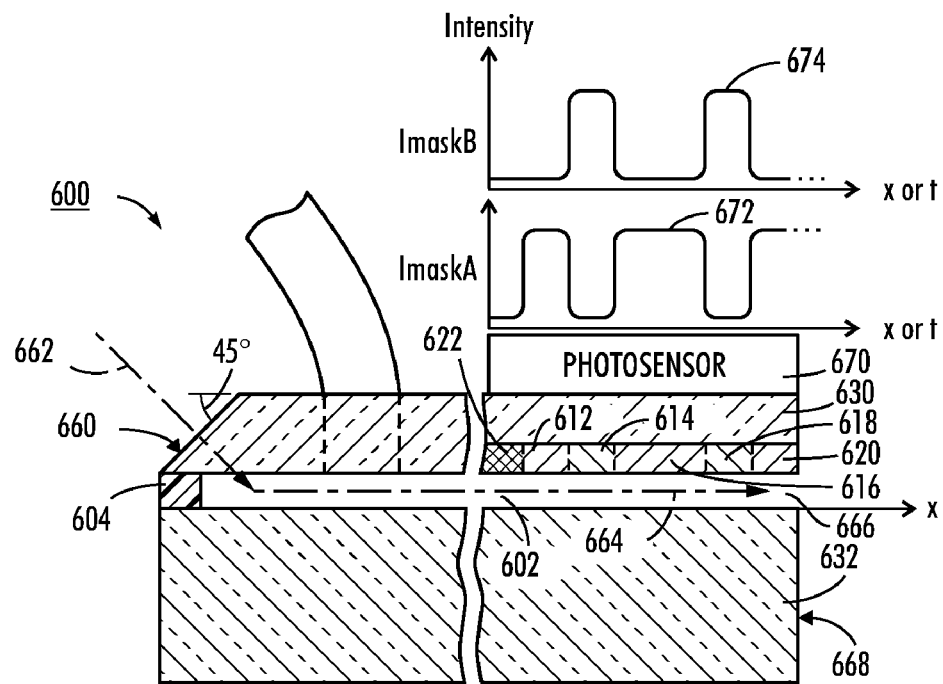
FIG. 11 is a cross-sectional view of another implementation of an article similar to that in FIG. 9, taken along the line 11-11, together with graphs of sensed intensities.

The cross section in FIG. 11 further illustrates how component 630 has oblique surface 660, a light interface surface that is illustratively at an angle of approximately 45° to the inward-facing surfaces of components 630 and 632. As a result, incident excitation light at a direction approximately perpendicular to surface 660, as illustrated by arrow 662, can cause and couple with light propagating through channel portion 602, as illustrated by arrow 664, as described, for example, in U.S. Pat. No. 7,529,438, incorporated herein by reference in its entirety. Excitation light could have any appropriate wavelength, such as 266 nm, for example. The distance from surface 660 to obtain appropriate homogeneity can be determined, as described, for example, in U.S. Pat. No. 7,456,953, incorporated herein by reference; the distance can also be sufficient to allow integration of blocking material 622.

In the illustrated implementation, the end of channel portion 602 at right in FIG. 11 is open, providing an additional port 666 through which fluid can enter into or exit out of channel portion 602. Alternatively, article 600, instead of ending at transverse end-surface 668, could extend to another area with ports similar to ports 608, such as with a part symmetrical about the position of surface 668; in this case, fluid could flow through channel portion 602 between ports 608 and similar ports at the opposite end of channel portion 602.

In the implementation in FIG. 11, the filters within filter assembly 610 are shown in cross section, and, in this implementation, the filters do not overlap, but rather are adjacent to each other. They could, for example, be integrated into a recess in the lower surface of component 630 such that they are even with the surrounding surface of component 630 or they could be surrounded on all sides by a layer of shadow (light blocking) or transparent material of the same thickness; in either of these approaches, the filters could be implemented so that there is no step at the edges of assembly 610. The size of the gap, if any, between adjacent filters depends, for example, on the resolution of the technique used to produce the filters. If the filters are produced by printing two different light-absorbing materials that have different absorption spectra (in which case a surrounding layer of shadow or transparent material could also be printed around them), the registration and gaps between filters depend on the resolution of the printing technique used; examples of such techniques are described in U.S. Pat. No. 7,365,022 and in U.S. Pat. No. 7,879,390, each of which is incorporated herein by reference in its entirety. In general, however, the techniques described herein do not require highly precise positioning of filters—a small gap between filters should not significantly affect time-varying signals that result from an object traveling past such filters while it emanates light.

The upper part of FIG. 11 includes two graphs illustrating intensities detected by photosensor 670 in response to two types of objects, one emanating light of color "A", the other emanating light of color "B". Filters 612, 616, and 620 have bands that allow light of color "A" to pass, while filters 614 and 618 have bands that allow light of color "B" to pass.

Curve 672 illustrates intensities indicated by sensing results from photosensor 670 if object 640 emanates light of color "A" as it travels along the path through channel portion 602. In other words, the emanating light's photon energy distribution matches the band for filters 612, 616, and 620 so that curve 672 is high along those filters but low along filters 614 and 618; its high value is indicated on the vertical axis as "ImaskA".

Curve 674, on the other hand, illustrates intensity indicated by sensing results from photosensor 670 when object 640 emanates light of color "B" as it travels along the path. In this case, the emanating light has a photon energy distribution that matches the band for filters 614 and 618 but not for filters 612, 616, and 620, so that curve 674 is at a high intensity along filters 614 and 618, "ImaskB", and at a low intensity elsewhere.

Curves 672 and 674 illustrate an example in which two different types of objects provide signals that are approximately complementary, except at the far left along blocking material 622 where both curves are at approximately zero intensity. In a simple implementation, for example, filters 612, 616, and 620 could be red band pass filters, filters 614 and 618 could be green band pass filters, each object could either be a red fluorescing particle or tag, i.e., emanating light of color "A", or a green fluorescing particle or tag, i.e., emanating light of color "B". As suggested, curves 672 and 674 could be plotted based on the x-direction position of object 640 or based on the t-position within the time varying output signal from photosensor 670, which could be provided continuously or by any suitable form of sampling, such as by periodic readout at an appropriate frequency. The high intensities of curves 672 and 674 would be reduced to the extent that blocking material 622 prevents light from reaching photosensor 670.

As a result, output signals from photosensor 670 can be used to distinguish types of objects, in this case to distinguish objects that emanate light of color "A" from objects that emanate light of color "B", and examples of techniques that distinguish types of objects in various ways are mentioned below in relation to exemplary implementations. In some examples, emanating light encoded by a filter assembly with stripes of random lengths can be analyzed by comparing a resulting time-varying signal with one or more templates or other signals to determine an object's type, displacement, and position to a high level of precision.

Figure 12:
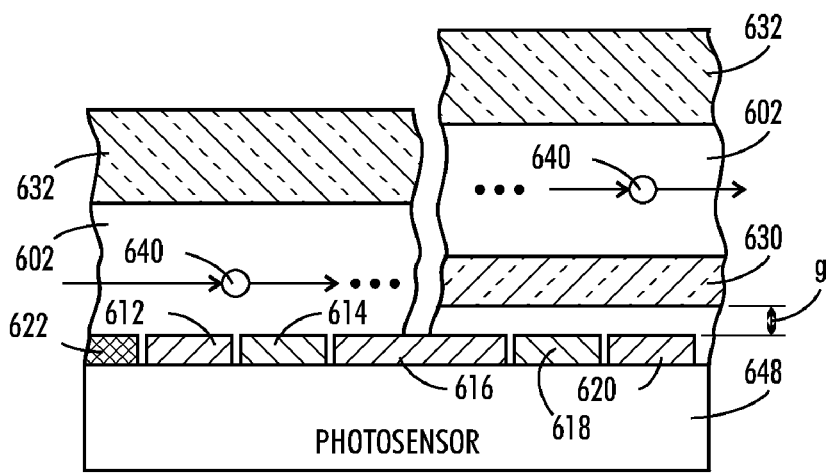
FIG. 12 is a partially schematic cross-sectional view showing two ways in which a filter arrangement on a photosensitive surface can be configured in an encoding component as in FIG. 2.

FIG. 12 illustrates two alternative implementations similar to those in FIGS. 9-10, and with the same reference numerals, but with filter assembly 610 on a photosensitive surface of photosensor 648. These implementations could be implemented by printing or otherwise depositing and patterning filters 612, 614, 616, 618, and 620 and blocking material 622, such as in the manner described above, or by producing a longitudinal sequence of band pass filters in any other appropriate way, with some possible techniques being described below in relation to other exemplary implementations. In the implementation at left, photosensor 648 also operates as one side of channel portion 602, replacing light-transmissive component 630 along at least a portion of the channel. In other words, filter assembly 610 is positioned similarly to filter assembly 642 in FIG. 10, allowing a very small MFS. In the implementation at right in FIG. 12, photosensor 648 is outside of channel portion 602 separated from the outer surface of component 630 by a small gap of height gas shown. In this implementation, filter assembly 610 is positioned similarly to filter assembly 644 in FIG. 10, but not directly on the outer surface of component 630, so that a larger MFS is necessary. The gap between component 630 and photosensor 648 can be maintained by spacers or other appropriate support components, and can be sufficiently large that photosensor 648 does not interfere with anti-resonant waveguiding within channel portion 602, which can be implemented, for example, in the ways described in U.S. Pat. No. 7,386,199, incorporated herein by reference in its entirety.

Absorption filters as described above in relation to FIGS. 9-12 can be implemented in a multitude of ways. For example, rather than only two types of band pass filters that have bands for respective colors, three or more types of filters with three or more respective colors could be used. Similarly, a filter assembly can include band pass filters and other types of absorption filters as would be found in a shadow mask. Furthermore, with printed filters as described above or with other filters produced with layers of material, overlapping band pass filters could be produced, providing additional information. In addition, absorption filters could be combined with reflection filters, as described below in relation to some exemplary implementations.

Figure 13:
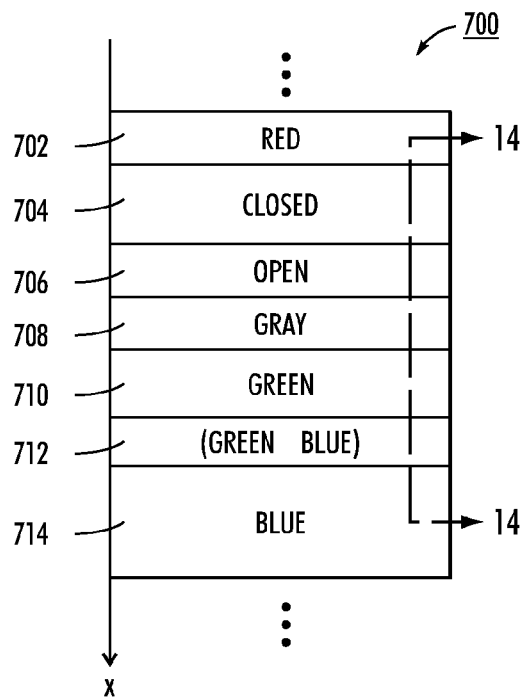
FIG. 13 is a schematic top view of another filter arrangement that can be included in an encoding component as in FIG. 2.

Filter assembly 700 in FIG. 13 illustrates some of these variations. In the illustrated assembly, each stripe is labeled with a description of its filter criterion. Stripe 702 is a red band pass filter; stripe 704 is a closed filter, meaning that it allows no transmission; stripe 706 is an open filter, meaning that it allows full transmission; stripe 708 is a gray filter, meaning that it passes all photon energies across a range of interest, but at an intensity in between an open filter and a closed filter; stripe 710 is a green band pass filter; stripe 712 is a combined band pass filter that passes only the intersection of blue and green; and stripe 714 is a blue band pass filter. In addition, as can be seen, the widths of the stripes are random rather than periodic.

Figure 14:
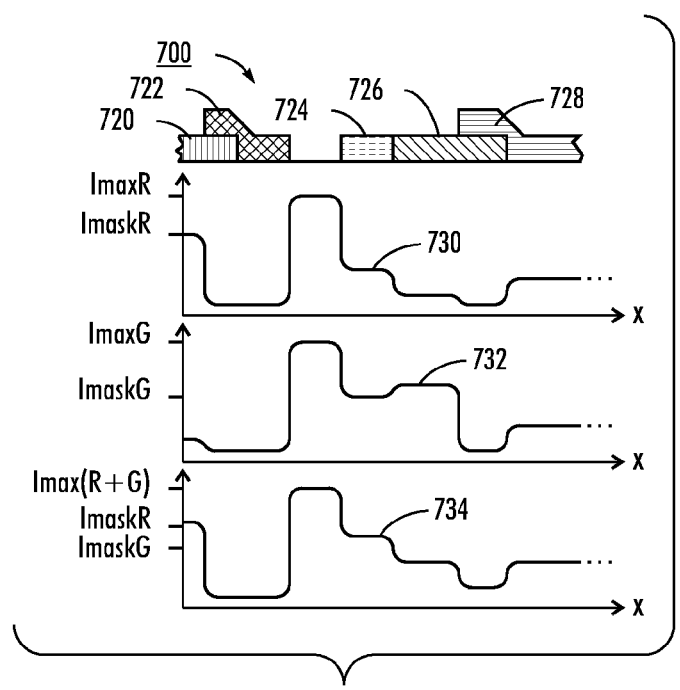
FIG. 14 is a cross-sectional view of an implementation of a filter arrangement similar to that in FIG. 14, taken along the line 14-14, together with graphs of transmitted intensities.

The cross section in FIG. 14 illustrates one way of implementing filter assembly 700 in FIG. 13, illustratively using patterned layers of light absorbing material to produce different types of filters. The implementation in FIG. 14 could, for example, be implemented by printing or otherwise depositing and patterning layers of material as described above.

In the cross section at the top of FIG. 14, filter assembly 700 includes red layer part 720, black layer part 722 overlapping layer part 720, gray layer part 724, green layer part 726, and blue layer part 728 overlapping layer part 726. Where overlaps occur, the result is the intersection of two absorption filters: the intersection of layer parts 720 and 722 is a closed filter, while the intersection of layer parts 726 and 728 is a filter with a band that is the intersection of the bands of the green and blue filters.

The three graphs below the cross section show expected intensity signals similar to those in the graphs in FIG. 11. Curve 730 would be for a red fluorescing particle or tag; curve 732 would be for a green fluorescing particle or tag; and curve 734 would be for an example where object 640 is tagged both with a red and a green fluorescing particle so that curve 734 is a scaled sum of curves 730 and 732. More generally, the technique of FIGS. 13 and 14 would make it possible to distinguish not only red, green, and blue particles and tags, but also objects tagged with combinations such as red and green, green and blue, red and blue, and red and green and blue. Each combination results in a distinguishable time varying signal that can be analyzed to obtain information about the color or colors that are emanating.

Although the intensity signals described above in relation to FIGS. 11 and 14 could be obtained from sensing results of a single, large area photosensor, it would also be possible to use an IC with an array of photosensing cells or an array of discrete photosensors, in either case appropriately positioned along a path traveled by objects past one or more filter assemblies. If an array is used, and each element of the array is covered with a different filter assembly, it may be possible to distinguish many different types of particles concurrently. The number of particles to be distinguished can be much larger than the number of elements in the array, since each measurable distinguishing feature can provide one axis in a principal component analysis, and multiple particles can be distinguished along each such axis. Additional techniques that can be used to track and distinguish objects are described in U.S. Pat. No. 7,817,276, incorporated herein by reference in its entirety. Objects can be distinguished, for example, from their environment or background or from objects of other types; an operation "distinguishes" objects if the operation locates, selects, sorts, counts, or otherwise identifies an object or controls or directs an object according to type or separates objects or otherwise treats objects differently in some way.

Band pass filters of other types can also be used to implement filter assemblies as described in some of the exemplary implementations herein. For example, interference based filters can have different bands similar to the bands described above in relation to FIGS. 9-14.

Figure 15:
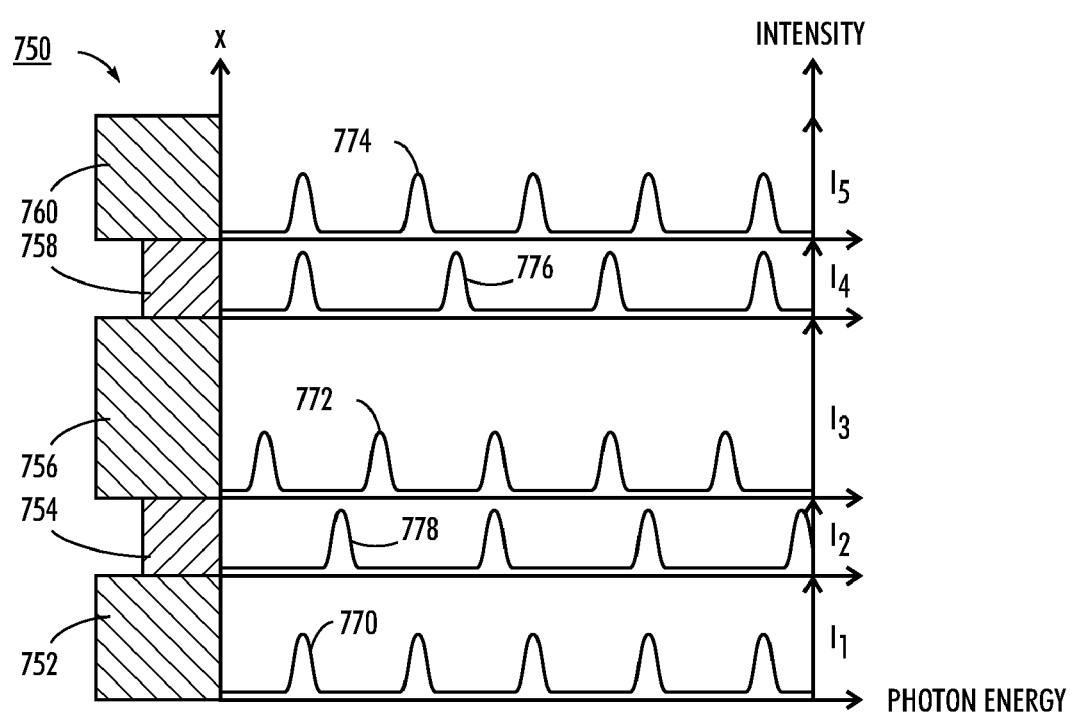
FIG. 15 is a cross-sectional view of another implementation of a filter arrangement that can be included in an encoding component as in FIG. 2, together with graphs showing spectra of transmitted intensities.

Filter assembly 750 in FIG. 15 illustrates an implementation in which a thin layer of transparent material creates Fabry-Perot oscillations, and can be structured to obtain high thickness-dependent index contrast. Assembly 750 includes filters 752, 754, 756, 758, and 760, each of which has substantially constant thickness, but with the thicknesses of filters 752, 756, and 760 being approximately equal to each other while the thicknesses of filters 754 and 758 are approximately equal to each other but smaller. Assembly 750 could be produced, for example, by etching a deposited layer of transparent material or by imprinting a non-solid layer of such material before it solidifies.

To the right of the cross section of assembly 750 is a graph showing an intensity-energy function of its transmitted light. In other words, curves 770, 772, and 774 are approximately the same because filters 752, 756, and 760 have approximately the same thickness. On the other hand, curves 774 and 776 are also similar to each other but different than the others, because the thicknesses of filters 754 and 758 are the same as each other but different than the others. As a result, an object traveling along a path past assembly 750 results in a time-varying signal with changing intensity-energy function. The total transmission at each position will relate to the overlap of the cavity's transmission lines and the particle spectrum. The other part of the emanating light would be reflected from assembly 750, and could also be detected to obtain confirming information. For example, assembly 750 could be on one cover slide of a channel, and two photosensors (not shown) could be positioned, one on the side of assembly 750 away from the channel and the other on the opposite side of the channel to obtain sensing results for the reflected emanating light.

Figure 16:
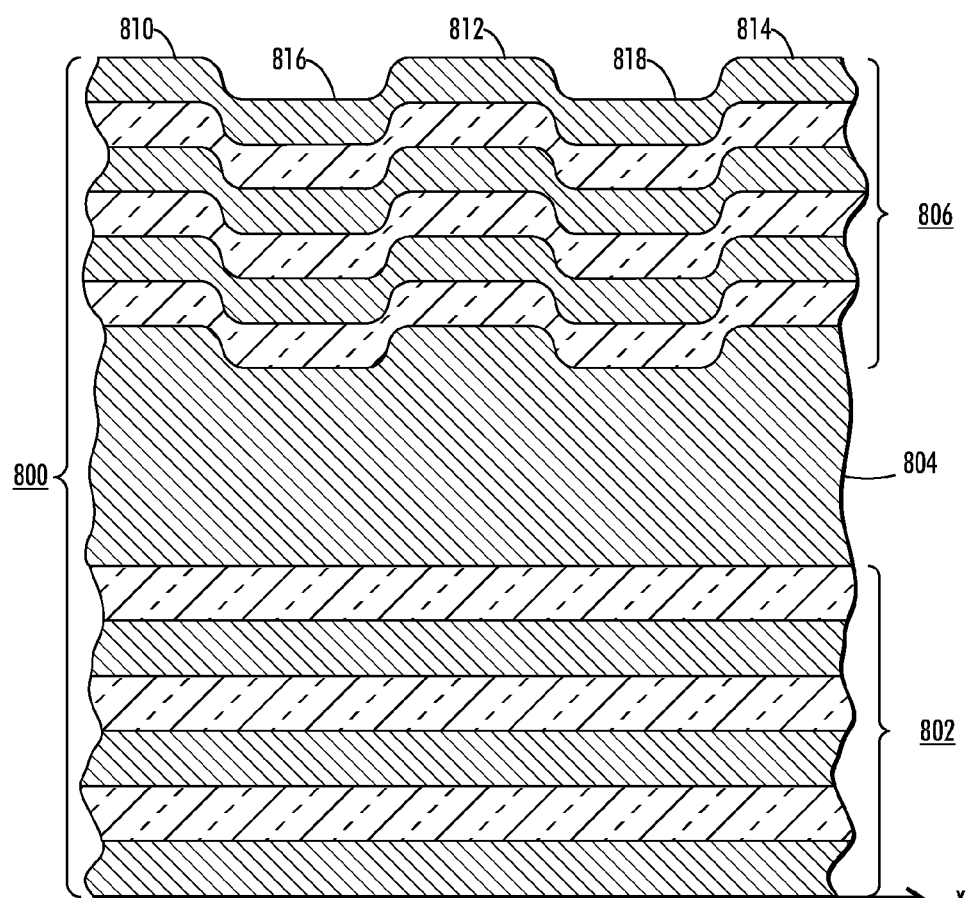
FIG. 16 is a cross-sectional view of yet another implementation of a filter assembly that can be included in an encoding component as in FIG. 2.
Figure 17:
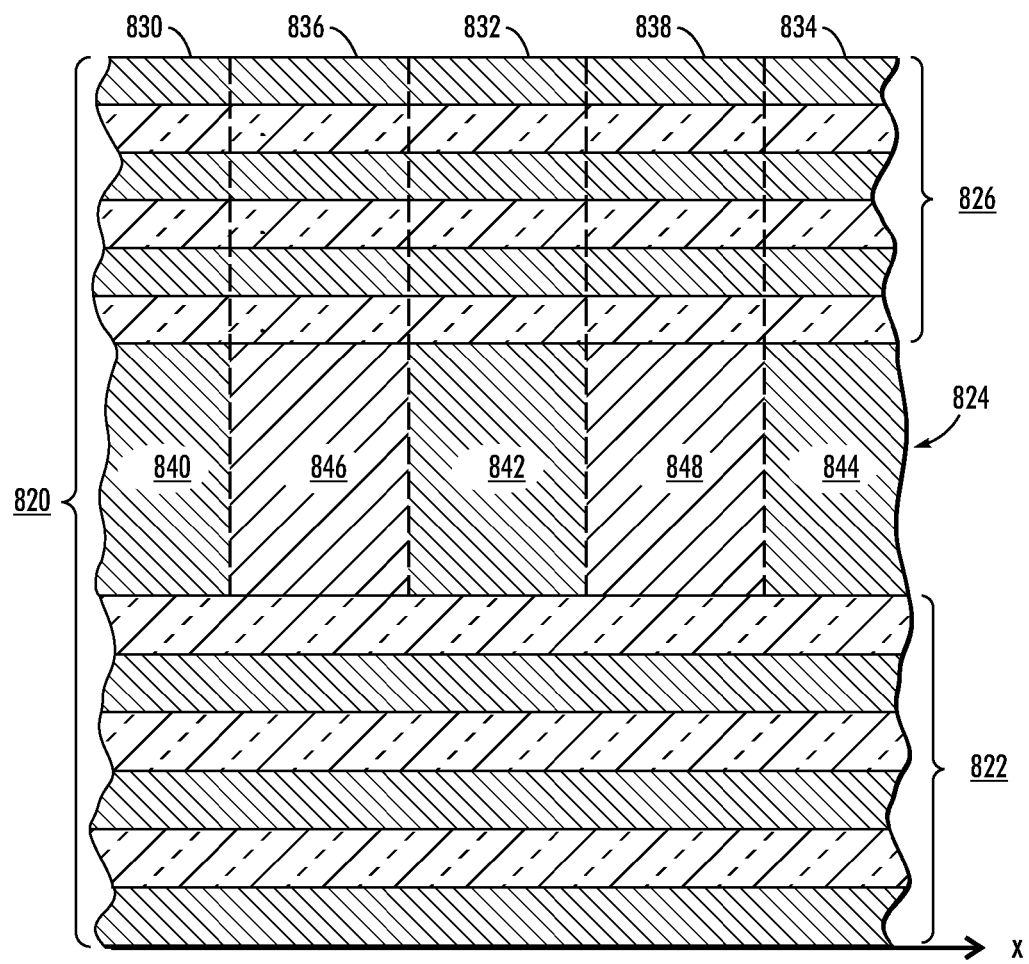
FIG. 17 is a cross-sectional view of yet another implementation of a filter assembly that can be included in an encoding component as in FIG. 2.

FIGS. 16 and 17 illustrate two ways in which Fabry-Perot interference-based filters could be structured to obtain band pass filters more nearly similar to those of FIGS. 9-12. In each implementation, optical thickness of the filter's cavity varies in the x-direction, but the variation in optical thickness is produced in two different ways. The general strategy in FIGS. 16 and 17 is to provide regions that operate as band pass Fabry-Perot filters, with different sets of filters having transmission peaks at different photon energies. For example, one set of filters could have a transmission peak at approximately 822 nm, while another could have a transmission peak at approximately 833 nm, and the two sets could have a periodic pattern as shown or any other appropriate pattern.

Filter assembly 800 in FIG. 16 includes homogeneous bottom distributed Bragg mirror (DBR) 802, cavity 804, and upper DBR 806. Such a filter assembly could be produced by using techniques described in U.S. Pat. No. 7,315,667, entitled "Propagating Light to be Sensed", incorporated herein by reference in its entirety. As can be see in FIG. 16, however, the optical thickness of cavity 804 has been modified by changing between two thicknesses, one larger and one smaller, so that assembly 800 effectively includes two sets of filters: reference numerals 810, 812, and 814 indicate three filters with the larger thickness while regions 816 and 818 are filters with the smaller thickness, therefore transmitting a shorter wavelength than the filters in regions 810, 812, and 814. The variations in thickness of cavity 804 can be produced, for example, by etching the layer in which cavity 804 is formed after it is deposited and before the series of layers in DBR 806 are deposited. Alternatively, a half-tone mask could be used during growth of cavity 804.

Filter assembly 820 in FIG. 17 similarly includes lower DBR 822, cavity 824, and upper DBR 826, each of which illustratively has approximately uniform thickness, but with cavity 824 having optical thickness that varies in the x-direction. As a result, regions 830, 832, and 834 transmit a different photon energy than regions 836 and 838. More specifically, the refractive index of cavity regions 840, 842, and 844 is different than the refractive index of regions 846 and 848. Differences in refractive index could be produced in a wide variety of ways. Implantation or ion diffusion (as in ion exchange) could be performed as is done in fabricating waveguides for integrated optics; another approach would be implantation-induced intermixing of multiple quantum well (MQW) structures as in laser diode fabrication; further, ultraviolet light-induced changes in refractive index could be used as with germanium-doped glass used in fabricating fiber Bragg gratings (FBG) in glass fibers; in principle, any technique that can modify refractive index by implantation, heat, light, or other operation could be used.

Figure 18:
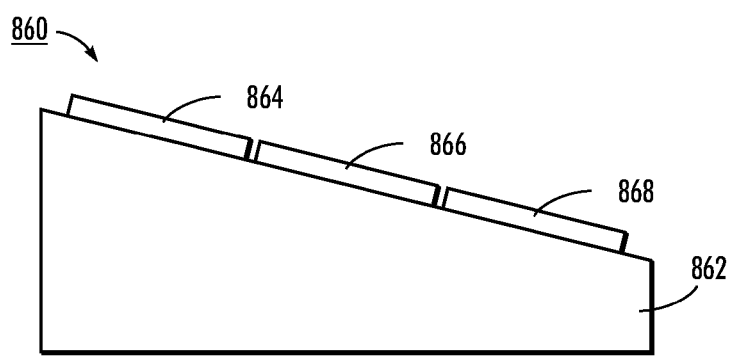
FIG. 18 is a cross-sectional view of yet another implementation of a filter assembly that can be included in an encoding component as in FIG. 2, such as with features as in any of FIGS. 15-17.

FIG. 18 illustrates an additional technique that could be used together with the technique of FIG. 15 and possibly the techniques of FIGS. 16 and 17. Filter component 860 includes a wedge-shaped layer of transparent material as in FIG. 15 or Fabry-Perot filter as in FIGS. 16 and 17, but with filter assemblies 864, 866, and 868 formed at its upper surface such as by techniques described in relation to FIG. 15, 16, or 17. In other words, in addition to having filters of the types described above, there is also a continuously varying thickness across component 860 so that, in addition to the time-varying effects of each filter assembly, additional spectral information is contained in the encoded emanating light, and can be obtained by appropriate processing. With techniques such as this, it may be possible to measure the entire spectrum with a loss of not more than 50% (assuming full modulation) of the light, which would be advantageous in comparison with conventional linear variable filter approaches.

In implementations as in FIGS. 9-12, laminar flow can be used to provide substantially uniform object speed past a filter arrangement. In contrast, FIGS. 19-21 illustrate examples in which laminar flow can produce non-uniform displacement or can be modified in other ways.

Figure 19:
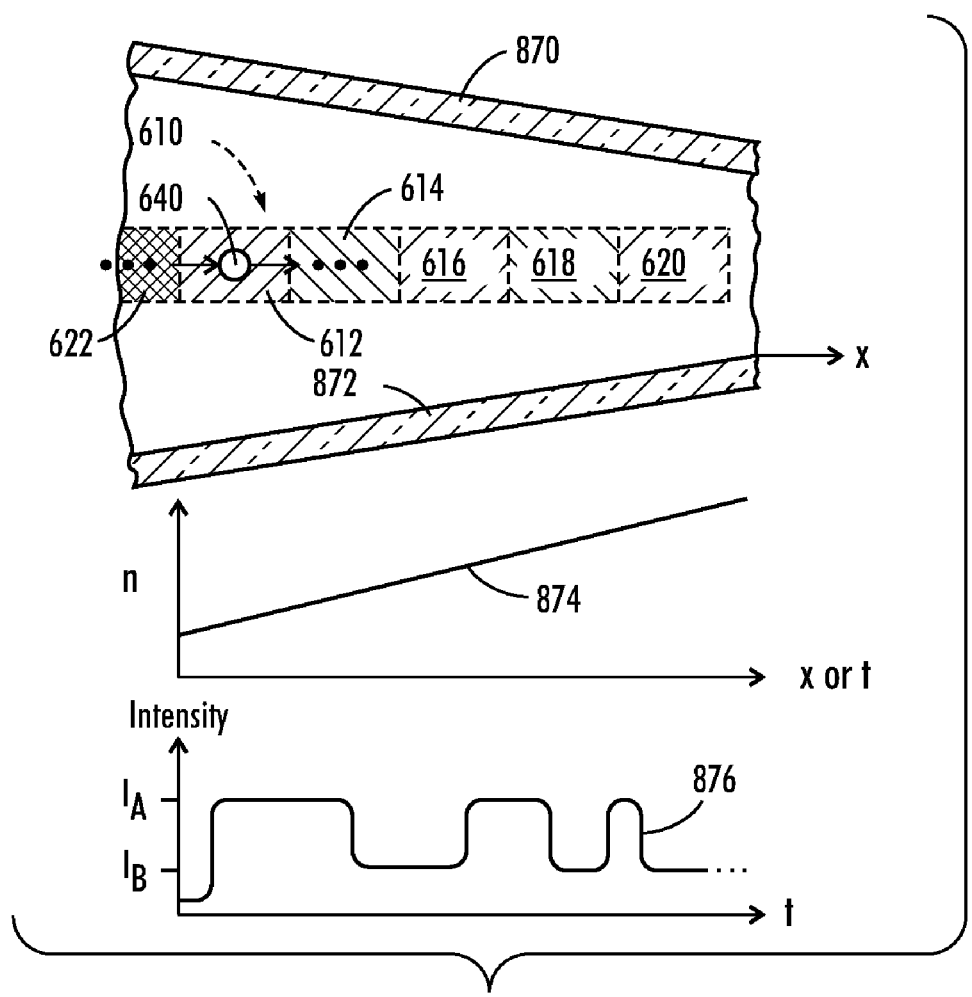
FIG. 19 is another partially schematic cross-sectional view showing a displacement control arrangement that includes shaped boundaries, together with graphs showing velocity of an object and also showing intensity of emanating light as a function of time.

FIG. 19, taken along a line similar to line 19-19 in FIG. 12, shows wall-like parts 870 and 872 with linearly decreasing distance between them. As a result, as object 640 passes along two-color filter assembly 610 (with filter elements 612, 614, 616, 618, and 620 illustratively periodic rather than random as in FIG. 12), its velocity increases linearly as indicated by curve 874, either as a function of position or of time. Therefore, rather than a periodic time-varying signal, the resulting time-varying signal is chirped, meaning that the periods decrease linearly due to change in velocity of object 640 due to change in the flow speed of fluid in the channel resulting from the changing channel dimensions. Curve 874 illustrates the resulting chirped signal, which has intensity I(A) during regions 612, 616, and 620, and intensity I(B) during regions 614 and 618. As can be seen, the duration of the signal during each successive region is shorter than the preceding region, resulting in the chirped pattern. For the sake of illustration, the linear decrease in transition time is exaggerated in curve 874 in comparison to the narrowing of the channel.

The technique in FIG. 19 is only one of a variety of ways of producing a chirped time-varying signal, and various other techniques could be used. For example, more complex flow speed distributions could be obtained by modifying the channel walls in other ways or by providing devices that change the flow speed or flow pattern within the channel, any of which would produce more complex time-varying signals from different objects.

Figure 20:
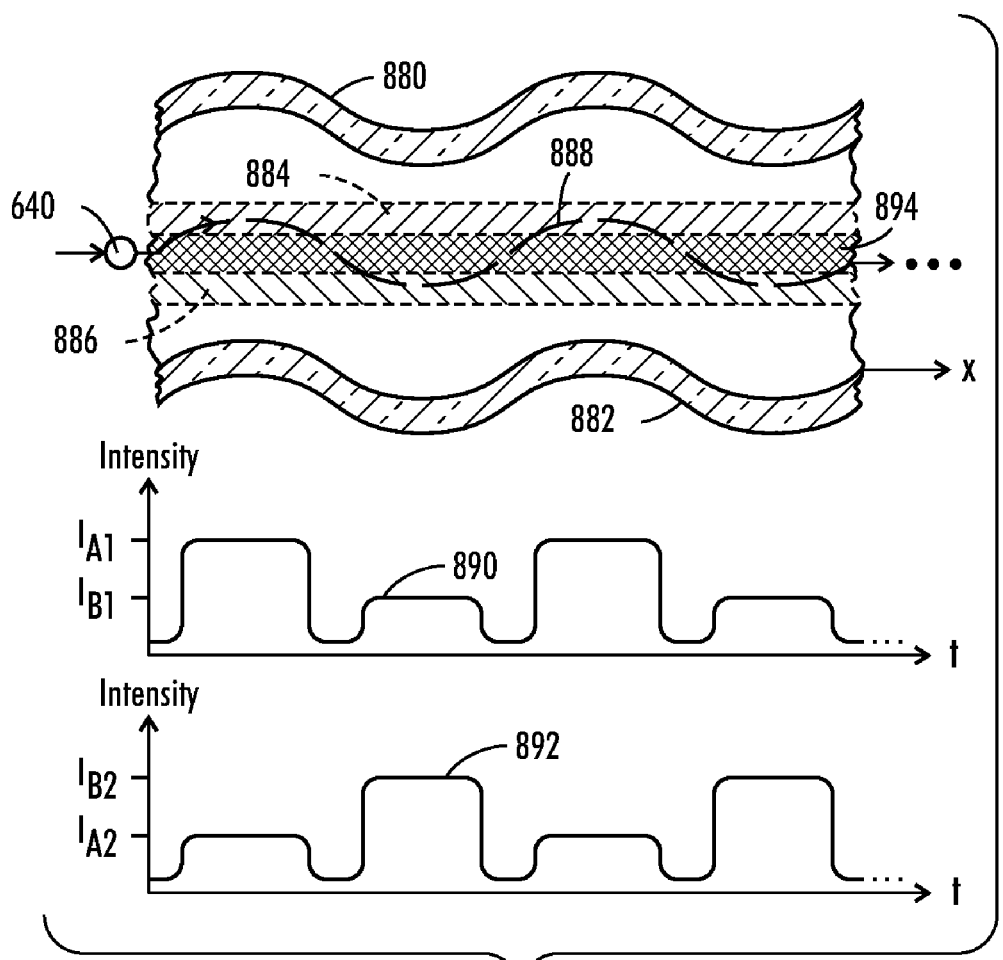
FIG. 20 is a cross-sectional view of another displacement control arrangement that can be included in an encoding component as in FIG. 2, together with graphs showing intensity of emanating light for exemplary types of objects.
Figure 21:
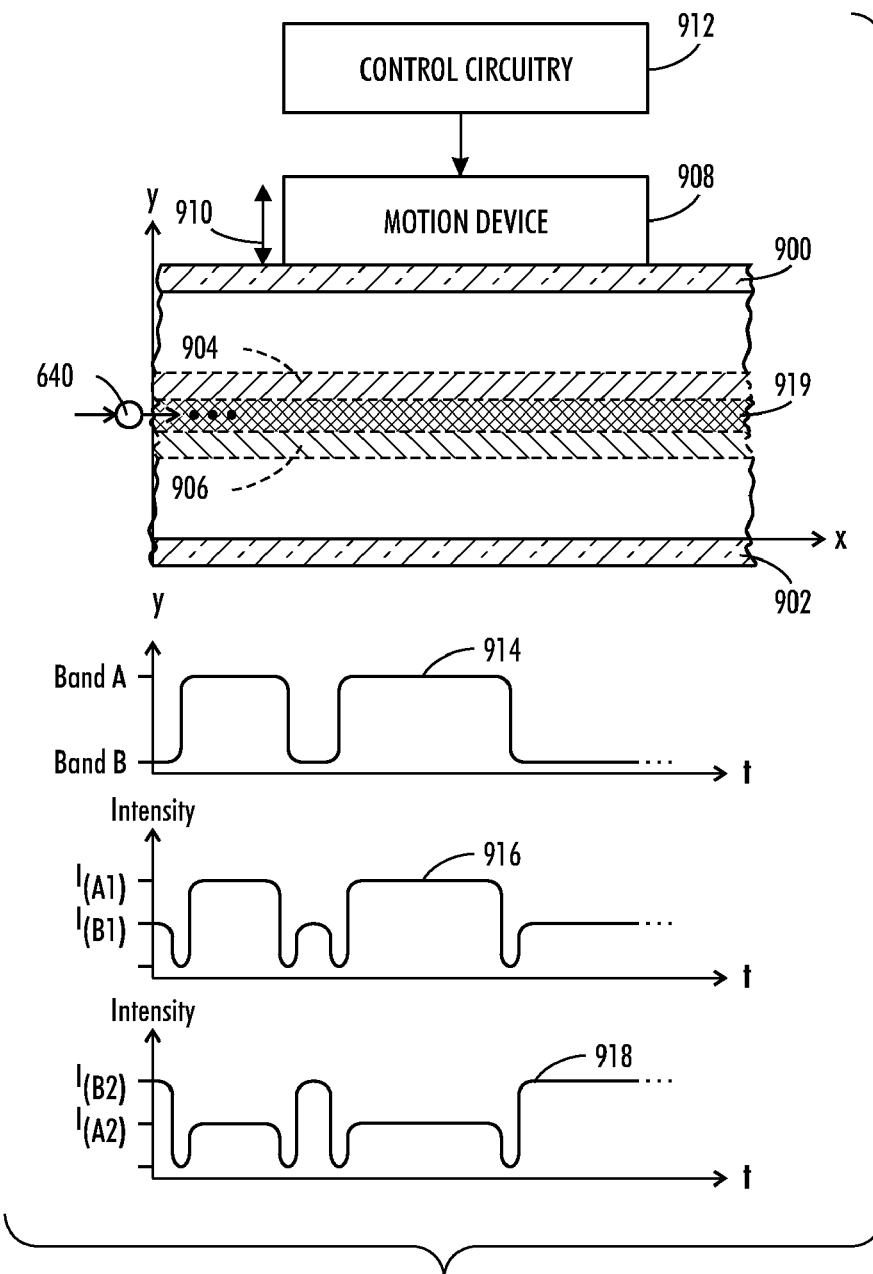
FIG. 21 is a partially schematic cross-sectional view of another displacement control arrangement that can be included in an encoding component as in FIG. 2, together with a graph showing displacement as a function of time and graphs showing intensity of emanating light as a function of time for exemplary types of objects.

FIG. 20 illustrates, on the other hand, how relatively simple time-varying signals could be produced using more complicated techniques. In general, such techniques assume that geometry of a channel directs flow of object 640 in a defined manner such as periodic, chirped, or random, past a sequence of filter elements. This allows redirection of particle flow past a simpler filter assembly geometry, and may be advantageous in cases where it is easier to redirect particle flow to produce a desired time-variation of emanating light than it would be to produce a filter assembly to produce the same time variation; for example, it might be easier to change channel wall shapes than to produce a desired filter assembly. In other cases, on the other hand, it might be advantageous to obtain more abrupt or rapid signal transitions with a well-defined filter assembly. In addition to the techniques described below, which involve shaping or moving walls, an object's flow within a channel could also be redirected by other techniques; an electrically charged object such as a particle, for example, could be redirected by electrical field variations. In general, however, the Reynolds number in typical microfluidic and nanofluidic implementations are so small that laminar flow conditions are, as a practical matter, always present.

In the example in FIG. 20, wall-like parts 880 and 882 are parallel but each of them is shaped like a sinusoidal wave, resulting in a sinusoidal flow pattern in the channel between them. Filter elements 884 and 886 are homogeneous of two different colors, illustratively labeled "A" and "B". As object 640 follows sinusoidal path 888, it moves back and forth between elements 884 and 886, passing through a small gap between them twice during each period. Curves 890 and 892 illustrate exemplary time-varying signals that could result from an object traveling along path 888. Curve 890 illustrates an example of an object of a type with a spectrum similar to color A but different from color B, while curve 862 illustrates an example of an object of a type with a spectrum similar to color B and different from color A. As a result, the curves are somewhat complementary, although each curve goes to approximately 0 while path 888 is crossing stripe 894 of blocking material between elements 884 and 886. Blocking material could also be provided outside elements 884 and 886.

Wall-like parts 900 and 902 in FIG. 21 are substantially straight and parallel, with filter elements 904 and 906 between them, similar to elements 884 and 886 in FIG. 21. Motion device 908 produces relative movement between the path of object 640 and stripe-like elements 904 and 906, as indicated by bi-directional arrow 910. Control circuitry 912 provides signals to control operation of motion device 908, which need not be periodic, but could take any appropriate pattern, resulting in arbitrary time-varying signals with features indicating different types of objects. An alternative would be to move elements 904 and 906; more generally, any combination of relative movements between walls 900 and 902 on the one hand and elements 904 and 906 on the other could produce movement as indicated by bi-directional arrow 910. Furthermore, additional variations could be produced by changing fluid flow within the channel so that the speed or other displacement of object 640 changes as a function of time relative to the other movements. Motion device 908 could be set up to produce variations in response to trigger signals indicating incoming objects.

Curve 914 illustrates movement of object 640 between element 904, labeled "Band A", and element 906, labeled "Band B". As illustrated, object 640 spends different lengths of time in each region and can spend a random amount of time in each region, resulting in a random excitation pattern. Curves 916 and 918 illustrate exemplary time-varying signals that could be produced by the technique of FIG. 21. One type of object has a spectrum more similar to color A of element 904, as illustrated by curve 916, while the other has a spectrum more similar to color B of element 906, as illustrated by curve 918. As each object travels between elements 904 and 906, it passes over stripe 919 of blocking material between them, resulting in a brief interruption of the emanating light, so that each curve goes briefly to 0. In curve 916, the intensity along element 904 is I(A1), while the intensity along element 906 is I(B1), a lower value linearly. Conversely, curve 918 illustrates that the intensity is higher along element 906, at intensity I(B2), and lower along element 904, at intensity I(A2). The two curves are, in general, complementary, except for times when they are passing stripe 919 between element 904 and 906; object 640 can be moved instantaneously between Band A and Band B, moving very quickly across stripe 919, so that the time in which it is passing stripe 919 are very brief.

Figure 22:
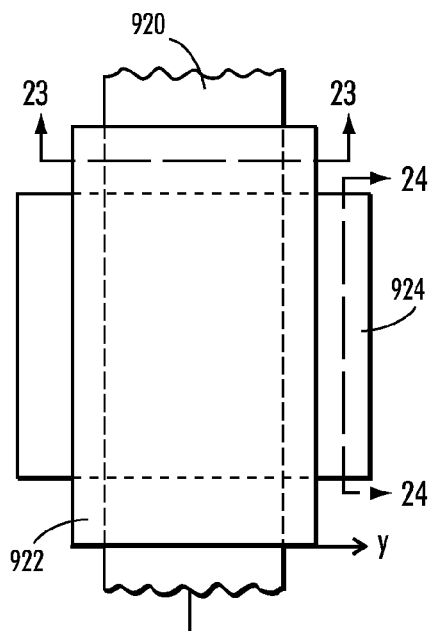
FIG. 22 is a top view of an implementation of a fluidic channel with an encoding arrangement that can be included in an implementation with features as in FIG. 1.
Figure 23:
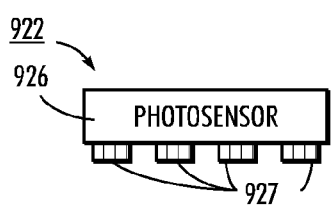
FIG. 23 is a cross-sectional view of a component in FIG. 22, taken along the line 23-23.
Figure 24:
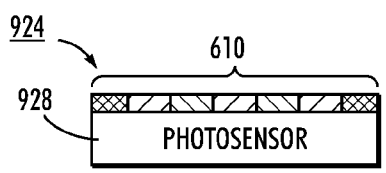
FIG. 24 is a cross-sectional view of another component in FIG. 22, taken along the line 24-24.

FIGS. 22-24 illustrate implementations of filter arrangements in which filter assemblies are on opposite sides of channel 920. In the illustrated implementation, detector 922, shown on the near side of channel 920, includes one filter assembly, while detector 924, on the far side of channel 920, includes another filter assembly. Although each detector could be implemented in a wide variety of different ways, to obtain information about emanating light and objects from which light emanates, FIGS. 23 and 24 illustrate an example in which detector 922 includes a periodic filter assembly with periodicity in a direction transverse to channel 920, labeled the y-direction, and detector 924 includes a random two-color filter assembly with a longitudinal sequence in the x-direction, though other angles between the x- and y-directions might also be useful including, in some cases, implementations in which they are parallel. In the illustrated case, sensing results from detector 922 include signals modulated in the y-direction, while sensing results from detector 924 indicate signals modulated in the x-direction. The two modulations can be used to obtain information about an object from which light is emanating.

As shown in FIG. 23, detector 922 can be implemented with photosensor 926 on a photosensitive surface of which are filters 927, periodic in the y-direction; each of filters 927 is illustratively a red band pass filter, but they could instead be any other color or closed filters or intermediate intensity gray scale filters, and could be implemented with absorption, reflection, or interference-based filtering techniques as described above. Similarly, FIG. 24 shows an implementation of detector 924 in which photosensor 928 has filter assembly 610 (FIG. 9) on its photosensitive surface; photosensor 928 could also have a periodic filter superimposed on filter assembly 624 or in place of filter assembly 624, in which case it might include green filters (not shown).

A wide variety of other arrangements similar to FIGS. 22-24 would be possible, including, for example, another type of template layer on one side of channel 920 to provide a desired signal as described in U.S. Pat. No. 7,817,254, incorporated herein by reference in its entirety, and a periodic mask layer to provide a periodic signal on the other side of channel 920; in this implementation, the periodic signal could be constantly analyzed to obtain values indicating displacement of an object currently flowing through channel 920, which could be used to determine an appropriate time scale for correlation with the template signal similar to techniques described. In another possible variation, emanating light from fluorescence could be photosensed on one side of channel 920 and emanating light due to scattering, for example, could be photosensed on the other side.

Some of the exemplary implementations described below involve filter assemblies that combine periodic signals additively with template signals from filter sequences similar to some of those described above. The resulting time-varying signal emerges from the filter assembly with two different spatially varying patterns imposed on it. To produce such a signal, for example, a radial sequence or "stack" of filters similar to that shown in FIG. 4 could be used. Within a stack of filters, for example, one layer could be a template layer with an appropriate pattern to produce the template signal, while another layer could be a periodic layer with an appropriate pattern to produce the periodic signal; each of the template layer and periodic layer could have rectangles or other closed polygons of zero opacity surrounded by regions with opacity 0.5.

Figure 25:
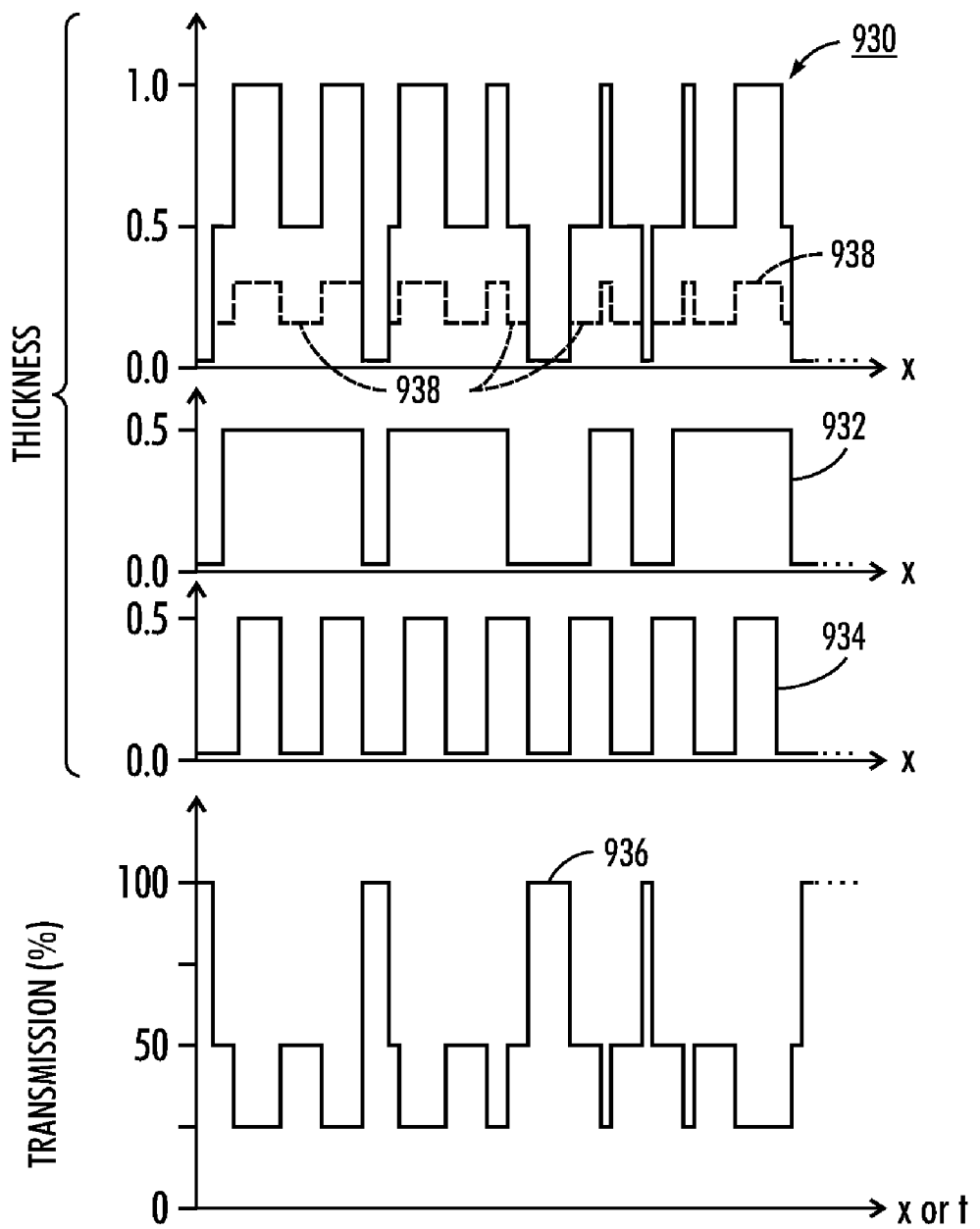
FIG. 25 includes a set of graphs showing cross-sectional thickness as a function of position in an x-direction for filters and showing transmission as a function of position in the x-direction or as a function of time t for one of the filters.
Figure 26:
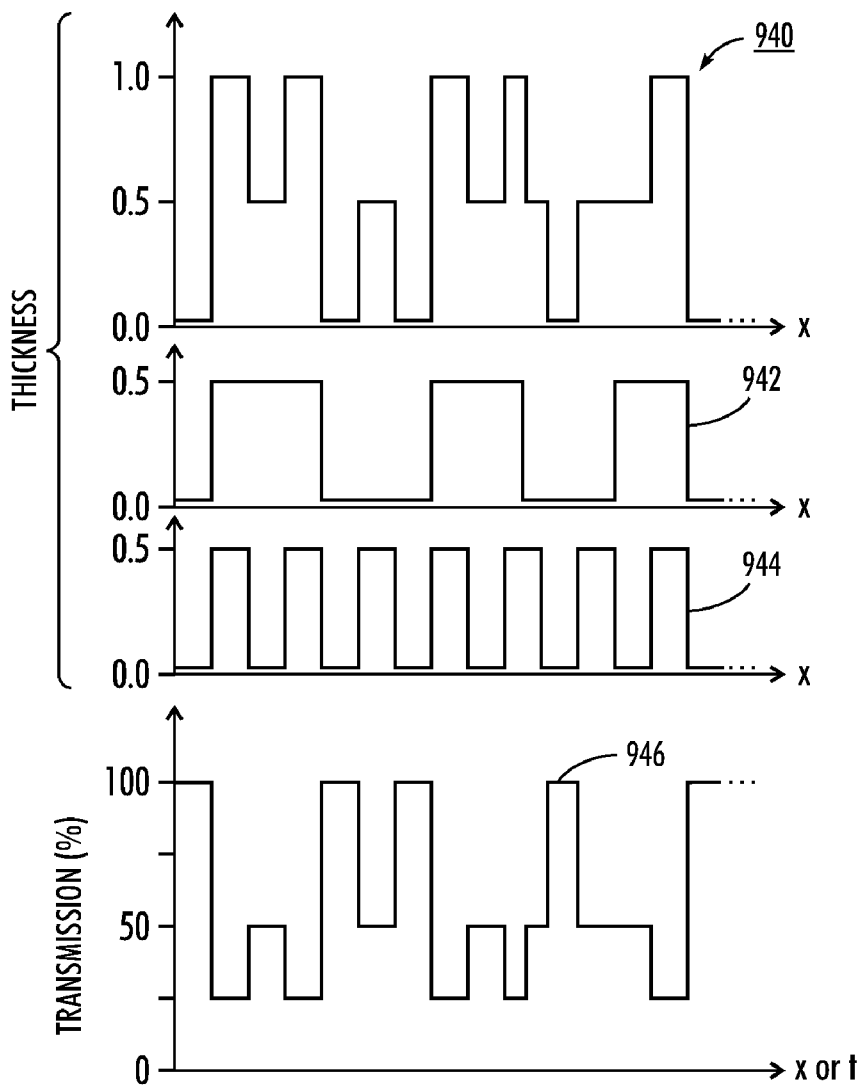
FIG. 26 includes a set of graphs showing cross-sectional thickness as a function of position in an x-direction for other filters and showing transmission as a function of position in the x-direction or as a function of time t for one of the filters.

FIGS. 25 and 26 illustrate an alternative approach that can be used with reflective gray scale filters, producing a single filter assembly equivalent to a desired radial sequence or stack of filters. To obtain filters as in FIGS. 25 and 26, thickness definitions of two filter layers can be overlaid using software tools and the thicknesses of overlapping regions can be added, resulting in regions with thicknesses of 0, 0.5, and 1 in the example given above; the two filter layers could both be oriented with variation in the same direction as in FIGS. 25 and 26, similar to the techniques of FIGS. 9 and 13, or could be oriented with variation in different directions, e.g. orthogonal to each other. For implementations in which layer thickness does not appropriately define or determine the desired equivalent filter's structure or its optical variation, the techniques in FIGS. 25 and 26 could be modified to first overlay optical feature definitions of the filters in which regions have defined optical feature values that determine the desired variation, thus obtaining an optical feature definition of the desired equivalent filter; the optical feature definition could then be converted to a layout-type description of the equivalent filter in which each region has a defined optical thickness or other characteristic that can be produced to provide the region's value for the optical feature.

The techniques of FIG. 25-26 take advantage of the fact that, in general, superpositions of filters are commutative, in the sense that the resulting transmission or reflection function is the same regardless of the order in which filters are superimposed. There are, of course, exceptions, such as where interference effects can occur if filters are in a specific order, or where alignment or other relationship of filter features can result in loss of different information depending on the order of the filters.

If the equivalent filter definition is a thickness definition to produce a purely transmissive/reflective filter with no color variation, and if partial etching can be performed, an equivalent filter that approximates the equivalent filter definition can be constructed by first depositing a highly reflective material, such as chromium, over the entire filter assembly, and by then partially etching the reflective material away in regions with thickness 0 or 0.5 to an appropriate extent, leaving a thin, partially transmitting layer, after which the remaining reflective material can be etched away in regions with thickness of 0. Where partial etching is unreliable, other techniques may be used, such as by techniques that deposit a first patterned layer of thickness 0.5 with any suitable patterning technique, then depositing over it a second patterned layer of thickness 0.5 that is patterned without etching, such as with liftoff or other patterning techniques that do not require etching. Furthermore, similar techniques might be applied to produce layered filter structures that include DBRs of varying transmission/reflectivity and/or cavities of varying optical thickness, such as those described above in relation to FIGS. 16-18; variation in cavity thickness could result from any appropriate combination of thickness variation and refractive index variation, produced with any appropriate techniques.

Filter 930 in FIG. 25 is equivalent to the combination of a random filter and a periodic filter, superimposed one on the other. Curve 932 shows the shape of the random filter, while curve 934 shows the shape of the periodic filter; as can be seen, the random and periodic filters both have only two thickness levels, either 0 or 0.5, but filter assembly 930 has three thickness levels, corresponding to 0, 0.5, and 1. Curve 936 shows a resulting transmission function. Emanating light passing through filter assembly 930 includes both displacement and position information about an object from which it emanates, and allows time-scaling techniques to extract that information, as described below.

The technique illustrated in FIG. 25 can be adjusted as suggested by dashed lines 938 within filter 930. In other words, total light output can be changed by scaling the amplitude of the thickness levels: rather than 0, 0.5, and 1, for example, thickness levels of 0, 0.2, and 0.4 could be used, allowing greater light transmission. It may be necessary, however, to make a tradeoff between greater light output, and therefore total signal intensity, on the one hand, and greater light modulation on the other—greater light modulation may facilitate calculation of displacement and position within a given observation region. The mask suggested by dashed lines 938 emphasizes total light output because it has reduced thickness and, conversely, increased transmission, with a thickness of 0 being equivalent to transmission of 1 and vice versa. The scaling suggested by dashed lines 938 may require great precision: the x-direction scale of features in assembly 900 may be as great as 10 µm, while a useful thickness may be as thin as 10 nm of chromium.

Similarly, filter assembly 940 in FIG. 26 is equivalent to the combination of a chirp filter represented by curve 942 and a periodic filter represented by curve 944. A combination of chirp and periodic filters can make it possible to more efficiently extract displacement and position information about objects that may have different speeds. Curve 946 shows a resulting transmission function, which allows information extraction.

A stack-equivalent filter assembly as in FIGS. 25 and 26 can in some cases have a smaller MFS than either of the simpler non-uniform filters. As mentioned above, loss of resolution can occur for light emanating from objects approximately as large as the MFS.

Figure 27:
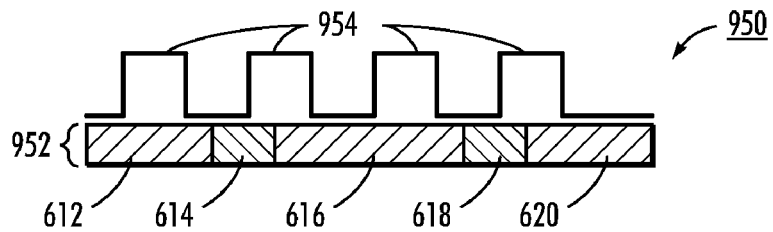
FIG. 27 is a schematic cross-sectional view of a filter assembly that includes two simpler filters.

FIG. 27 illustrates one way in which a longitudinal sequence of filters, such as a random band pass filter arrangement as described above in relation to FIGS. 9-12 can be combined with a reflective gray scale filter arrangement, illustratively a periodic gray scale filter. Filter arrangement 950 in FIG. 27 includes filter subassembly 952 with a longitudinal sequence similar to that described above in relation to FIGS. 9-12. On the upper surface of subassembly 952 is a periodic filter subassembly with regions 954, each having an intermediate transmission level such as 0.5. As a result, filter assembly 950 combines the technique of FIG. 25 with that of FIG. 12, providing distinguishable time-varying signals for emanating light of different colors, and also modulating the emanating light to allow time-scaling techniques as described below. In effect, the time-scaling operations can be performed in the same way for each emanating color's signal, and the different color signals can be used to distinguish types of objects after time scaling.

Figure 28:
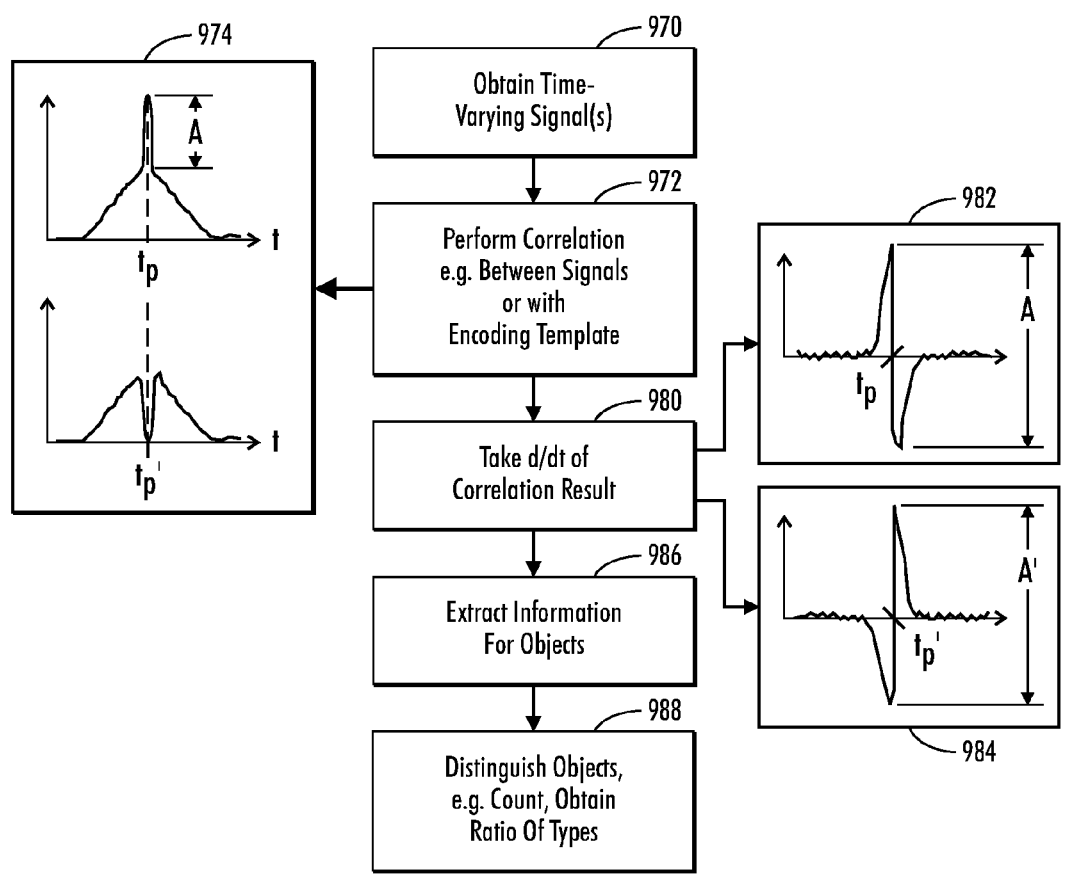
FIG. 28 is a flow chart with graphs illustrating an implementation in which information about objects is obtained from sensed time-varying signals.

The flow chart in FIG. 28 illustrates ways in which information about objects can be obtained and used by CPU 402 (FIG. 6); the technique of FIG. 28 illustratively extracts information such as a type, a position, or a spectral difference, and uses such information to distinguish objects. FIG. 28 also suggests ways in which routines 440, 442, and 444 (FIGS. 6 and 7) could be implemented. Although suitable for CPU 402, operations in FIG. 28 could be implemented with a wide variety of different types of circuitry with or without a CPU. Furthermore, although described in terms of time-varying signals from photosensors, the technique of FIG. 28 could be applied to any time-varying sensed signals, including, for example, capacitively sensed signals from charged particles with encoded information due to shapes, sizes, and positions of electrodes.

The operation in box 970 obtains one or more encoded time-varying signals from a photosensor arrangement as one or more objects travel along respective paths past a filter arrangement. The technique could be implemented with a single photosensor along the paths, but it might also be possible to implement with two photosensors on opposite sides of the paths or with other photosensor arrangements. The objects can, for example, travel through a channel as described above in relation to FIGS. 8-12 and 19-21 and the time-varying signals can be encoded in any of a wide variety of ways using filter arrangements, including one or more of those described above, with or without displacement control and/or spatially modulated excitation; excitation techniques that could be used are described in U.S. Pat. No. 7,763,856, also incorporated herein by reference in its entirety. For example, if one of the filter arrangements is at least partially non-periodic or if displacement control or excitation is at least partially non-periodic, a respective template of the resulting non-periodic pattern for each of a number of types of objects can be used to perform a correlation operation; in other implementations, two differently encoded time-varying signals can be obtained in box 970 and correlated with each other. Note, however, that two types could be distinguished based on a single template, especially if their time-varying signals are sufficiently complementary that one results in correlation and the other in anti-correlation with the template.

The operation in box 970 can include providing any appropriate control signals to other components of the system, including signals to read out sensing results of photosensors. The control signals could be implemented as in routines 440 and 442 (FIG. 6), with CPU 402 providing signals through device I/O 420 to one or more of devices 422 through 424. For example, fluid flow speed could be adjusted and channel wall movement could be controlled as described above in relation to FIG. 21. In order to obtain the time-varying signals, CPU 402 could provide signals through IC I/O 410 to obtain photosensed quantities from ICs 412 through 414.

The operation in box 972 performs a correlation or other comparing operation on one or more time-varying signals from box 970, such as comparing two encoded signals with each other or comparing one encoded signal with a respective template of a non-periodic encoding pattern for each distinguishable type of object. As used herein, the term "correlation operation" encompasses any of a variety of mathematical operations that can be performed on a pair of time-varying functions, with or without scaling, and that obtains a similarity measure as a function of time-alignment. This correlation operation can be implemented, for example, as described in Patent Application Publication US 2008/0183418, incorporated herein by reference in its entirety. Additional correlation and other comparison techniques that could be used are described in U.S. Pat. No. 7,817,254 also incorporated herein by reference in its entirety.

A correlation operation in box 972 can produce correlation results for each pair of waveforms that is compared. For example, if box 972 compares an encoded time-varying signal from box 970 with each of N templates for N types of objects, N correlation results are produced.

The graphed curves in box 974 illustrate two types of correlation results: The upper curve illustrates a correlation result where two time-varying waveforms are correlated, i.e. highly similar at the time alignment designated $t_p$; the lower curve illustrates a correlation result where two time-varying waveforms are anti-correlated, i.e. highly dissimilar at the time alignment designated $t_p'$. In each case there is a peak, with the peak in the correlated case marked to show its amplitude A and with the anti-correlated case having an inverted peak of similar amplitude. If correlation is performed on a continuous basis, correlation results could similarly be continuously obtained for each template with which comparison is made, with each object's travel past the filter arrangement producing a peak, an inverted peak, or a feature in between the two for each template.

The operation in box 980 obtains a time-varying waveform that equals or approximates the time derivative d/dt of each correlation result from box 972. For the correlated case, a derivative waveform like the graphed curve in box 982 is obtained, with a positive peak followed by a negative peak, with a zero crossing at $t_p$, and with the contrast or differential quantity between the peaks again being the amplitude A. For the anti-correlated case, a derivative waveform like the graphed curve in box 984 is obtained, with a negative peak followed by a positive peak, with a zero crossing at $t_p'$, and with the contrast or differential quantity between the peaks being amplitude A', the amplitude of the inverted peak in the lower graph in box 974. The amplitudes obtained in this manner are, in general, free of offsets, allowing direct comparison to obtain spectral information.

The operation in box 986 uses derivative waveforms from box 980 to extract information for objects passing the photosensor. The extracted information could, for example, be a type based on whether an object resulted in correlation, anti-correlation, or neither with a given template; position based on the time at which a zero crossing occurs in correlation or anti-correlation; and spectral difference, e.g. a difference of emission, absorption, or scattering spectrum, based on the amplitude or contrast between positive and negative peaks from correlation and anti-correlation, respectively. Features of a derivative waveform could be found and measured using various techniques. The operation in box 988 can then be performed to distinguish objects using information extracted in box 986, such as by obtaining counts of different types of objects or ratios between such counts, or with other operations as described above in relation to FIG. 7.

The operations in boxes 972, 980, and 986 could be implemented, for example, as parts of one or both of routines 442 and 444 (FIG. 6). The operation in box 988 could be implemented as part of routine 444. In general, these operations could be implemented to handle signals from each object separately or to handle a signal received concurrently or in series from a number of objects, in which case minimum differences, such as in positions or speeds, may be necessary to allow separation of signals from different objects. Any appropriate combination of serial and parallel operations could be implemented in any appropriate circuitry. Data streams or other data structures defining waveforms such as templates could be stored and retrieved as needed by routines 442 and 444, such as in memory 408 (FIG. 6). Similarly, intermediate and final results of operations in boxes 972, 980, 986, and 988 could similarly be stored and retrieved as needed.

Comparison techniques other than correlation could be employed, but correlation techniques can be advantageous because they are typically not sensitive to noise, such as an AC power frequency. For example, preliminary smoothing or other preprocessing of waveforms is typically unnecessary for correlation, and available techniques for computing correlations can produce useful results even with S/N ratios significantly less than 1.0. It is, however, necessary to satisfy minimum sampling requirements if waveforms are digitized for correlation; in accordance with the Nyquist frequency, each waveform should be sampled at least twice during the time duration of its minimum feature size.

Some techniques as described above have been successfully applied to simulated time-varying waveforms. In particular, time scaling techniques have been found to improve S/N ratio of a simulated observed signal that contains both an encoding based on a template and also additive noise, and where the observed signal has an unknown time scaling that occurs before it is observed; S/N ratio of 0.5 has been obtained and 0.1 appears achievable. These results could be obtained with particle speeds up to 0.5 m/sec and higher speeds up to a few msec appear to be feasible, with particles having effective sizes down to 0.6 μm, and with particle separations down to a given implementation's MFS. A demonstration included counting CD4 in a whole blood sample; single tag detection was shown to be feasible.

Where a simulated observed signal includes or is accompanied by a simulated concurrent periodically modulated signal, time scaling of a template waveform based on a scaling factor from the periodically modulated signal has successfully produced matching correlation results, indicating correlation or anti-correlation as appropriate and making spectral information available, in effect allowing concurrent detection of multiple colors with a single detector such as a large-area photosensor. Because an object receives different excitations at almost the same time and location (due, for example, to interdigitated or otherwise patchworked or patterned excitations), differences in absorption and excitation spectra can be measured with very high precision; similarly, because different spectral subranges of an object's emission spectra are measured at almost the same time and location (due, for example, to interdigitated, or otherwise patchworked or patterned filter arrangements), differences in emission spectra can be measured with very high precision; therefore, with one or both of patterned excitation and patterned filtering, many types of errors cancel out, including time-dependent factors such as bleaching, intermixing, diffusion and also errors induced by excitation differences such as temperature gradients and optical misalignments. Particle position can be precisely determined from fine structure of correlation results. As noted above, simulation results show that spatial resolution of less than 1.0 μm is possible, and single fluorescence markers can be detected, making detection possible with smaller amounts of consumables such as markers. The techniques appear appropriate for native fluorescence, allowing agent-less detection.

Some of the implementations described above in relation to FIGS. 1-28 are examples of a method of using a filter arrangement. While an object travels along a path past the filter arrangement and emanates light within an application's range of photon energies, the method transmits/reflects at least some of the emanating light through the filter arrangement. In doing so, the method includes at least one of the following two: First, while the object is in each of two or more segments of the path, the method transmits/reflects respective portions of the emanating light through respective positions of a filter assembly within the filter arrangement; each of the respective positions has a respective transmission function, and the transmission functions of at least two of the positions are sufficiently different that time variation occurs in the emanating light between at least two of the segments. Second, while the object is in each of a series of segments of the path, the method transmits/reflects a respective portion of the emanating light through a filter component within the filter arrangement, and the filter component has a combined transmission function in which a set of simpler transmission functions is superimposed; the set of transmission functions is superimposed such that time variation occurs in the emanating light in accordance with superposition of first and second simpler non-uniform transmission functions in the set.

In specific implementations, the method can do both, i.e. it transmits/reflects respective portions of the emanating light through respective positions of a filter assembly and also transmits/reflects a respective portion of the emanating light through a filter component. The filter assembly can include first and second filter elements that include first and second respective positions, and each of the first and second filter elements can have a respective transmission function that is approximately uniform for light from its respective segment of the path. For example, the transmission functions of the first and second filter elements can be spectrally different, and the method can encode spectral information in time variation of the emanating light. Also, the transmission functions can be different in transmitted/reflected intensity, and the method can encode intensity information in time variation of the emanating light. More generally, the method can encode information about the object in time variation of the emanating light, such as information indicating the type of the object.

In further specific implementations, each of the segments of the path can be at least approximately as large as the object's size. The combined transmission function can have a minimum feature size (MFS) at least approximately as large as the object's sizes. The series of segments in which the method transmits/reflects emanating light through the filter component can be substantially continuous. Similarly, the segments from which emanating light is transmitted/reflected through respective positions of the filter assembly can be segments within a sequence in part of the object's path. The method can cause the object to travel along the path with non-uniform displacement, such as by changing its displacement rate or its displacement direction. The object can be, for example, a biological cell or virus, and the application can be flow cytometry.

The simpler non-uniform transmission functions that are superimposed can include at least one that is non-periodic. Examples of simpler transmission functions can include, in addition to periodic functions, random and chirped functions.

Some of the implementations described above in relation to FIGS. 1-28 are examples of apparatus that includes a fluidic structure with a channel through which objects can travel along respective paths during operation and an encoding component with a filter arrangement that can receive light emanating from objects in the channel. In response to input light emanating from an object, the filter arrangement provides output light. The filter arrangement includes at least one of the following two: First, a filter assembly with a set of positions, each having a respective transmission function; a sequence of segments of an object's path including at least two segments from which respective positions in the set receive emanating light, and the transmission functions of the positions are sufficiently different from each other that time variation occurs in the output light while the object travels through the sequence of segments. Second, a filter component that receives input light from a segment of an object's path and has a combined transmission function in which a set of two or more simpler transmission functions are superimposed; the set includes first and second simpler non-uniform transmission functions, and the set is superimposed such that time variation occurs in the output light in accordance with superposition of the first and second simpler non-uniform transmission functions while the object travels through the segment.

In specific implementations, the apparatus can encode information about the object in time variation of the output light. The apparatus can also include a photosensing component that photosenses the time-varying output light and provides sensing results, such as with electrical signals. The apparatus can also include a processing component that responds to the sensing results, performing operations to obtain data indicating information encoded in the output light. The processing component can be programmed, for example, to perform a comparing operation to obtain comparison results between time-varying waveforms, at least one of which is from the sensing results, and can use the comparison results to obtain data indicating at least one spectral difference between the time-varying waveforms; the comparing operation can be correlation, and the time-varying waveforms can include a sensed time-varying waveform and a template time-varying waveform.

In specific implementations, the filter arrangement can include one or more of many different filter components, such as an absorption filter; an interference-based filter; a light-transmissive and/or light-reflective filter; a longitudinal sequence of filters that vary in a periodic, random, or chirped pattern; filter elements of two or more colors; filter elements of two or more gray levels; overlapping filter elements; a longitudinal sequence of filter elements that includes binary, gray level, and color filter elements; two or more lengthwise extending filter elements; a radial sequence of filter elements; two orthogonally striped filter assemblies; filter assemblies on opposite sides of a fluidic channel; and a stack-equivalent filter. The filter component can include the filter assembly, which can have one of the first and second simpler non-uniform transmission functions. At least one of the simpler non-uniform transmission functions can be a periodic, random, or chirp function of position.

In specific implementations, the apparatus can be a flow cytometer, with the objects being, for example, biological cells or viruses. In other implementations, the apparatus can be a scanning device.

Some of the implementations described above in relation to FIGS. 1-28 are examples of a method that transmits/reflects light emanating from objects through a filter arrangement while each object travels along a respective path past the filter arrangement. The method can transmit/reflect at least some of the object's emanating light through a longitudinal sequence of filter elements within the filter arrangement, while the object travels through a segment of its path. The longitudinal sequence includes a first subset of filter elements that have approximately a first transmission function and a second subset that have approximately a second function, with the first and second transmission functions being sufficiently spectrally different from each other that time variation occurs in the emanating light while the object travels through the segment.

In specific implementations, the time variation encodes spectral information about the object, and the method can photosense the emanating light to obtain photosensing results, then use the photosensing results to obtain data indicating the encoded spectral information. The photosensing results can indicate sensed time-varying waveforms, and the method can perform a comparing operation on a set of time-varying waveforms to obtain comparison results, with at least one of the time-varying waveforms being a sensed time-varying waveform; the method can use the comparison results to obtain data indicating at least one spectral difference between the time-varying waveforms.

In further specific implementations, where objects have different respective emanation spectra, the method can detect a difference between the spectra. The longitudinal sequence can be a sequence of spatially patterned filter elements that includes at least one spatially patterned color filter element and at least one spatially patterned non-color filter element such as a black and white or gray level filter element. More generally, a sequence of patterned filter elements can include patterns sufficiently different that different information items are concurrently encoded in the emanating light without loss of information.

Some of the implementations described above in relation to FIGS. 1-28 are examples of a method that transmits-reflects light from objects through a filter arrangement while the objects travel past the filter arrangement. The method transmits-reflects at least some of an object's emanating light through a filter component within the filter arrangement while the object travels through a segment of its path. The filter component has a combined transmission function in which a set of simpler transmission functions is superimposed. The set includes first and second simpler non-uniform transmission functions and is superimposed such that time variation occurs in the object's emanating light in accordance with superposition of the first and second simpler non-uniform transmission functions while the object travels through the segment.

In specific implementations, at least one of the first and second simpler non-uniform transmission functions is a spectrally-dependent function that transmits more than one color as a function of position. The first non-uniform transmission function can be a non-periodic spectrally-dependent transmission function and the second can be a period transmission function. At least one of the first and second non-uniform transmission functions can be a spectrally-independent transmission function that transmits black and white and/or gray scales. At least one of the simpler non-uniform transmission functions can be periodic, random, or chirped. As above, the time variation can encode information, and photosensing results can be used to obtain data indicating the encoded information.

Implementations as described above in relation to FIGS. 1-28 could be advantageously applied in a wide variety of sensing applications, possibly including, for example, fluorescence- or impedance-based flow cytometry or other biodetector applications that seek a signature of a particle of unknown velocity; such biodetectors often use microfluidic channels with inhomogeneous flow profiles, causing variation in particle velocity. The techniques can be used to count or obtain ratios between fluorescing objects of different types, such as different types of tagged cells, particles, tagged DNA, and so forth. In such an application, calibration can be performed using known objects, e.g., tagged beads, with known velocities to obtain template waveforms that include deviations caused by fabrication tolerances but can then be compared with sensed waveforms to obtain information about unknown objects. To improve S/N, known and sensed waveforms can be correlated, such as after time scaling of each known waveform. If a sensed waveform includes or is accompanied by periodic modulation, a periodicity value such as a frequency can be used to obtain a scaling factor for time scaling before correlation, allowing more rapid correlation than if a brute force technique is used to find a satisfactory time scaling.

Implementations described above may be advantageous in biodetector applications that require compact, low-cost components without critical optics and with high sensing efficiency. Such applications might include point-of-care flow cytometry (such as with an integrated flow cytometer), DNA analysis, proteomics, and so forth.

Implementations described above could successfully detect native fluorescence differences between biological materials. Most biological cells are composed of only a few basic building blocks and, therefore, exhibit similar native fluorescence spectra. Interdigitated or otherwise patchworked or patterned filter arrangements like those above are particular suitable for differentiation of objects based on their native fluorescence signals because the techniques are sensitive enough to detect the native fluorescence from a single cell and allow direct measurement of distinguishing features such as intensity ratios in emission spectra. In addition, implementations of the techniques can combine advantages of excitation and emission spectroscopy in a rugged and compact system.

Also, implementations described above could be applied in scanning of bio-chips or documents where objects have different emanation spectra, and so forth. The techniques may also be applicable in various low S/N ratio systems in which a known signal is bounced off an object traveling at an unknown velocity, such as where object velocity is on the order of signal propagation velocity, as in SONAR. The techniques may be especially advantageous where precise information about position, speed, or type of objects is sought.

Exemplary implementations described above employ photosensors or impedance-based sensors with specific features, but a wide variety of sensors could be used to obtain sensing results indicating values of various parameters other than emanating light intensity, parameters that can have time variation that indicates information about objects. Similarly, implementations described above involve sensing information about objects that are moving in fluidic channels or that are moving relative to a sensor such as in scanning, but various other types of fluidic implementations or other implementations in which objects move in various other ways could be sensed to obtain sensing results suitable for techniques described above. For example, information could be obtained from native fluorescence of particles in an air stream. Also, an excitation pattern could be scanned across a glass slide with immobilized analyte particles such as tagged cells or DNA spots, to obtain emanating fluorescent light.

Components of exemplary implementations as described above could have various shapes, dimensions, or other numerical or qualitative characteristics other than those illustrated and described above. Similarly, although the exemplary implementations generally involve sensing from a single fluidic channel, implementations could readily include multiple parallel channels, allowing parallel sensing and readout and larger scale sensing.

Some of the above exemplary implementations involve specific types of fluidic components, filter components, light source components, displacement control components, sensors, and so forth, but the invention could be implemented with a wide variety of other types of components. For example, some implementations use specific types of spatial modulation based on one or more of an excitation pattern, a filter assembly, and/or displacement control, but various other types of spatial modulation could be used, including any appropriate combination of color, gray level, and black and white patterning and including other patterning techniques such as patterned sensing; for example, in a fluidic implementation, a filter assembly or a patterned photosensor could be printed or otherwise produced on an inward wall or other boundary of a channel or in another appropriate location. Also, some exemplary implementations use specific types of processing, such as digital signals obtained after converting sensed analog values. In general, however, the invention could be implemented with any suitable signal processing techniques, including any appropriate combination of analog and digital processing; either or both of two compared waveforms could be obtained in analog or digital form, and any combination of time scaling could be performed before comparison. Further, some exemplary implementations use large area photosensors, but various ICs with photosensing arrays might be used.

Some of the above exemplary implementations involve specific types of emanating light, e.g. fluorescence, and specific types of excitation and filtering suitable to fluorescent light, but these are merely exemplary. The invention could be implemented in relation to various other types of optical signals in various other ranges of photon energies or with any other appropriate sensed stimuli.

Some of the above exemplary implementations involve specific materials, such as in fluidic structures with light-transmissive components or in filtering arrangements with reflective material or light blocking material such as amorphous silicon, but the invention could be implemented with a wide variety of materials and with layered structures with various combinations of sublayers. Thicknesses of layers may vary across any suitable range.

The exemplary implementation in FIG. 6 employs a CPU, which could be a microprocessor or any other appropriate component. Furthermore, as noted above, operations could be performed digitally or with analog signals, and could be done either on the same IC as a photosensor array, on other components, or on a combination of the two, with any appropriate combination of software or hardware.

The above exemplary implementations generally involve use of encoding/sensing arrangements, sensors, photosensors, excitation arrangements, filter arrangements, displacement control arrangements, and so forth following particular operations, but different operations could be performed, the order of the operations could be modified, and additional operations could be added within the scope of the invention. For example, readout of sensed quantities from a sensor to obtain a sensed time-varying waveform could be performed serially or in parallel, and, with an array, could be performed cell-by-cell or in a streaming operation. Principal component analysis could be applied to specifically chosen intensity ratios in the emission spectrum in distinguishing cells or other objects, possibly allowing identification. Multiple photosensors along a channel could measure different intensity ratios in the emission spectrum, possibly allowing identification of objects based on either emission characteristics. Dyes that are very similar may be distinguishable if they reveal only slightly different emission spectra, and use of similar dyes could be advantageous in satisfying pH requirements within cytometers.

Figure 29:
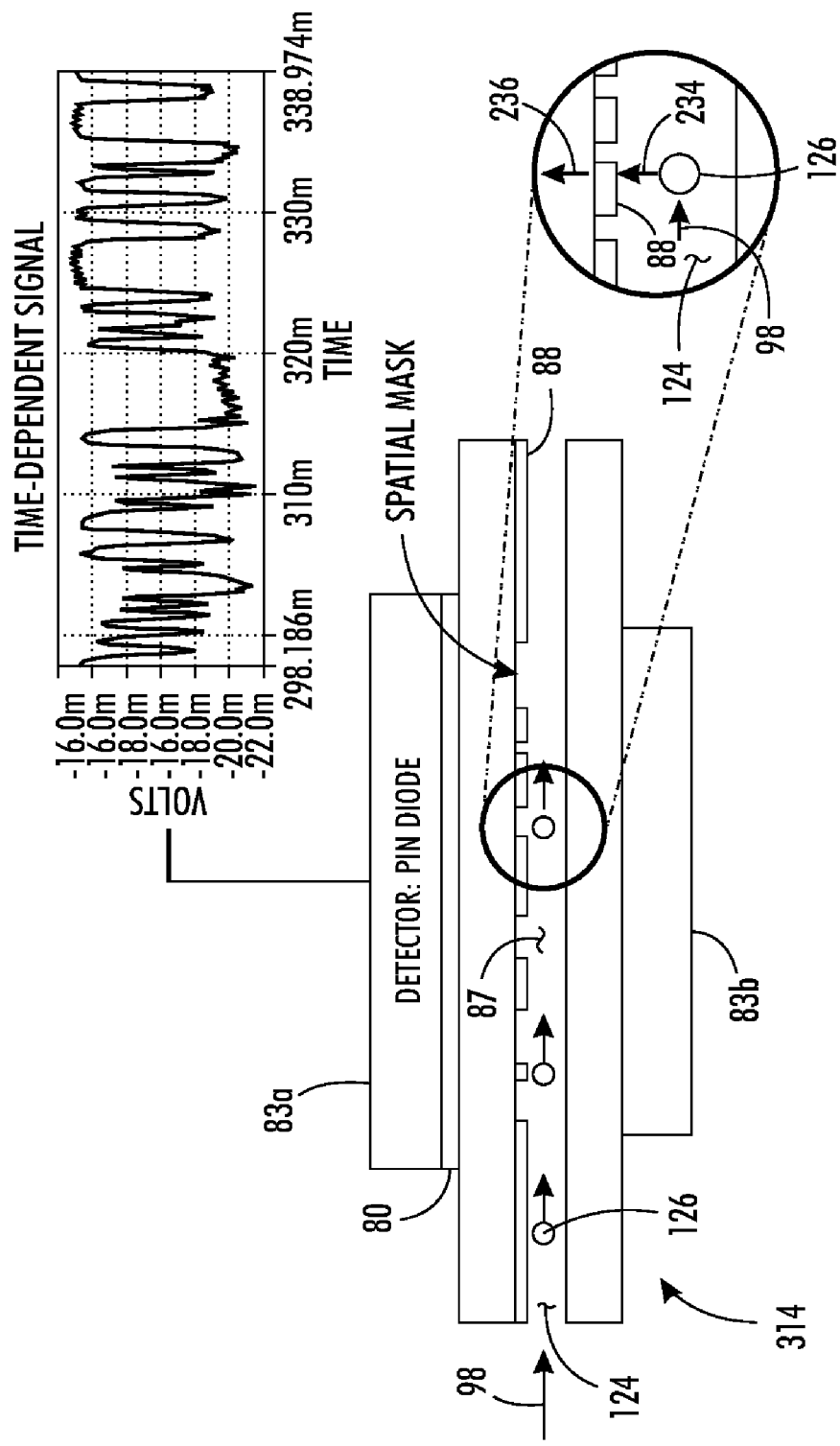
FIG. 29 illustrates an embodiment of a fluidic chip for detection of spatially modulated fluorescence along with an expected time-dependent output electrical signal according to an embodiment of the present invention.

Discussion is now directed towards an apparatus, which is generally referred to as a flow cytometer, for diagnosing fluids. Examples are testing the quality of water for personal or industrial use, or testing blood for various disease-causing organisms. According to an exemplary embodiment, a flow cytometer produced according to the exemplary embodiments described herein, will make use of a novel spatially modulated emission technique that can be used with the apparatus as shown in FIG. 29. FIG. 29 is a schematic diagram of an exemplary embodiment of a fluidic chip for determining information about objects, particles, viruses, or functionalized micro beads (hereinafter referred to as "objects" 126), using spatial modulation and fluorescing emission from moving object 126 according to an exemplary embodiment. In the spatially modulated emission technique, a patterned (e.g., pseudo-random, periodic or chirped) mask 88 is introduced optically between light emitting object 126 (light emission is stimulated by light source 86 not shown in FIG. 29) and a photo sensor (or photo detector) 83a to produce time variation in the signal (the signal being light, and otherwise referred to as emanating light 234). Light beam 98 (generated by light source 86) impinges upon, or strikes, objects 126, and causes them to fluoresce or scatter. The act of fluorescing means that object 126 reacts to the impinging light beam 98, and creates light of a different frequency and with other characteristics that are a function of the type of object 126 that is being hit, or impinged, with light beam 98, and its ability to fluoresce. As those of ordinary skill in the art can appreciate, not all objects 126 will fluoresce. Emanating light 234 is the fluorescent or scattered light leaving object 126. As the fluorescing or scattering objects 126 flow through excitation area 87, the relative movement of object 126 produces a time modulated signal at detectors 83a, b (the light now referred to as encoded emanating light 236 that leaves mask 88) due to the pattern of the provided mask 88. The output of photo detector 83a is an electrical time varying signal or time dependent signal as shown in FIG. 29. Correlating the detected signal with the pattern of mask 88 discriminates the fluorescence or scatter signal (i.e., emanating light 234) from the background noise, giving an improved signal-to-noise discrimination, and provides precise information about the speed and position of object 126.

According to an exemplary embodiment, a portable, hand held flow cytometer can be fabricated according to the above described principles of spatial modulation that exhibits increased signal-to-noise ratio (SNR, or S/N) discrimination, that allows replacement of the complex optics, fragile PMT (photomultiplier tube) detectors and bulky expensive light sources of prior art designs. For purposes of this discussion, general reference is made to a "flow cytometer" built in accordance with the principles discussed above. In regard to exemplary embodiments, discussion is also made in regard to prototype flow cytometer 300 and point-of-care flow cytometer 308, both of which are discussed in greater detail below. Furthermore, a flow cytometer built according to the exemplary embodiments can be both robust and miniaturized, wherein such result arises from the use of inexpensive components that can be readily integrated on a fluidic chip according to an exemplary embodiment, and by eliminating the need for sophisticated optics and critical optical alignment. The use of lower-cost lasers, such as those used in laser pointers or recently developed laser diodes (LDs), and simpler detection electronics, such as miniature photodiodes and single-chip digital signal processors, mean that a small, rugged system can be built.

According to exemplary embodiments, techniques for using a flow cytometer fabricated as discussed herein have been demonstrated with CD4 counting in whole blood. In general, a flow cytometer built according to the exemplary embodiment comprises a disposable fluidic chip with a host structure, and can be used for real-time bacteria monitoring of potable water sources to insure water quality is maintained and corrective action is taken quickly, as needed. As those of ordinary skill in the art can appreciate, contamination between samples can be an issue with any field testing, such as envisioned with flow cytometers 300, 308. However, through use of low cost disposable fluidic chips designed and built according to the exemplary embodiments, problems associated with contamination become substantially minimized, if not completely eliminated.

According to a further exemplary embodiment, the flow cytometer can be used to accurately detect giardia, cryptosporidium, E. coli and bacillus endospores, among other bacteria. According to still a further exemplary embodiment, a flow cytometer can be used to detect giardia and cryptosporidium in a handheld embodiment for use in the field, or as a compact permanently installed in-line water monitor.

According to an exemplary embodiment, the flow cytometers described herein uses a fundamentally new design of the optical detection system that delivers high effective sensitivity (i.e., high signal to noise) without complex optics or bulky, expensive light sources to enable a flow cytometer that combines high performance, robustness, compactness, low cost, and ease of use.

As those of ordinary skill in the art can appreciate, commercial flow cytometers are not only expensive, but they also require sophisticated equipment and reagents, as well as highly trained personnel to operate them. Furthermore, in resource-limited areas, access to technical support and quality assurance programs are often unavailable. A non-exhaustive list of examples of such resource limited areas include certain geographical localities of the world (i.e., non-industrialized nations with very low per-capita income levels), rural areas in industrialized nations with otherwise relatively high per-capita income levels, elderly care environments, medical units in the different armed forces when on the field, disaster relief medical units (e.g., FEMA, especially in relation to natural disaster areas, such as those ravaged by earthquakes, or hurricanes), traveling physicians (e.g., physicians that may be responsible for treating a relatively small amount of people, but in large geographical areas), emergency medical technicians, outpatient basis clinics, groups involved in camping and exploration (e.g., polar, underwater, mountain climbing, among others), space travel, among other areas and types of endeavors.

One exemplary use of the flow cytometer according to an exemplary embodiment is for rapid bacterial identification and quantitation in water. Desired features of such a flow cytometer for use in identifying and counting bacteria in water include detecting at least the bacterial contaminants that include giardia, cryptosporidium, E. coli, and cacillus endospores; the flow cytometer should be a hand-held, field-deployable, fluidic-chip-based, multi-parameter flow cytometer, be capable of utilizing biochemical tagging protocol(s).

According to still a further exemplary embodiment, the flow cytometer according to an exemplary embodiment is a component of three tandem micro-fluidic sub-systems: a pre-concentrator, a sample-preparation chip, and the flow cytometer. According to an exemplary embodiment, the performance goal for the overall system is a detection sensitivity of about 1/100 mL. The system goal is full integration of the three sub-systems into a single compact instrument. According to still a further exemplary embodiment, conservation of consumables is achieved by applying the tagging protocol to only the concentrated sample volume. A flow cytometer built according to an exemplary embodiment can be integrated as a single hand-held point-of-care system (discussed in greater detail below) and operated with the tagging protocol and software for a complete water monitoring system, or be fabricated as an in-line monitoring system as a completely manufacturable unit (discussed in greater detail below).

According to an exemplary embodiment, the identification and quantitation of selected bacteria at the level of 1 organism per 100 mL of water sample can be accomplished at the point-of-need in less than about 20 minutes with the flow cytometer according to the exemplary embodiments that can be operated by personnel with minimal training. However, the duration, identification and quantitation specifications discussed above can and will vary depending upon the circumstances and nature of the environment in which the testing occurs, and as such is not meant to be taken in a limiting manner.

According to further exemplary embodiments, the flow cytometer according to the exemplary embodiments can be used with at least two different biochemical tagging protocols: in the first instance biochemical tagging occurs by detecting the bacteria of interest in the water sample with a fluorescent moiety using antibody tags. In a second case, the tagging of the bacteria occurs through the use of fluorescent aptamer tags (e.g., nucleic acid or peptide).

As those of ordinary skill in the art can appreciate, water quality monitoring is high priority for public, industrial, and military applications. For example, microorganisms are the key catalyst for wastewater treatment, and the primary causative agents for the failure of water purification systems and the occurrence of infectious diseases. The U.S. Centers for Disease Control and Prevention (CDC) estimates that between 200,000 to 1,000,000 people each year in the U.S. become ill from contaminated drinking water, and an estimated 1,000 die. Worldwide it is estimated that 5500 people die daily from drinking contaminated water.

Bacterial cell quantity should be routinely monitored to maintain microbiological quality control of drinking water. Mobile water supply units currently use water purification units based on micro- or ultra-filtration followed by reverse osmosis (RO) filtration and then stores the potable water in tanks. Even with this advanced system, water quality in the potable tanks is still a concern and needs to be regularly tested because it can become contaminated during production, handling, storage, or distribution. Due to lack of suitable testing devices, currently all water has to be treated by an expensive and energy consuming RO filtration technique. In order to check the integrity of the RO water filtration system, regular micro-biological water testing is desired. Other uses of a flow cytometer according to the exemplary embodiments include water testing of swimming facilities (both public and private), including pools, and beaches, and testing of portable and not-portable drinking water supplies. In these exemplary uses, the flow cytometer according to the exemplary embodiments can be configured as a stand-alone point-of-care device, or as an in-line monitoring device (e.g., in a pool filtration system). Currently available commercial tests can take as long as 18-24 hours to determine the presence (or not) of micro-organisms such as E. coli. As those of ordinary skill in the art can appreciate, test results that lag that far behind actual usage means that precious little can be done for those that have used or drank the affected water in the past day or so. According to further exemplary embodiments, the detection of harmful microorganisms (e.g., E. coli) by a flow cytometer within about 20 minutes provides a significant increase in protecting the health of those that drink the water, and/or swim in the water As those of ordinary skill in the art can further appreciate, organisms that indicate the presence of sewage and fecal contamination have been targeted for measurement. One particular example, discussed briefly above, is coliform which describes a type of bacteria that includes *Escherichia coli* (*E. coli*). *E. coli* is generally found within the intestines of all warm blooded animals and is an indicator analyte for other dangerous pathogens. Another well known type of bacteria that should be detected is enterococcus, which is much like coliform bacteria, but is known to have a greater correlation with swimming-associated illnesses and is less likely to die-off in highly saline water. These pathogens, if contacted, could result in such symptoms as diarrhea, cramps, and nausea.

In the US alone, billions of gallons of untreated or under-treated sewage is discharged into waterways yearly, potentially impacting drinking water and causing beach closings. Therefore, there is a need for an inexpensive, early warning biosensor to monitor both beaches and drinking water.

As those of ordinary skill in the art understand, bacterial quantitation is currently performed primarily in central laboratories with plate culture assay techniques; this infrastructure and procedures have been integral to microbiology for more than 100 years. The method of choice to determine bacterial coliform count in potable water starts with the membrane filter technique, then incubation growth in a plate culture followed by counting of the colony-forming units. Unfortunately culture assay techniques for quantitation are costly, labor-intensive and time-consuming to conduct, with measurement times greater than 24 hours due to incubation needs. Culture-independent techniques have used fluorescent microscopes, but results are labor intensive and subjective because visual counting varies among investigators.

Presently available commercial flow cytometers are an effective and well-established method for counting and sorting cells on a large scale, as they are rapid, sensitive, and can reliably quantify individual cells, but they are also skill and labor intensive. Commercially available flow cytometers require expensive light sources and detectors to adequately illuminate samples and ensure that enough scattered and emitted light is collected for analysis. The complexity of the optical system and the need for high-quality lasers and detectors make most commercial flow cytometers bulky, expensive, and fragile. Consequently, their use is limited to laboratories with highly skilled workers and a fairly high level of infrastructure support. In contrast, a micro-fluidic device built according to an exemplary embodiment such as the flow cytometer designed and built according to the exemplary embodiments has the potential to increase ease-of-use by integrating sample pretreatment and separation strategies.

As discussed above, presently used techniques for the detection of waterborne parasites are primarily based on antibody-antigen reaction assays that vary in sensitivity and specificity. Also, cross-reactivity between pathogenic and non-pathogenic species represents a problem when exclusively using these assays to monitor safe drinking water.

A further exemplary use of the flow cytometer according to the exemplary embodiments is for rapid identification and quantitation of blood borne pathogens (such as bacteria or viruses), or to analyze and count the constituents of the blood, such as certain subgroups of white blood cells (e.g., CD4 lymphocytes). As those of ordinary skill in the art can appreciate, low levels of cluster of differentiation 4 (CD4) lymphocytes indicates a compromised immune system, and can indicate the presence of the human immunodeficiency virus (HIV) (which is a lentivirus, or a member of the retrovirus family), and which itself causes acquired immunodeficiency syndrome (AIDS). AIDS is a condition in which the immune system of people begins to fail, leading to life-threatening opportunistic infections (i.e., pneumonia, or other illnesses).

A first exemplary embodiment of the flow cytometer according to the exemplary embodiments can be used for monitoring a single fluorescent emission band of a targeted pathogen or its signature, such as absolute CD4 counting for HIV, by means of excitation with a laser diode (LD) or light emitting diode (LED) and detection with a P-type intrinsic N-type (PIN) photo diode. As used herein, light source 98 includes both LD 238 and LED 240, and photo detector 83 includes both PIN diode detector 122 and avalanche photo diode (APD) detector 84. According to further exemplary embodiments, flow cytometer can also be configured as a multi-parameter instrument that can detect multiple fluorescence channels, wherein such device can be utilized, by way of just one example, for percent and absolute CD4+ T-lymphocyte counts.

As with the exemplary embodiment of flow cytometer for use in water testing discussed above, the flow cytometer according to the exemplary embodiments for use in blood testing has the desired features of performance, robustness, compactness, low cost of production and use, reagent consumption, and ease of use.

A compact two-color flow cytometer according to the exemplary embodiments can use a patterned color mask and a single large area detector, according to an exemplary embodiment, to perform more complete diagnostics, e.g., CD4% and absolute CD4 count. A further exemplary embodiment of the flow cytometer can be used for the detection of malaria.

As those of ordinary skill in the art can appreciate, presently available commercial flow cytometers are indispensable tools in clinical diagnostics, such as in diagnosing cancer, AIDS, and infectious diseases during outbreaks, and also in microbiology and other areas. Chemical and or physical information is obtained about a moving object such as a biological cell, a virus, a molecule, or a sub-molecular complex, as it flows in a fluid stream. However, as those of ordinary skill in the art can attest to, the cost, complexity, and size of existing commercially available flow cytometers preclude their use in field clinics, point-of-care (POC) diagnostics, water monitoring, agriculture/veterinary diagnostics, and rapidly deployable bio-threat detection.

Furthermore, a number of commercially available flow cytometers use multiple excitation sources, each focused on a well-defined location or region separate from the others. Light emitted from each source's region is typically analyzed with a series of beam splitters, filters, and photomultiplier tubes (PMTs) in order to detect and distinguish differently stained cells or cells that concurrently carry multiple dyes. Cells are typically stained in solution with different dyes prior to insertion into a cytometer, and the measurement event occurs as the cells traverse a detection region within a fluidic channel, at a speed of up to several meters per second. In the detection region, focused laser light (typically with an elliptical focus of 80 μm×40 μm) excites the dyes on the cells. The resulting fluorescent light can be collected by a microscope lens, sorted by band pass filters, and detected by PMTs or APDs (avalanche photo diode). For each spot excitation, a respective set of filters and detectors is needed, which is costly and leads to bulky instruments with critical requirements to maintain optical alignment. Since the detection region is very small, and the objects traverse it rapidly (typical dwell times are around 10 μs), such flow cytometers have serious signal-to-noise ratio (SNR) limitations for weakly fluorescing cells. These limitations become more acute if multiple targets must be characterized and distinguished for counting or sorting. Thus, all presently available commercial approaches appear to require sophisticated, high-cost components or suffer from low performance (e.g., time per measurement, robustness, sensitivity, ease to use).

Therefore, no commercial instrument meets all technical requirements for POC resource-limited settings, and in particular the cost target remains extremely challenging. In view of all this, the medical necessity and practical challenges are enormous. The HIV pandemic has created an unprecedented global health emergency. In response, the price of life-saving HIV drug treatment has been reduced to under $100 per year. More than 3 million people have started treatment in the past five years. But of the 33 million people living with HIV worldwide, fewer than 10% have access to CD4 cell monitoring, the critical blood test used by clinicians to decide when to start treatment. Fewer than 1% have access to viral load assays, which are used for infant diagnosis and for patient monitoring. It is estimated that about 0.6% of the world's population is infected with HIV. In 2005 alone, AIDS claimed an estimated 2.4-3.3 million lives, of which more than 570,000 were children. The urgent need to reach HIV-infected patients presents an unprecedented opportunity to drive technology development in point-of-care diagnostics.

Thus, what is needed is the development of a convenient, low-cost instruments for CD4 counting that is compact and robust enough for healthcare workers to carry to patients in remote settings. Such portable instruments must also be capable of providing absolute CD4 counts. Better information to decide when and which treatment to initiate can be provided with CD4% (percentage of white blood cells that are CD4+ T-lymphocytes), the CD4/CD8 ratio, or viral load measurements. The latter measurements are particularly essential for infected children. According to an exemplary embodiment, flow cytometers described herein have been designed to meet the medical communities' needs in fighting the global AIDs problem as discussed above.

Figure 30:
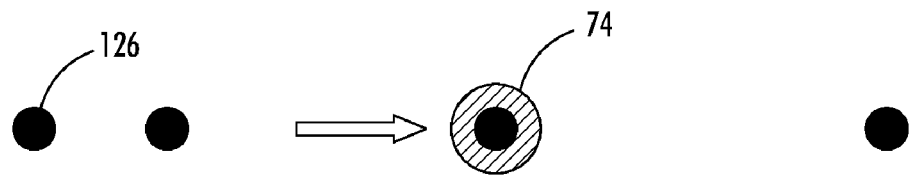
FIG. 30 illustrates imposition of spatial modulation on fluorescence emission from a moving particle for a conventional flow cytometer with a highly focused spot of light.
Figure 31:
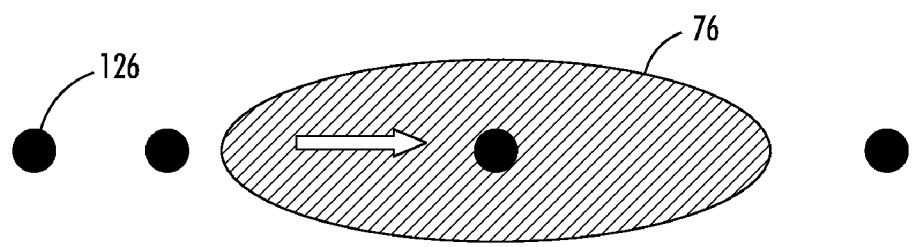
FIG. 31 illustrates imposition of spatial modulation on a larger fluorescence emission than in FIG. 30 from a moving particle for a conventional flow cytometer with a lesser focused spot of light than shown in FIG. 30.
Figure 32:
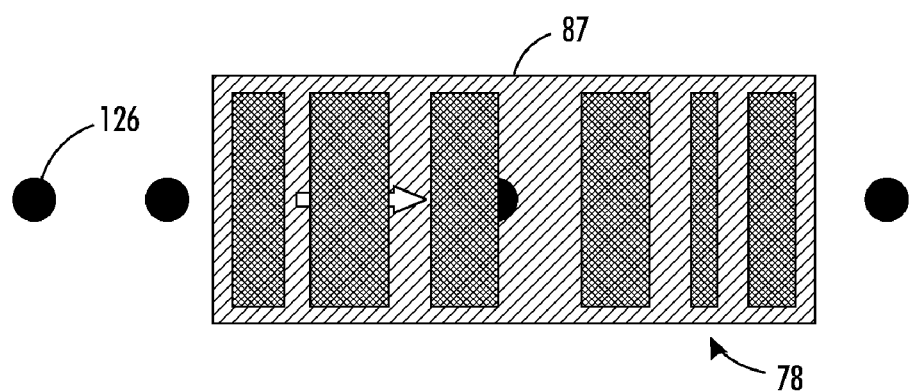
FIG. 32 illustrates imposition of spatial modulation on fluorescence emission from a moving particle with a patterned collection zone superimposed on the fluorescence emission for a flow cytometer according to an embodiment of the present invention.

In this section, an optical detection technique is described that delivers high signal-to-noise discrimination without precision optics that enables the flow cytometers described herein to provide high performance, robustness, compactness, low cost, and ease of use. According to an exemplary embodiment, the enabling technique is termed "spatially modulated emission" and generates a time-dependent signal as a substantially continuously fluorescing bio-particle moves past a predefined pattern for optical transmission. Correlating the detected signal with the known pattern achieves high discrimination of the particle signal from background noise. Attention is directed to FIGS. 30-32

In contrast to conventional flow cytometry, wherein the size of the excitation is restricted to approximately that of the size of the particle, the spatial modulation technique described herein uses a substantially larger excitation area 87 to increase the total flux of fluorescence light that originates from a particle. Despite the size of the excitation area, the mask pattern enables a high spatial resolution in the micron range. This allows for independently detecting and characterizing particles with a separation (in flow direction) that can approach the dimension of individual particles. In addition, the concept is intrinsically tolerant to background fluorescence originating from fluorescing components in solution or fluorescence from the chamber or contaminants on surfaces.

The basic technique and first proof of concept demonstration is described in Ref 11 (P. Kiesel, M. Bassler, M. Beck, N. M. Johnson, Spatially modulated fluorescence emission from moving particles, Appl. Phys. Lett., 94, 041107 (2009)).

A variety of predefined masks can be used, which includes periodic, chirp, and finite-random patterns. A finite random pattern is defined herein to mean that a practical limitation has been placed, or is characteristic of a mask pattern; a truly random pattern would be significantly long, if not endless. As such, any shortened mask pattern becomes less than completely random, and as a natural result, is "finite-random." The functional form of the mask influences the obtainable particle information as well as S/N discrimination. A periodic mask has the advantage that the particle speed can be readily determined (e.g., Fourier transform or electronic lock-in techniques), however, it is less satisfactory for accurately determining absolute position of the particle or handling multiple particles in the detection area. These issues are elegantly resolved by adopting masks with a pseudo-randomly defined pattern. Correlating the recorded time-varying signal with the mask pattern can detect multiple particles in the detection zone and precisely determine their absolute positions and separation, with spatial resolution related to the minimum feature size of the mask pattern. The combined advantages of periodic and pseudo-random masks can be obtained by integrating the two patterns in a single mask according to an exemplary embodiment. In this case, data analysis can accurately yield both speed and position of each particle in real time.

In conventional flow cytometry, the size of the excitation area is restricted approximately to the size of the particle. According to an exemplary embodiment, the method described herein uses a much larger excitation area to increase the total flux of fluorescence light that originates from a particle. Despite the large excitation area, the mask patterning enables a high spatial resolution in the micron range. This allows for independently detecting and characterizing particles with a separation (in flow direction) that can approach the dimension of individual particles. In addition, the concept is intrinsically tolerant to background fluorescence originating from fluorescent components in solution, fluorescing components of the chamber and contaminants on the surface.

In FIGS. 30-32, the basic concept and benefit of imposing spatial modulation on the fluorescence emission from a moving particle is schematically shown. The arrangement for a conventional flow cytometer is shown in FIG. 30 with fluorescence emission 74 optically excited within a highly focused spot. The advantages of this approach include strong signal, high S/N, and good particle separation. But realizing these benefits requires high photon flux densities (i.e., intense light sources, precision optics and critical optical alignment), with the risk of saturation effects, and accurate control of both the flow path and speed of the particle. A conceivable partial fix for these disadvantages is shown in FIG. 31, with large fluorescence emission 76 that increases integration time for emission collection. While allowing lower excitation flux densities, with less saturation, and eliminating critical optical alignment, the fluorescence signal and the S/N would be concomitantly lower and particle separation would be poorer than in the conventional approach. The spatial modulation technique according to an exemplary embodiment is illustrated in FIG. 32 with patterned collection zone 78 superimposed on excitation area 87. The resultant time-dependent signal is analyzed with standard correlation techniques. This yields improved S/N discrimination and high spatial resolution with neither precision optics nor critical alignment, while using low excitation flux densities. In addition, the technique yields particle speed to enable volumetric calibration and simple fluidic handling.

Figure 33:
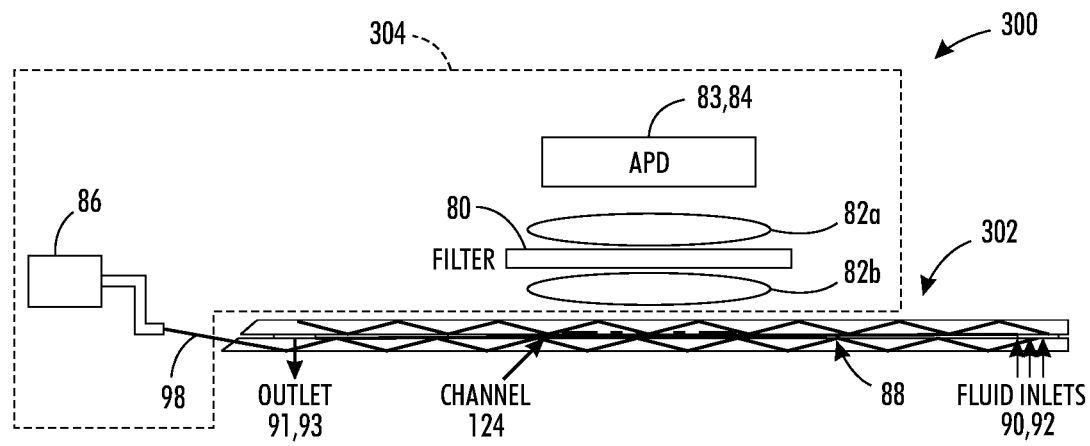
FIG. 33 illustrates an alternate embodiment of a fluidic chip, with laser excitation and apparatus to collect spatially modulated fluorescence according to an embodiment of the present invention.
Figure 34:
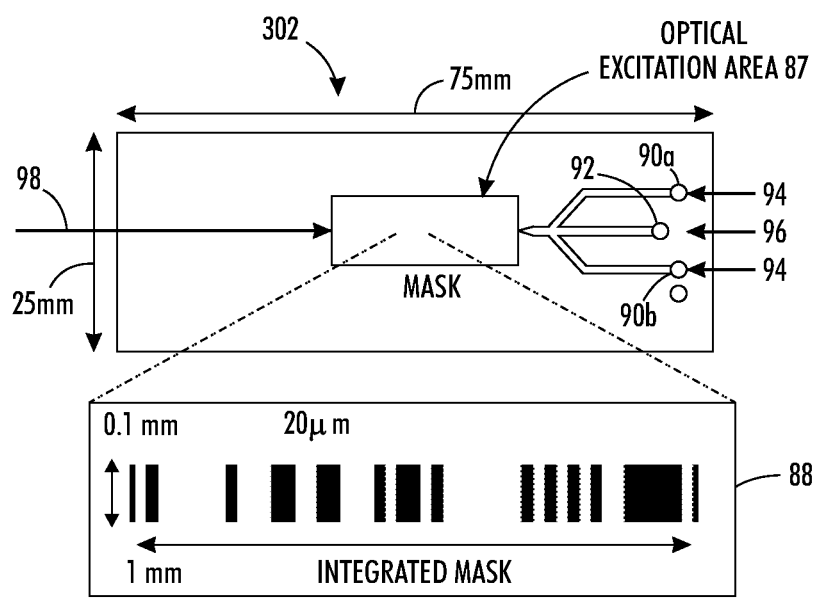
FIG. 34 illustrates a detailed top view of the fluidic chip and filter mask shown in FIG. 33 according to an embodiment of the present invention.

Attention is now directed towards FIGS. 33, and 34, which illustrates a first implementation of a flow cytometer (prototype flow cytometer) 300 that illustrates the principles of the exemplary methods. FIG. 33 illustrates, among other things, a side view of first fluidic chip 302 and FIG. 34 illustrates a top view of the same first fluidic chip 302, and mask 88. The flow cytometers built in accordance with the exemplary embodiments described herein, generally include a host structure, and a fluidic chip. The host structure generally includes one or more light sources, one or more photo detectors, and circuitry of various different embodiments to receive, analyze and interpret the detected signals, and provide some type of readout/display to indicate results. The host structure can further include various optical elements, including lenses, filters, masks, among other items. The fluidic chip, designed to be disposable, includes the channel for accepting analyte, that contains objects 126 as discussed above, and further includes one or more masks, and in some cases sheath fluids and inlets/outlets for the sheath fluids and analyte. In some cases, discussed in greater detail below, one or more masks can be part of the host structure, or the fluidic chip can also contain the photo detectors, and in some cases, the fluidic chip can contain the light sources. The host circuitry can include computers, microprocessors, field programmable gate arrays, and other logic circuitry, or combinations thereof.

Prototype flow cytometer 300, illustrated in schematic format in FIG. 33, includes first fluidic chip 302, and prototype host structure 304. Prototype host structure 304, not shown in its entirety in FIG. 33, includes an optical excitation source (light source) 86, lenses 82a, b, filter 80, and an avalanche photo detector (APD) 84 (according to an exemplary embodiment, APD 84 and PIN diode detector 122 are specific examples of types of photo detectors 83; accordingly, in some cases reference is made to one or the other of the specific examples of photo detectors 83, but aside from certain design considerations and also possible for supply/demand reasons, either can be used and in general reference may be made to either as shown in the figures. In other situations, reference will be made to the "generic" photo detector 83). For prototype flow cytometer 300, first fluidic chip 302 was formed with two closely spaced quartz slides to define a flow channel about 200 µm wide and about 25 µm deep. According to an exemplary embodiment, mask 88, shown in detail in FIG. 34, includes a pattern of gratings that are about 0.1 mm in height, about 1.0 mm in length, and that can have a width as low as 20 µm. A finite-random mask pattern (mask) 88 was photo lithographically defined in a metal film deposited on the inside surface of the top slide. A syringe pump (not shown) can be used to control both the flow of the bead-containing solution (analyte) 96 and the sheath flow (sheath fluid) 94. As those of skill in the art can appreciate, however, sheath fluid 94 is not required, but can be used to optimize the light-analyte interaction. Optical excitation can be provided by anti-resonantly coupling laser light into first fluidic chip 302, to achieve nearly uniform excitation along the path of the analyte 96 flow. In this configuration, analyte 96 flow can be manipulated relative to the excitation path to substantially minimize background noise and allow high distributed excitation with reduced bleaching of the dyes. For example, the interaction between the guided excitation light 98 and analyte 96 can be restricted to the detection zone by directing the flow of analyte 96 into guided light beam 98 just before detection area 87, and directing the flow out of light beam 98 right after detection area 87 (which occurs in the volume of area defined by mask 88 and APD 84).

The spatial modulation technique is described in detail in an article published in the Applied Physics Letters (APL), "P. Kiesel, M. Bassler, M. Beck, N. M. Johnson, Spatially modulated fluorescence emission from moving particles, Appl. Phys. Lett., 94, 041107 (2009)", the entire contents of which are incorporated herein by reference. The article discusses in great detail the spatial modulation technique, including that from the "raw" recorded data signal a correlation signal is generated between an ideal and the recorded data signal. The correlation signal then indicates detection of object 126, and following correlation, the derivative of the correlation signal is generated, and this yields the position of object 126.

In order to verify the capabilities of the spatially modulated detection technique and prototype flow cytometer 300, human blood samples were tested to determine the concentration of CD4 T-lymphocytes marked with R-phycoerythrin (PE) in a PBS buffer-solution. Attention is now directed towards FIGS. 35-40.

Figure 35A:
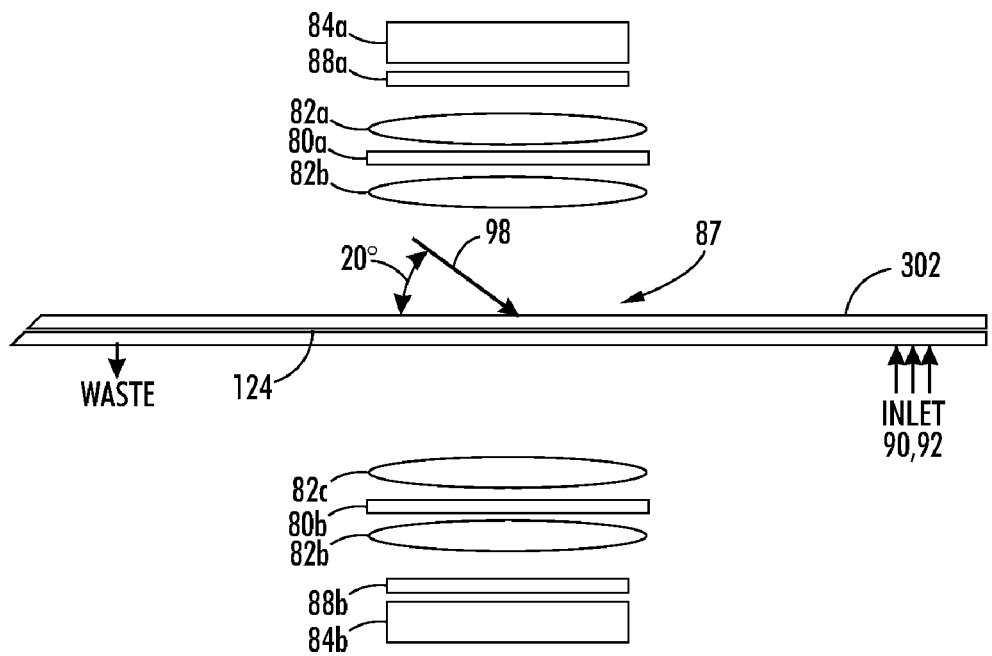
FIG. 35A illustrates an alternate embodiment of a fluidic chip, with laser excitation and apparatus to collect spatially modulated fluorescence according to an embodiment of the present invention.
Figure 35B:
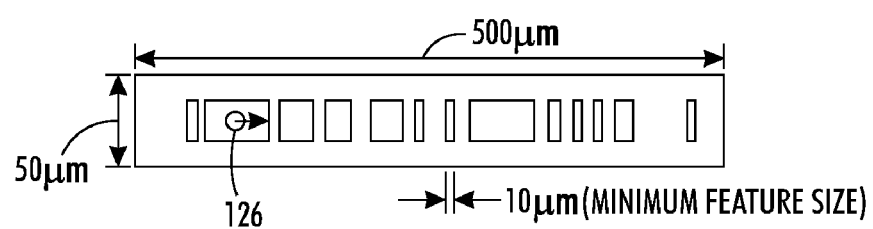
FIG. 35B illustrates a detailed top view of the embodiment of the filter mask shown in FIG. 35A according to an embodiment of the present invention.

For the blood sample testing, the set-up of prototype flow cytometer 300 as shown in FIG. 33 was modified slightly. The set up used for the CD4 measurements is schematically shown in FIG. 35A. Excitation light (532 nm laser) 98 was focused with cylindrical lenses (not shown in FIG. 35A) at ~20 degrees from the plane (~70 degrees from the normal) of first fluidic chip 302. The excitation area was about 0.6×0.03 mm$^2$. A remote sensing method was used to image the detection area of the fluidic chip onto the spatial mask (0.5×0.05 mm$^2$) with a pseudo-random pattern and a minimum feature size of 10 µm (see FIG. 35B). Masks 88a, b were placed in front of respective 3×3 mm$^2$ array-type avalanche photo-diode detectors 84a, b. The fluorescence from the CD4 cells was collected by a 20× microscope objective (NA=0.4; lenses 82a-d). Determination of absolute CD4 counts, discussed in detail below, require the use of only one fluorescence channel (i.e., a "one" parameter instrument), and only the upper detector 84a was used. For reliable detection of CD4%, however, both fluorescence channels need to be detected. For these measurements, both channels were recorded simultaneously from the opposite sides of the excitation area on the fluidic chip as indicated in FIG. 35A. This remote sensing arrangement was chosen to gain maximum flexibility for the absolute and percentage CD4 measurements (direct sensing means that mask 88 is integrated into the fluidic chip and the photo detector is attached to it; remote sensing means that particles in channel 124 are imaged onto mask 88 with a photo detector placed or located behind mask 88). According to a further exemplary embodiment, CD4 measurements were successfully accomplished with the set up described and shown in FIGS. 33 and 34 using a spatial mask integrated into first fluidic chip 302 using anti-resonant waveguide excitation. For these measurements, first fluidic chip 302 was redesigned to enable the analyte stream to be directed into the guided excitation light shortly before entering detection area 87. This minimized light scattering from red blood cells outside detection area 87 which is helpful when measuring whole blood samples. The excitation power density used for the CD4 measurements was less than 100 W/cm$^2$. The analyte-to-sheath-flow ratio was adjusted to about 1:15, with an analyte flow rate of about 6 µl/min. For the cross section of the fluidic channel 124 (25 µm×200 µm), an average flow speed of about 333 mm/s and a maximum flow speed $v_{max}$ of about 543 mm/s was calculated (which corresponds to a pressure drop of ~200 mbar along the 3 mm narrow section of the channel) Measurements taken yielded $v_{max}$ to be between about 550 to about 700 mm/s for channels with a width ranging from about 200 to about 250 µm, in good agreement with the prior calculations.

A basic, commercially available lab protocol was used to tag the CD4 cells. The blood samples were incubated with the antibody and dye (PE) (BD reagent 555347) for about 40 minutes at room temperature and diluted with PBS buffer solution for dilution factors of about 1:3. No lysing of the red blood cells or washing steps to separate the tagged blood cells from unbound dye was used.

Figure 36:
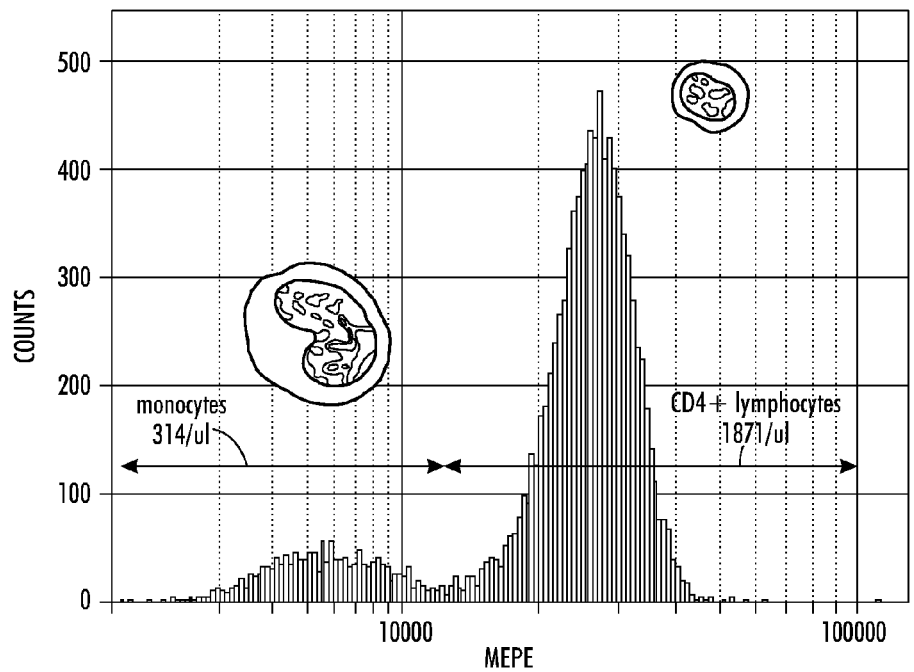
FIG. 36 illustrates a histogram of detected tagged cells as a function of fluorescent intensity for a blood sample containing CD4 lymphocytes and CD4 monocytes from data obtained using an experimental set-up substantially similar to that as shown in FIGS. 35A and 35B according to an embodiment of the present invention.

A variety of blood samples with different dilutions (1:10 to 1:1), blood/reagent ratio, incubation times (10-40 min), and temperatures (RT, 37 C) were tested. FIG. 36 shows a histogram of detected tagged cells as a function of fluorescent intensity for sample A1 with a dilution of about 1:5 (25 µl blood, 2 µl CD4-PE, 123 µl PBS). The plot exhibits two peaks which are attributed to CD4 lymphocytes (the right peak) and CD4 monocytes (the left peak). This result is representative of a wide range of measurement conditions for this donor blood (i.e., for repeated measurements on the same sample and samples with modified sample preparation). The average absolute CD4 count was about 1800 CD4 cells per µl blood, with a variation of about ±6%. As those of ordinary skill in the art can appreciate, most deviations are probably result from maintenance and handling of the simply-constructed first fluidic chip 302 between the measurements and from sample segregation. The measured CD4 values for this sample are at the upper end, but within the expected range, for human blood. The relative count rate of lymphocytes and monocytes and, more importantly, the peak distance (intensity ratio) are in good agreement with data reported in the literature.

Figure 37:
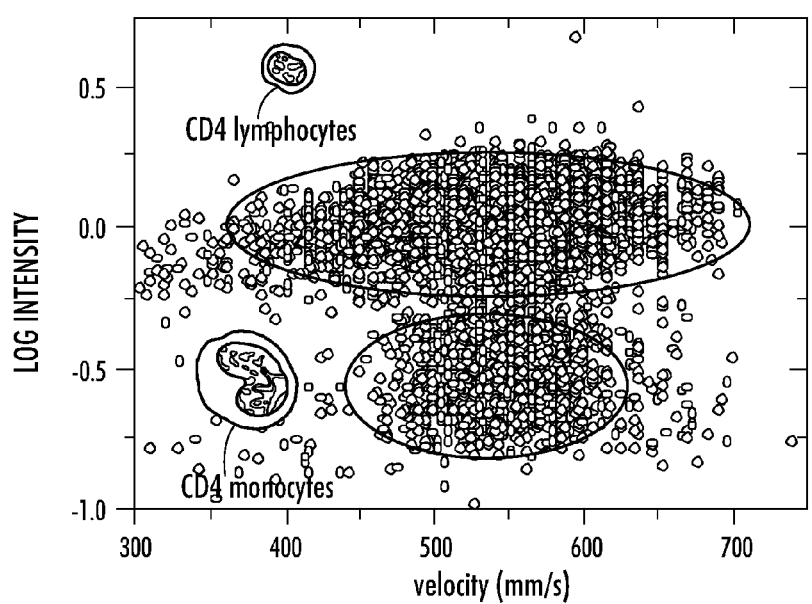
FIG. 37 illustrates measured fluorescent amplitude for each detected tagged cell as a function of particle speed for a blood sample containing CD4 lymphocytes and CD4 monocytes from data obtained using an experimental set-up substantially similar to that as shown in FIGS. 35A and 35B according to an embodiment of the present invention.

FIG. 37 shows the measured fluorescent amplitude for each detected cell in sample A1 as a function of particle speed for a total of about 11,000 detected cells. Details on the determination of amplitude and speed are given above. The detected cells separate into two groups that can be associated with CD4 lymphocytes and CD4 monocytes. Compared to the CD4 lymphocytes (about 7 µm), the larger CD4 monocytes (about 15 µm) show a narrower speed distribution as flow focusing constrains them to a narrower range of flow speeds in the center of the channel. The higher minimum speed for the monocytes of ~500 mm/s compared to ~400 mm/s for the lymphocytes reflects the repulsive force a cell experiences in the steep speed gradient near a channel wall. In summary, these results clearly demonstrate the accuracy of the spatially modulated emission technique to determine the velocity distribution of the particles.

Choosing a mask 88 with an appropriate minimum feature size will enable additional discrimination between lymphocytes and monocytes. Small features of mask 88 will be visible in the signatures (high-frequency features) for the smaller lymphocytes, but will be weak or absent in the monocyte signals. Therefore, the signature for a particular cell can be correlated with the expected signal for monocytes vs. lymphocytes to yield a better match. The spatially modulation technique offers several variables (intensity, speed, correlation) to discriminate between lymphocytes and monocytes.

Figure 38:
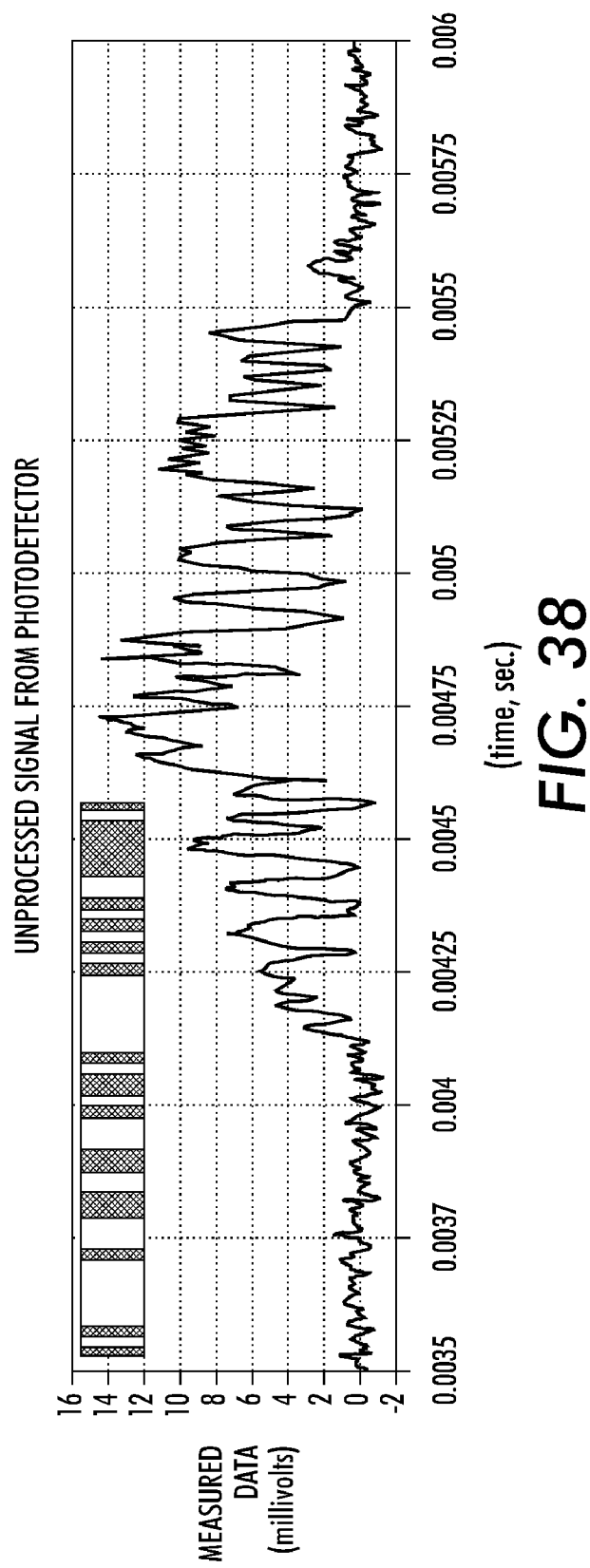
FIGS. 38-40 illustrate several screenshots of data acquisition in the experimental set-up substantially similar to that as shown in FIGS. 35A and 35B that illustrate the presence of two closely-spaced CD4 cells and their respective speeds.
Figure 39:
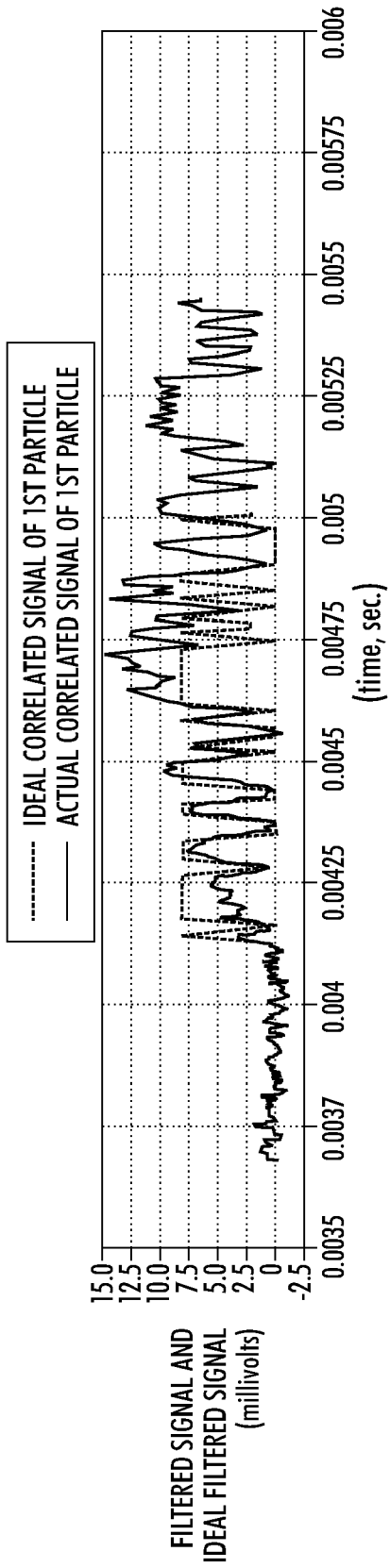
Figure 40:
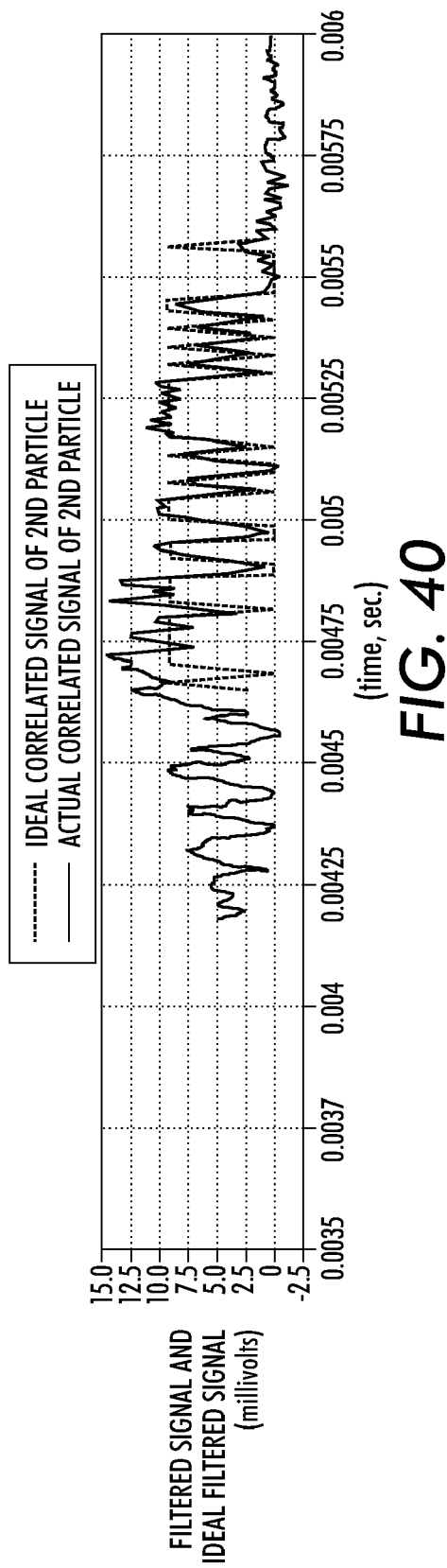

As a particular strength of the technique, and according to an exemplary embodiment, the correlation analysis yields the speed of each particle and can de-convolute signals from two particles that are in the sensing area at the same time. Coincident particles can be separately detected as long as their spatial separation is larger than the minimum feature size of the mask. Even particles with different intensities or velocities can be distinguished. Fluorescent beads have been detected that are in near coincidence with one order of magnitude difference in intensity. Those of ordinary skill in the art can appreciate that the demonstrated capability meets the needs for important medical applications such as CD4 counting. FIGS. 38-40 shows a signature from two closely-spaced CD4 cells. FIG. 38 is the raw data for the two particles; FIG. 39 illustrates both the correlation result that indicates a first particles' position (solid line), and the expected result (dotted line); similarly, FIG. 40 illustrates the correlation result that indicates a second particles' position (solid line), and the expected result (dotted line). With conventional data processing procedures, this event would be recorded as arising from a single cell. The correlation technique, however, clearly identifies two particles and yields their speed.

Absolute CD4+ counts can be used in the initiation and monitoring of antiretroviral therapy (ART) in HIV-infected adults. However in pediatric patients, the percentage CD4+ T-lymphocyte to white blood cell count value is a more useful parameter for monitoring HIV treatment, since its varies significantly less than the absolute CD4+ count. There is little consensus in the relevant art on which is the right method for measuring CD4 percentage (CD4%). To facilitate demonstration of prototype flow cytometer 300 according to an exemplary embodiment for measuring CD4%, a standard CD4 reagent (PE-CD4, PE/CY5-CD3 and known number of fluorescent micro beads), a recently introduced FACSCount CD4% reagent kit (BD model No. 339010 that consists of a single tube containing a mixture of three monoclonal antibodies, CD4/CD14/CD15, which were conjugated with PE/PE-Cy5/PE-Cy5, respectively), a nucleic acid dye, and a known number of fluorescent micro-beads were used. The antibody to CD14 recognizes a human monocyte/macrophage antigen, whereas the antibody to CD15 recognizes a human myelomonocytic antigen that is present on the majority of granulocytes.

Sample preparation was performed at both PARC and an external laboratory, for comparison. The recommended sample preparation protocol was followed. A standard two-color FACSCount reagent can be used to determine the total number of reference beads, CD4+ lymphocytes, and CD4– lymphocytes. The new CD4% reagent identifies lymphocytes by their DNA fluorescence and size while excluding non-lymphocytes (monocytes and granulocytes) by their CD14+/CD15+ expression. The CD4% is obtained from independent counts of CD4+ and CD4-lymphocytes, and the absolute CD4+ by comparison with the known concentration of reference beads.

Figure 41:
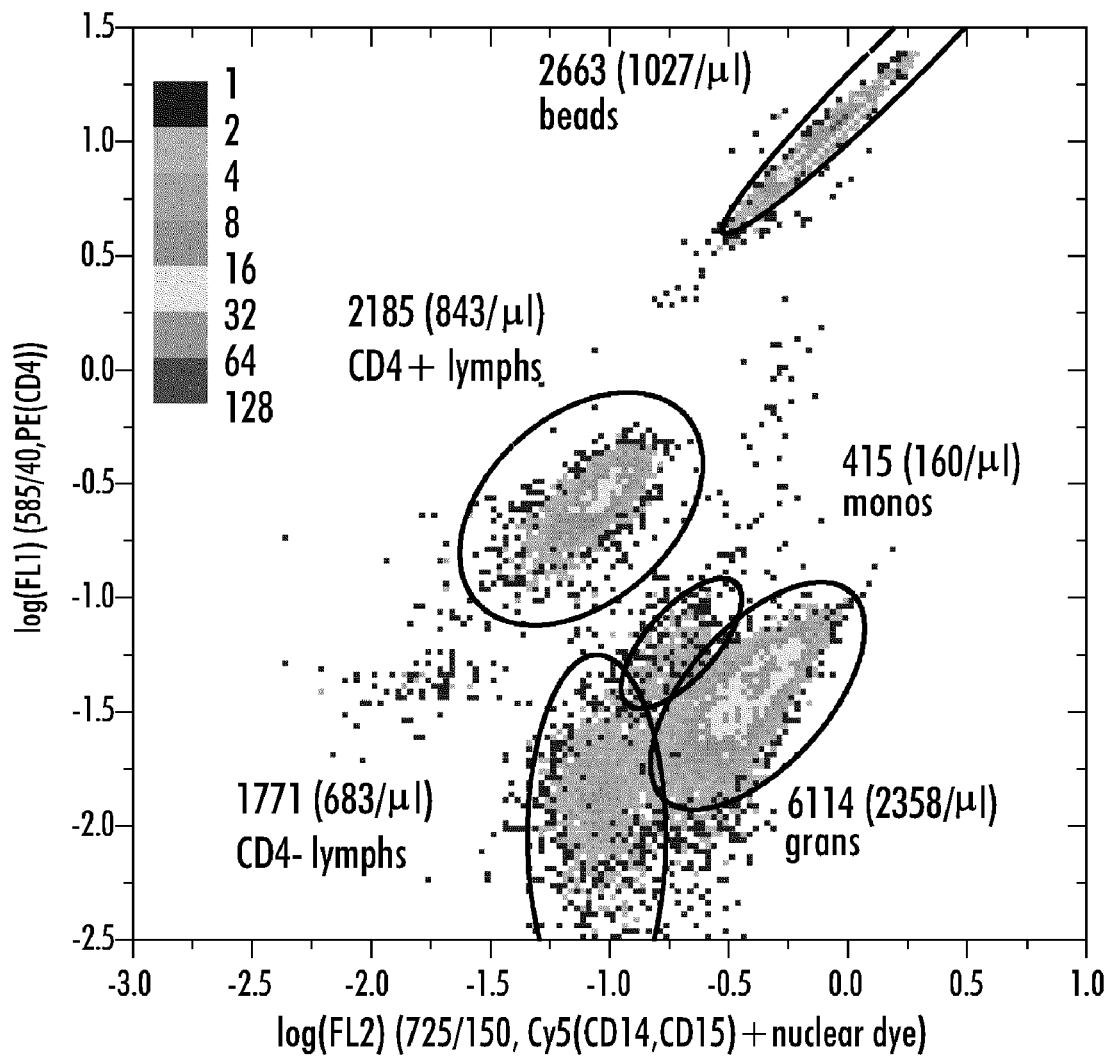
FIG. 41 illustrates a pattern for the major constituents of white blood cells obtained from whole blood obtained with a known reagent from data obtained using an experimental set-up substantially similar to that as shown in FIGS. 35A and 35B according to an embodiment of the present invention.

Attention is now directed towards FIG. 41. As those of ordinary skill in the are can appreciate, CD4 counting can be performed with a single fluorescence signal (e.g., from CD4-PE antibodies) on blood samples from average healthy persons, there are, however, many circumstances (e.g., co-infection with malaria, TB or other defective diseases, age of patient) in which distinguishing between CD4+ lymphocytes and monocytes is difficult or impossible. It is generally accepted in the medical community that for reliable CD4 diagnostics at least a two-color cytometer is needed to reliably obtain both absolute and percentage CD4.

FIG. 41 shows representative density plots obtained from a sample of whole blood that was stained with the BD CD4% reagent and evaluated in prototype flow cytometer 300 using the set up described above shown in FIG. 35. For this measurement two fluorescence signals were simultaneously recorded from the same detection area; they were recorded from opposite sides of first fluidic chip 302 with two array-type APDs 84 as discussed in greater detail below. A volume of about 30 µl of analyte containing about 3 µl of whole blood (specified protocol for the CD4% reagent) was measured within approximately 5 minutes. With improved data evaluation the data processing can be done simultaneously. As those of ordinary skill in the art can appreciate, accurately analyzing blood within a five minute time-frame provides the capability of reduced analysis time and/or improved data statistics.

FIG. 41 presents a pattern for the major constituents of white blood cells (WBC) obtained from whole blood stained with BD FACSCount reagent (BD#339010). The results in FIG. 41 were obtained using the spatial modulation technique according to an exemplary embodiment, and agrees very well with the expected pattern measured with a state of the art flow cytometer, e.g., with a FACSCount from BD Biosciences.

For a direct one-to-one comparison, measurements using prototype flow cytometer 300 according to an exemplary embodiment were benchmarked against measurements on the same samples obtained with a BD FACSCount. Excellent agreement for both absolute CD4 and CD4% was obtained between the two systems. Blood samples were prepared at an external laboratory with standard BD CD4 and CD4% protocols and reagents.

Although CD4 counting with a single fluorescence signal (e.g., from CD4-PE antibodies) can be informative for a segment of the population of reasonably healthy persons, there are many circumstances (e.g., age of patient, co-infection with malaria, TB or other infectious diseases) in which distinguishing between CD4+ lymphocytes and monocytes requires additional information. In these cases it is commonly understood that at least a two-color cytometer is needed for reliable CD4% diagnostics.

Accordingly, a compact two-color instrument can provide more complete diagnostics by including results that indicate both absolute CD4 and percentage CD4% (or CD4/CD8 ratio). According to an exemplary embodiment, prototype flow cytometer 300 can include two fluorescence photo detectors 83 on opposite sides of first fluidic chip 302 with a common excitation zone (see FIG. 35A). According to further exemplary embodiments, light beam 98 can be introduced in the plane of first fluidic chip 302. This can be realized either by an anti-resonant waveguide excitation as shown in FIG. 33, or by spot illumination at a shallow angle (e.g., by guiding the excitation light within the chip by total internal refection), as shown in FIGS. 35A, and 42-46 (both of which are discussed in detail below). Although providing light beam 98 to the excitation area 87 is more challenging when using anti-resonant waveguide excitation, experimental demonstrations have shown that the anti-resonant waveguide excitation works in the configurations of FIGS. 34, and 35 (although first fluidic chip 302 shown in FIG. 33 utilizes only a single photo detector 83, with the correct mask 88 (e.g. patterned color mask), it too can be used for CD4% count determination).

Figure 42:
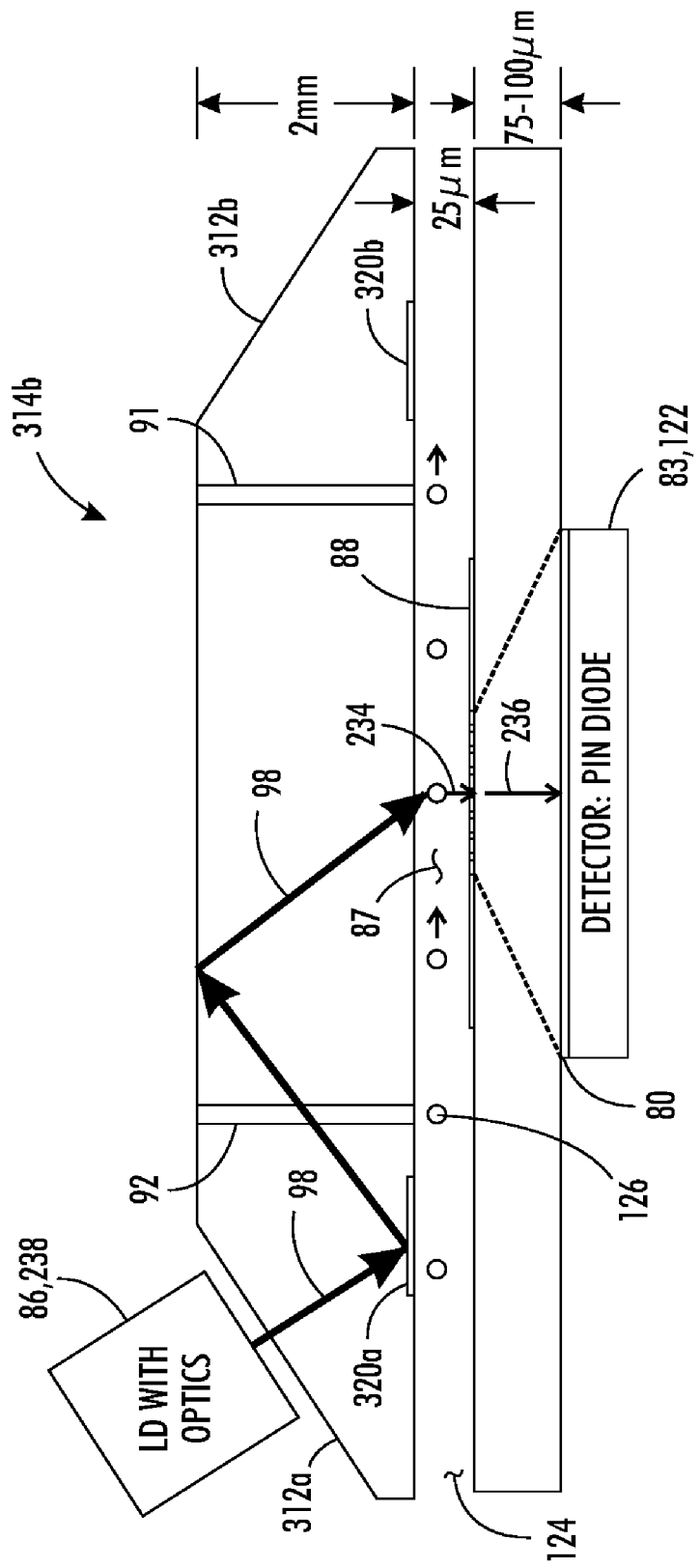
FIG. 42 illustrates a cut-away side view of an alternate embodiment of a fluidic-chip and part of a host-structure according to an alternate embodiment of the present invention.
Figure 43:
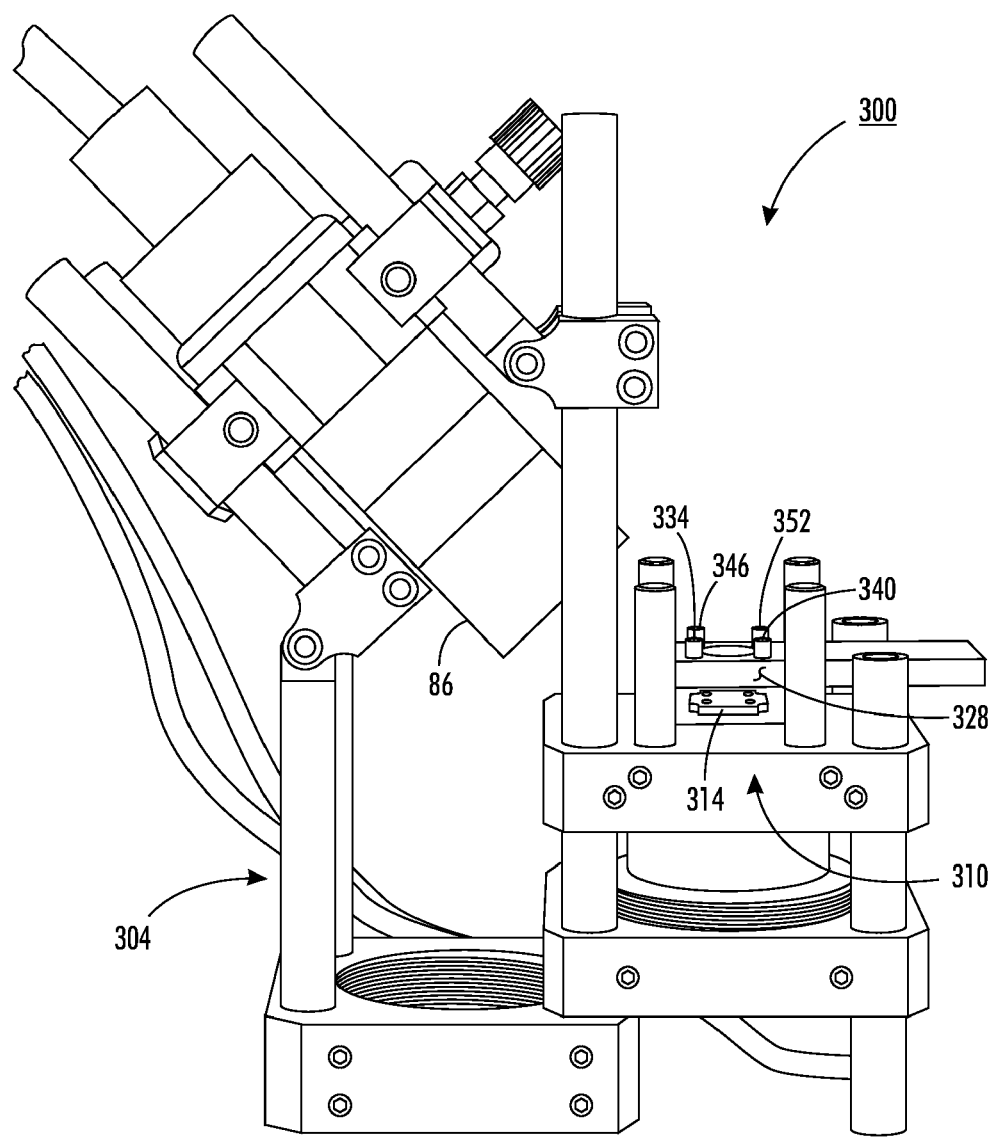
FIG. 43 illustrates a side view of a prototype flow cytometer with the alternate embodiment of the fluidic chip for detection of spatially modulated fluorescence shown in FIG. 42 according to an embodiment of the present invention.
Figure 44:
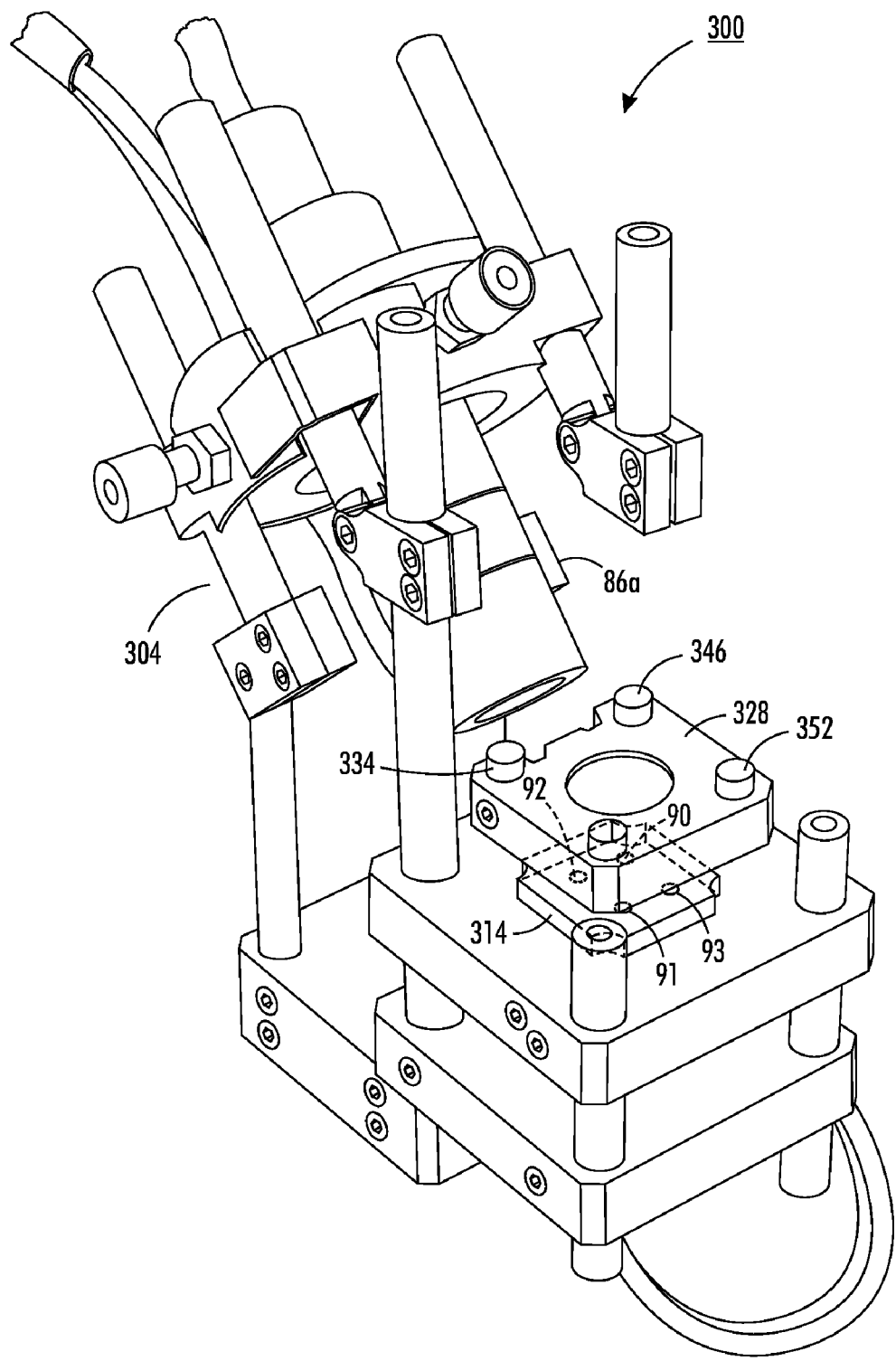
FIG. 44 illustrates a front perspective view of the prototype flow cytometer and fluidic chip as shown in FIG. 43.

Single parameter detection can be defined as detecting only a single fluorescence channel which is e.g., sufficient if only one type of object has to be counted (e.g. absolute CD4 which requires counting tagged CD4 cells. Attention is now directed towards FIGS. 42-46 that illustrate second fluidic chip 314 (see FIG. 42, a side view of second fluidic chip 314, and FIG. 45, a top perspective view of second fluidic chip 314) and prototype flow cytometer 300 according to an exemplary embodiment. Prototype flow cytometer 300 includes, as shown in FIGS. 43, 44 and 46, prototype host structure 304, and second fluidic chip 314. The compact, hand-held, prototype flow cytometer 300 as shown in FIG. 43 has been assembled with off-the-shelf components. The total size is about 5×3×2 inches. The largest component is a 50 mW, 532 nm laser module 86 that is directed through the polished end facet (light source interface 312a) of second fluidic chip 314 onto the approximately 2×0.1 mm excitation 87 area. According to an exemplary embodiment, second fluidic chip 314 is mounted directly on detection unit 310. Detection unit 310 can include collimator optics, a filter 80 for filtering out excitation light 98, and a compact PIN diode detector 122 in a TO5 header with integrated collection optics and integrated trans-impedance amplifier with a gain of about $10^7$ V/A, all of which can be housed within housing 342 shown in FIG. 46.

As discussed above, patterned mask 88 can be included in second fluidic chip 314, shown in FIG. 29. Therefore, according to an exemplary embodiment, no precise alignment between second fluidic chip 314 and detector unit 310 is required.

Alternatively, and according to a further exemplary embodiment, if mask 88 is not part of second fluidic chip 314, then it can be made part of second flow cytometer 300, and there will be self-alignment between prototype flow cytometer 300 and second fluidic chip 314. According to a further exemplary embodiment, if photo detector 83 and filter 80 are not part of second fluidic chip 314, then they can be made part of prototype flow cytometer 300 and it will become necessary to align second fluidic chip 314 and photo detector 83 such that encoded emanating light from mask 80 will reach photo detector 83 (through filter 80; an example of this configuration is shown in FIG. 42). According to an exemplary embodiment of prototype flow cytometer 300, however, the only alignment required is to direct laser light beam 98 to excitation area 87, and that alignment is relatively uncritical, because of the relatively large excitation area 87. Excitation area 87 is the area within which light beam 98 interacts with objects 126 and emanating light 234 can be detected by photo detector 83 after passing through mask 88 and becoming encoded emanating light 236. The whole unit can be powered by batteries (e.g., two nine volt batteries and two 1.5V C-type batteries), which is sufficient for at least a few hours of continuous operation).

Figure 45:
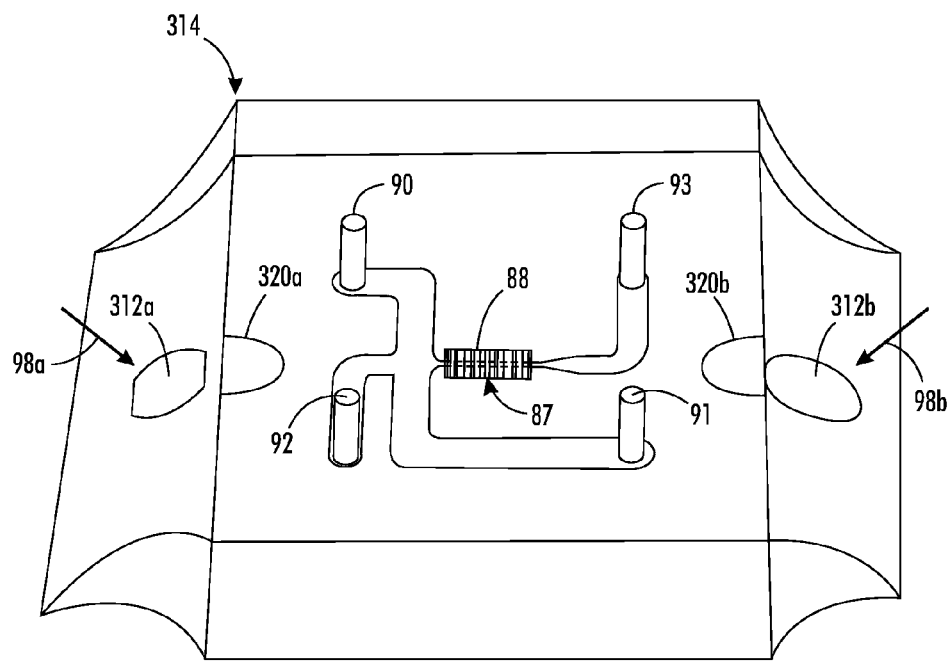
FIG. 45 illustrates a top perspective view of the fluidic chip for detection of spatially modulated fluorescence as shown in FIG. 42.
Figure 46:
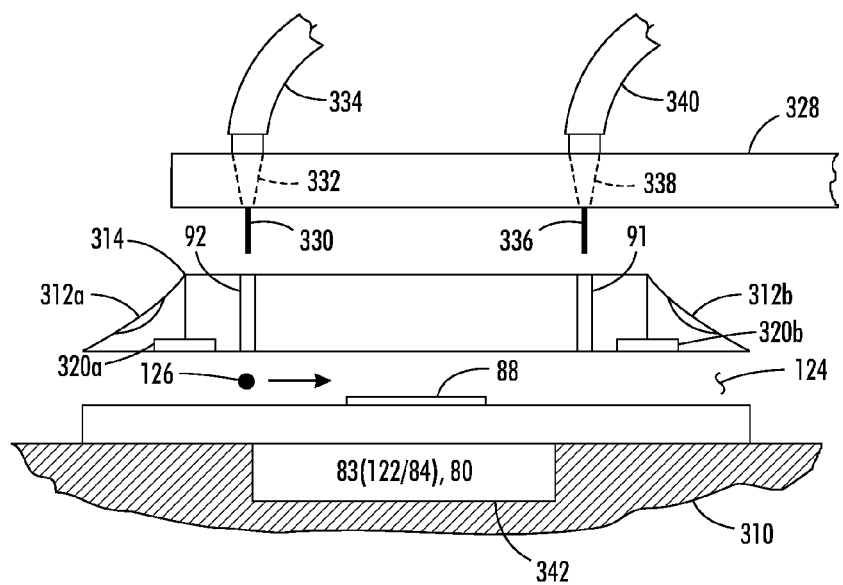
FIG. 46 illustrates a cut-away side view of the fluidic chip shown in FIGS. 42 and 45 and a portion of the prototype flow cytometer shown in FIGS. 43 and 44 according to an embodiment of the present invention.
Figure 57:
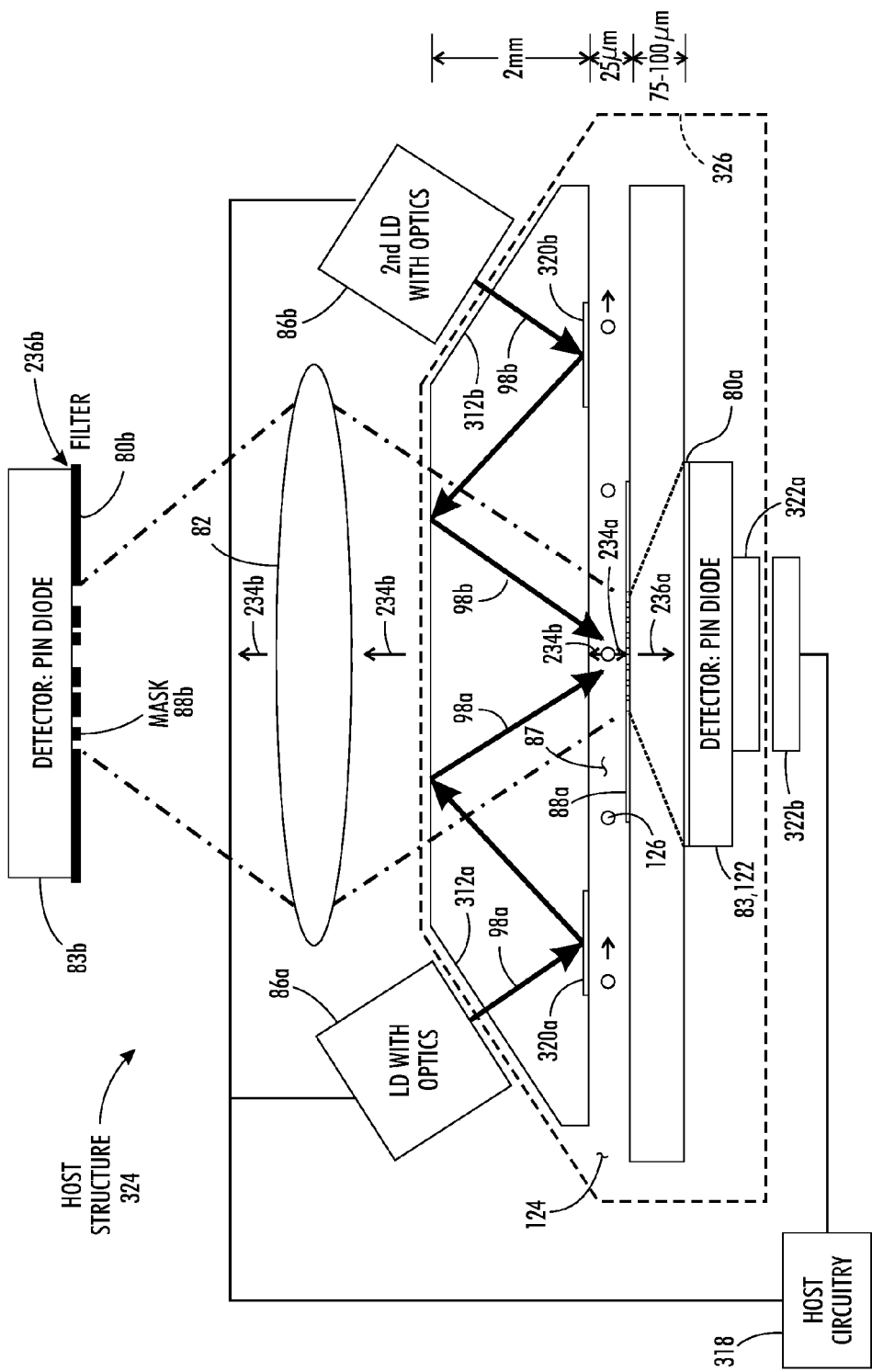
FIG. 57 illustrates a cut-away side view of alternate embodiment of a fluidic-chip and part of a host-structure according to an alternate embodiment of the present invention.

Second fluidic chip 314 (as well as third fluidic chip 236, shown and described in regard to FIG. 57), shown in FIGS. 42, 45 and 46, will be capable of being mass produced according to known manufacturing techniques (e.g., injection molding, hot embossing, among other techniques), the discussion of which is omitted for the dual purposes of clarity and conciseness. According to various exemplary embodiments, different techniques can be used fabricate the fluidic components, e.g., second fluidic chip 314 and third fluidic chip 326. For substrate material, quartz or glass slides can be used. The fluidic channel structure 124 of second and third fluidic chip 314, 326 can be constructed by (micro)-structuring suitable spacer materials such as SU8 photo resist, polydimethylsiloxane (PDMS) or special thin tape. The structuring of the spacer can be accomplished with laser processing, conventional photo lithography or micro-molding of PDMS on glass or quartz substrates. The channel structure can be sealed with cover slide, or with thermal bonding material, or gluing. As those of ordinary skill in the art can appreciate, fabrication methods to create a suitable flow cell include micro-structuring of thin adhesive tape (e.g., commercially available from 3M), with an automated laser processing tool. The tape can then be used as spacer material and to connect substrate and cover slide. Holes for the fluidic inlet and outlet can also be fabricated with the laser cutter or conventional drilling. Furthermore, masks 88 can be provided on a pre-structured substrate or produced during fabrication of second fluidic chip 314. Many suppliers are capable of integrating masks 88 with the required spatial resolution (10 μm) and size into second fluidic chips 314. Shown in FIG. 42, among other drawing figures, are several dimensions indicating approximate dimensions of several features of the fluidic chips; as those of ordinary skill in the art can appreciate, such dimensions are not meant to be in a limiting manner, and therefore should not be taken in a limiting manner, but instead represent one exemplary embodiment, and many possible other configurations are possible and within the scope of the exemplary embodiments of the fluidic chips and flow cytometers.

Additional embodiments of second (and third fluidic chip 314, 326 will be discussed in greater detail below in relation to the discussion of point-of-care (POC) flow cytometer 308, in reference to different configurations of masks 88, detectors 83, and filters 80.

A first exemplary embodiment of second fluidic chip 314, shown in FIG. 45, includes a first and second light source interface 312a, b, as well as a sheath fluid inlet 90, sheath fluid outlet 91, analyte inlet 92, and outlet 93; the same inlets and outlets apply equally as well to first fluidic chip 302.

Inlets 90, 92 and outlets 91, 93 of second fluidic chip 314 are designed according to an exemplary embodiment to fluidly interface with the needles of fluid manifold 328, which is a component of prototype flow cytometer 300. Fluid manifold 328 provides a fluidic interface between input fluids (analyte and possible sheath fluids) and second fluidic chip 314. Analyte input fluid 96 flows through analyte manifold input tube that is connected to analyte manifold input channel that is part of fluid manifold 328; analyte 96 the is output from fluid manifold 328 via analyte manifold output needle 350 that fits within analyte inlet 92 of second fluidic chip 314. A substantially similar arrangement is present for sheath fluid 94 (tube, channel, needle, inlet). On the output side, a similar needle for the analyte, analyte manifold output needle 350 fits within analyte outlet 93, and the output analyte 96 flows through analyte outlet 93, analyte output needle 350, analyte manifold output channel 352, and analyte manifold output tube 354 to a waste collector, not shown. A substantially similar arrangement is present for the output of sheath fluid 94. In addition, fluid manifold 328 facilitates retention and placement of second fluidic chip 314 on detection unit 310 of prototype flow cytometer 300.

For production versions of prototype flow cytometer 300 (i.e., third flow cytometer 308, discussed in detail below), it is expected that laser module can be replaced with a low-cost laser diode 238 or LED 240. Furthermore, advantage can be taken in regard to volume discounts on components, and volume discounts in terms of production. Therefore, it does not appear unrealistic to expect a unit manufacturing cost target for a hand-held POC flow cytometer 308 to cost at or about $300. The anticipated price target is extremely favorable in comparison with that of any commercially available or publicly announced device. Additional enhancements can include a personal digital assistant (PDA) for data collection/evaluation, and/or a smart-phone to store/evaluate the date, and then transmit the raw and/or evaluated data to a central data collection unit.

Figure 47:
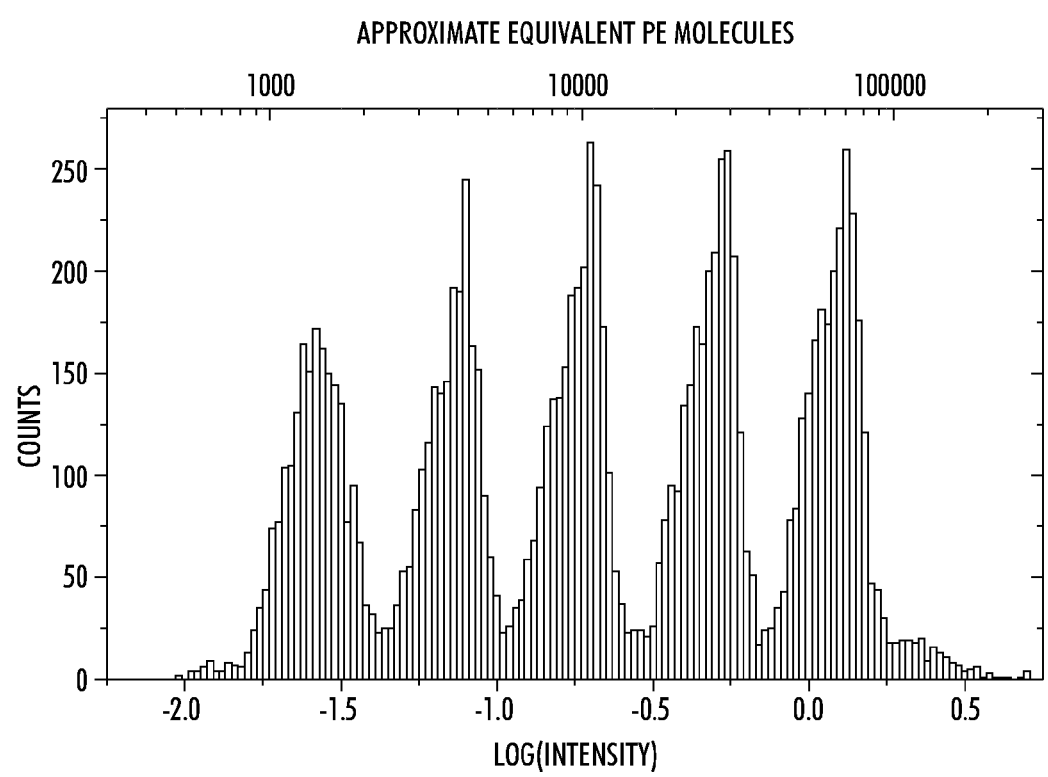
FIG. 47 illustrates an intensity histogram of a sample containing calibration beads from data obtained using the prototype flow cytometer shown in FIGS. 43 and 44.

Referring now to FIG. 47, results are shown for measurements conducted to verify the sensitivity and dynamic range of prototype flow cytometer 300. The measurements were conducted with 3.8-μm ultra-rainbow calibration beads (Spherotech) and yielded a detection limit ~$10^3$ MEPE, which is sufficient for reliable CD4 counts in whole blood and also meets the needs for a wide range of bio-particle-detection applications. With prototype flow cytometer 300 setup for single parameter detection and using a simple PIN diode detector 122, results for measured absolute and percentage CD4 (CD4/CD8 ratio) in whole blood are in good agreement with the measurements taken with a BD FACSCount from the same samples, indicating that the simple prototype made with off-the-shelf components, but using the exemplary methodology and design closely matched that of much more expensive flow cytometers.

According to a further exemplary embodiment, PIN diode detector 122, located within housing 342 (FIG. 46), can be replaced by an APD or array-type APD detector 84 (e.g., such as those manufactured by Hamamatsu Photonics, K.K., or SensL, Inc.) which only slightly increases the footprint of prototype flow cytometer 300, but would significantly increase analyte 96 through-put (currently about 5 μl/min) and sensitivity. Prototype flow cytometer 300, as shown in FIGS. 43, 44 and 46 with second fluidic chip 314 as shown in FIG. 45 that includes a black/white patterned mask 88, is a single parameter flow cytometer. By merely replacing black/white patterned shadow mask 88 with patterned color mask 242, a compact (hand-held), low-cost, two-color prototype flow cytometer 300 can be realized, and this is discussed in greater detail below.

The results shown in FIG. 47 clearly establish that the compact, low-cost second flow cytometer 306 can be realized by implementing the PARC spatial modulation technique according to an exemplary embodiment. Further evidence can be provided by considering that prototype flow cytometer 300 detected bacteria in the form of fluorescently stained E. coli ER2738. The signals obtained from the tagged bacteria are comparable to the signals detected from the stained CD4 cells.

Figure 49:
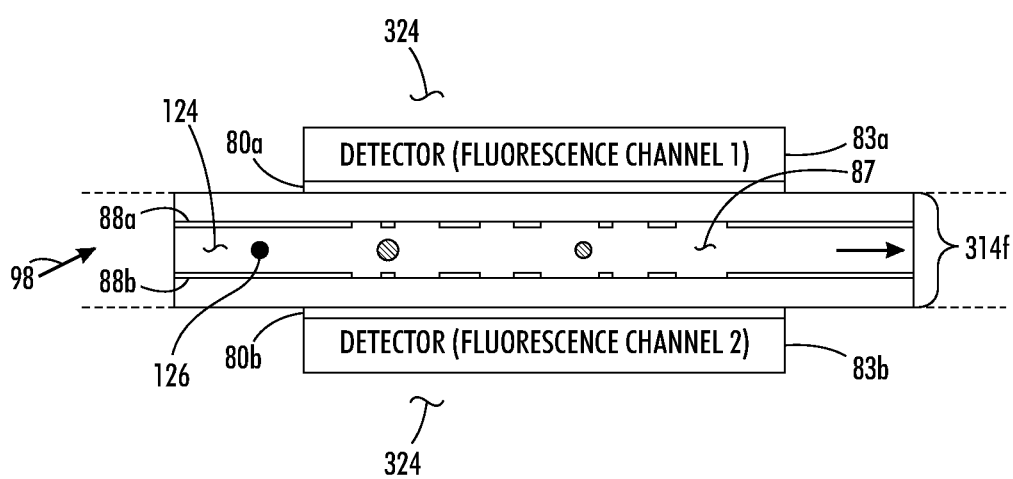
FIG. 49 illustrates a cut-away side view of an alternate embodiment of a fluidic-chip and part of a host-structure according to an alternate embodiment of the present invention.

Attention is again directed to FIGS. 43-46. Prototype flow cytometer 300, as shown in FIGS. 43, 44 and 46, can be used for single parameter detection (i.e., a single fluorescence channel). For many practical applications, however, at least 2-4 color detection is required. With slight modifications, prototype flow cytometer 300 can be configured to enable the detection of two fluorescence channels. For example, use of first fluidic chip 302 as shown in FIG. 49 can simultaneously record two fluorescence signals from the same detection area at opposite sides of first fluidic chip 302 (also as shown in FIG. 35). This has been discussed above in regard to two-color detection for CD4% measurements. In order to further improve the sensitivity of prototype flow cytometer 300, PIN diode detector 122 and integrated amplifier, located within housing 342 (FIG. 46), can be replaced with an array-type APD detector 84. According to an exemplary embodiment, replacement of PIN diode detector 122 with array-type APD detector 84 can increase the sensitivity of second flow cytometer 306 by a factor of 5× to 10×, while only slightly increasing the footprint of the instrument.

Referring now to FIGS. 43, and 44, manifold 328 can be used for anchoring second fluidic chip 314 (as shown in FIG. 45) with up to four fluidic ports. The different ports on second fluidic chip 314 can include sheath fluid inlet 90, sheath fluid outlet 91, analyte inlet 92, and fluid outlet 93 (through which both sheath fluid 94 (if used) and analyte 96 can exit second fluidic chip 314). Second fluidic chip 314 as shown in FIG. 45 can be inserted into second flow cytometer 306, as shown in FIGS. 43 and 44, and held in place by manifold 328 and one or more retaining screws. In addition, according to further exemplary embodiments, syringe pumps can be connected to second fluidic chip 314 of FIG. 29 to independently control the various fluidic ports (90, 91, 92, 93) to realize a broad variety of fluidic schemes (i.e., use of sheath fluid 94). Removal and replacement of second fluidic chip 314 is easily accomplished in regard to prototype flow cytometer 300. Prototype flow cytometer 300, as shown and described in reference to FIGS. 43, 44 and 46, is a hand-held unit that can be mounted to any suitable surface. As a hand-held unit, it was substantially easy to transport it for field testing.

Figure 48:
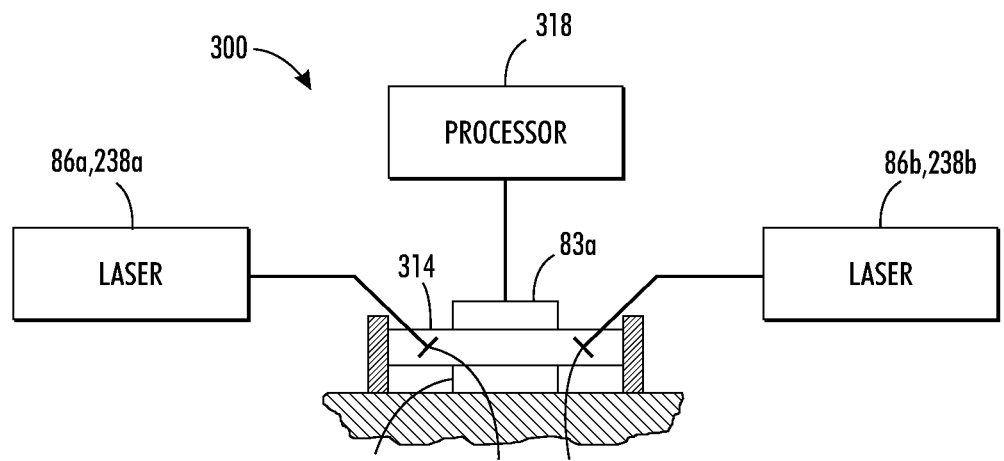
FIG. 48 illustrates a block diagram of the prototype flow cytometer shown in FIGS. 43 and 44 with an additional light source according to an embodiment of the present invention.

Furthermore, according to additional exemplary embodiments, additional laser excitation ports are available, as shown in the schematic diagram of FIG. 48. This experimental arrangement provides flexibility to apply various detection and excitation schemes to excitation area 87. The general schematic diagram of FIG. 48 includes second fluidic chip 314 using both first and second light source interfaces 312a, b, first and second light source 86a, b, host circuitry 318 (described in detail below for processing the outputs of first and second photo detectors 83a, b), and host structure 304, that, in the case of prototype flow cytometer 300, as shown in FIGS. 43, 44 and 46, includes hardware suitable for mounting light sources 86, photo detectors 83, detection unit 310, among other items.

Several different exemplary embodiments have been developed for two parameter detection. A first exemplary embodiment is direct sensing. In the direct sensing approach, according to an exemplary embodiment, photo detectors 83 are directly mounted to the wall of channels 124 of the fluidic chip to optimize the detection scheme, first with array-type APD detectors 84, and then with less-sensitive PIN diode detectors 122. For two-color excitation (e.g., second fluidic chip 314 as seen in FIG. 42, among others), optical filters 80 are selected to block first light beam 98a from detection by, or interfering with, second photo detector 83b (and visa-versa in regard to second light beam 98b, and first photo detector 83a).

A second exemplary embodiment is remote sensing. In the remote sensing approach, objects 126 in channel 124 are imaged onto a remotely positioned mask 88a attached to second photo detector 83a also, as shown in the prototype flow cytometer 300 schematic diagram of FIGS. 50, and 57. According to an exemplary embodiment the arrangement of filters 80, photo detectors 83, and masks 88 can be used in both prototype flow cytometer 300 (which is primarily a demonstration vehicle), and POC flow cytometer 308 (which can be a mass-produced, retail production device). According to an exemplary embodiment, the arrangement shown in FIG. 50 has the advantage of allowing patterned mask 88a to be exchanged easily because they are not integrated into second fluidic chip 314 (or third fluidic chip 326, discussed in greater detail below). According to further exemplary embodiments, the remote sensing arrangement also allows the use of and easy-exchange of, emission (interference or color) filter 80b, if required, to suppress light beam 98a from reaching or being detected by second photo detector 83b (and an interference filter 80a to suppress light beam 98b from reading or being detected by first photo detector 83a).

Figure 50:
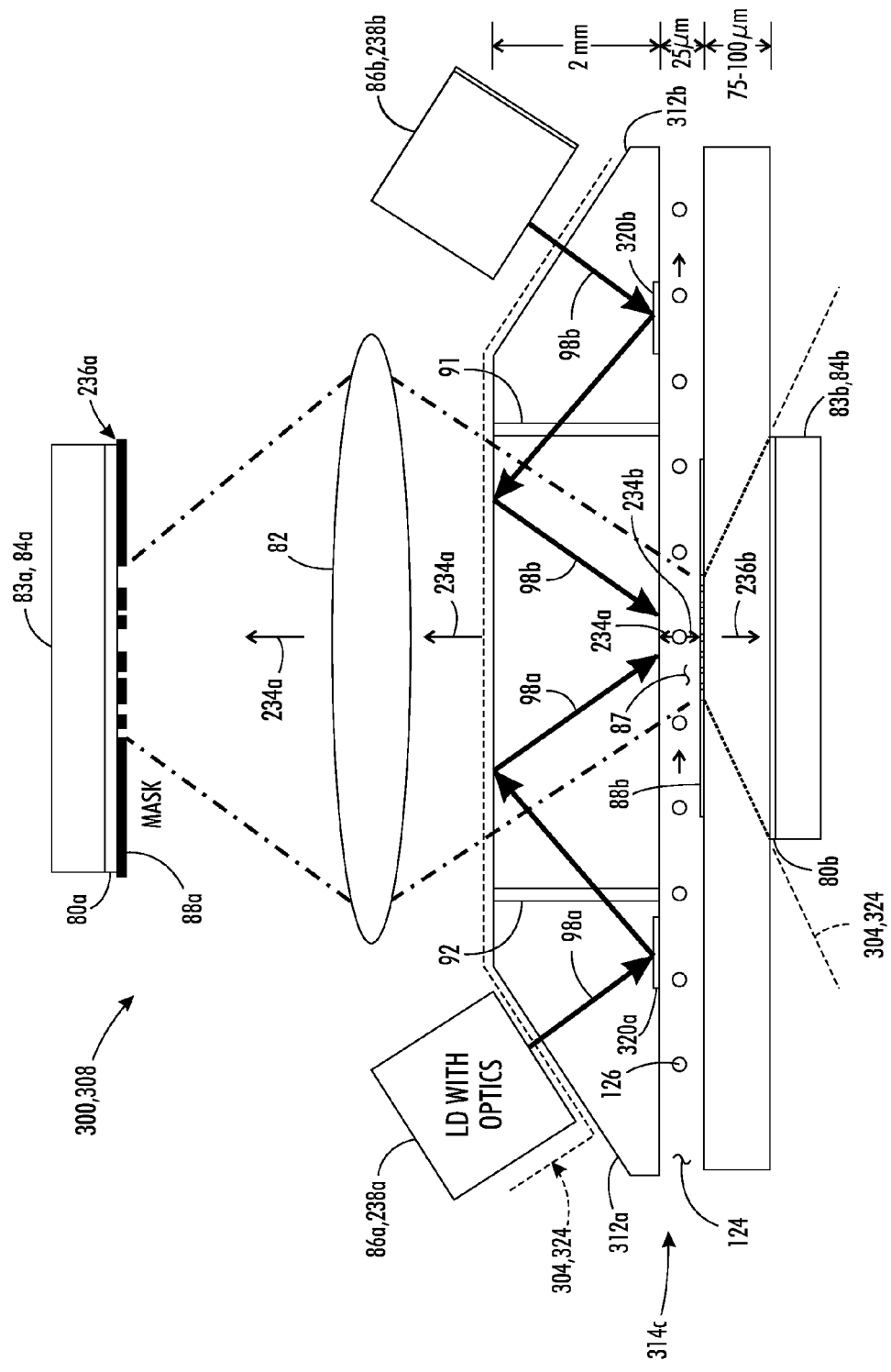
FIG. 50 illustrates a cut-away side view of an alternate embodiment of a fluidic-chip and part of a host-structure according to an alternate embodiment of the present invention.

In use, prototype flow cytometer 300 can provide two or four color detection depending on the type of masks 88a, b that are used in second fluidic chip 314 and within host structure 304. Light beam 98a, generated by either laser diode 238a (or a light emitting diode 240) can be internally reflected off first mirror 320a after entering second fluidic chip 314 through first light source interface 312a. Light beam 98b enters second fluidic chip 314b through second light source interface 312b, and is internally reflected by second mirror 320b; both first and second light beams 98a,b internally reflect against inner boundary surfaces of second fluidic chip 314b as shown FIG. 50 until they encounter objects 126 within channel 124. First and second emanating light 234a,b are generated, emanating in substantially all directions. In FIG. 50, first emanating light 234a is shown as only emanating upwards toward first mask 88a and first photo detector 83a. However, as those of ordinary skill in the art can appreciate, such would generally not be the case, as discussed above. Instead, first filter 88a will filter substantially all, or at least a significant portion, of any emanating light 234b that was generated from second light beam 98b. Thus, for the purpose of illustration only, first emanating light 234a is shown as emanating towards first photo detector 83a, and second emanating light 234b is shown as emanating towards second photo detector 83b.

First emanating light passes through second fluid chip 314 and into host 304 that includes lens 82. First emanating light 234a first encounters lens 82 that collimates emanating light 234a towards first detector 83a. First emanating light 234 then encounters first mask 88a.

First encoded light 236 emanates from first mask 88a, and enters first filter 80a, which, as discussed above, filters all or substantially all light generated by second light beam 98b. Because first photo detector 83a is located remotely from fluidic channel 124, this is the "remote sensing" aspect of second fluid chip 314 and prototype flow cytometer 300. The dashed lines in FIG. 50 encapsulates those components that can be included in prototype flow cytometer 300 (and also POC flow cytometer 308, as discussed in detail below). As discussed above, because first mask 88a is located remotely from excitation area 87 within channel 124, alignment between second fluidic chip 314 and host 304 is more critical than if only second photo detector 23b and second mask 88b (located on a wall of channel 124) were being used.

Second emanating light 234b encounters second mask 88b, producing second encoded light 236b, which is filtered by second filter 80b, and filtered second encoded light 236b is then detected by photo detector 83b. Second filter 80b and second photo detector 83b are included as part of host 304.

Although more precise alignment between first mask 88a and excitation area 87 is required than with second mask 88b and excitation area 87 in second fluidic chip 314 as shown in FIG. 42, substantially improved separation is provided between the two photo detectors, meaning there is less interference (i.e., "cross-talk") and the SNR can be improved using this configuration.

Figure 51:
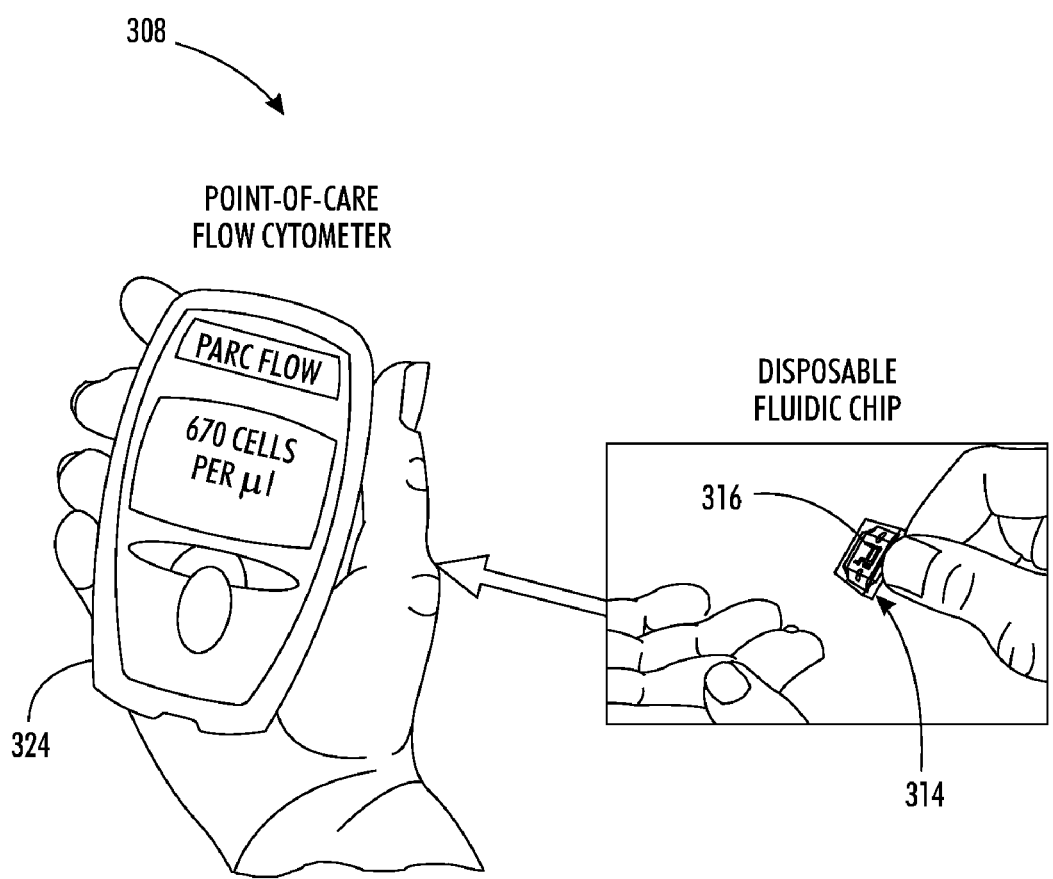
FIG. 51 illustrates a front perspective view of a commercial embodiment of a disposable fluidic-chip, and a handheld host-structure implemented as a point-of-care device for use with the disposable fluidic chip according to an embodiment of the present invention.

Attention is now directed towards FIG. 45 that illustrates second fluidic chip 314 and FIG. 51 that illustrates POC flow cytometer 308 according to an exemplary embodiment. POC flow cytometer 308 includes, as shown in FIG. 51, third host structure 324, second fluidic chip 314, and fluidic chip (chip) holder 316.

POC flow cytometer 308 is designed to be a commercial embodiment of prototype cytometer 300 designed and built in accordance with the exemplary embodiments described herein can be used in a variety of settings wherein large, commercial flow cytometers are plainly impractical, and/or unnecessary. Several examples of such uses were discussed in greater detail above, and need not be repeated here again. Attention is now directed towards FIG. 51, which shows POC flow cytometer 308 according to an exemplary embodiment; FIG. 45 which shows a first exemplary embodiment of second fluidic chip 314 that can be located in chip holder 316, and FIGS. 52 and 53 that are top and side views of the POC flow cytometer 308 and production fluidic chip 314 according to further exemplary embodiments, FIG. 54, which is a block diagram of second fluidic chip 314 and third flow cytometer 308 being loaded with analyte 96, FIGS. 42, 45, 50, 55, and 56, which are schematic representations of second fluidic chip 314 according to different exemplary embodiments, and FIG. 57, which is a schematic representation of third fluidic chip 326, are discussed in greater detail below.

As discussed in greater detail above, there is a great need for portable, reliable, user-friendly and inexpensive CD4 monitors for healthcare workers in the field, as well as more sophisticated, inexpensive bench-top devices for rural clinics. The extension of spatial modulation techniques to patterned multicolor filter arrangements according to various exemplary embodiments discussed herein will allow compact "high-end" point-of-care (POC) flow cytometers 308 to address a large variety of demanding medical applications that typically require high-performance laboratory flow cytometers capable of multi-parameter measurement. In conjunction with more elaborate mask 88 designs (e.g., superimposed masks), substantially precise characterization of spectral features for (tag-free) object identification can be accomplished.

Figure 52:
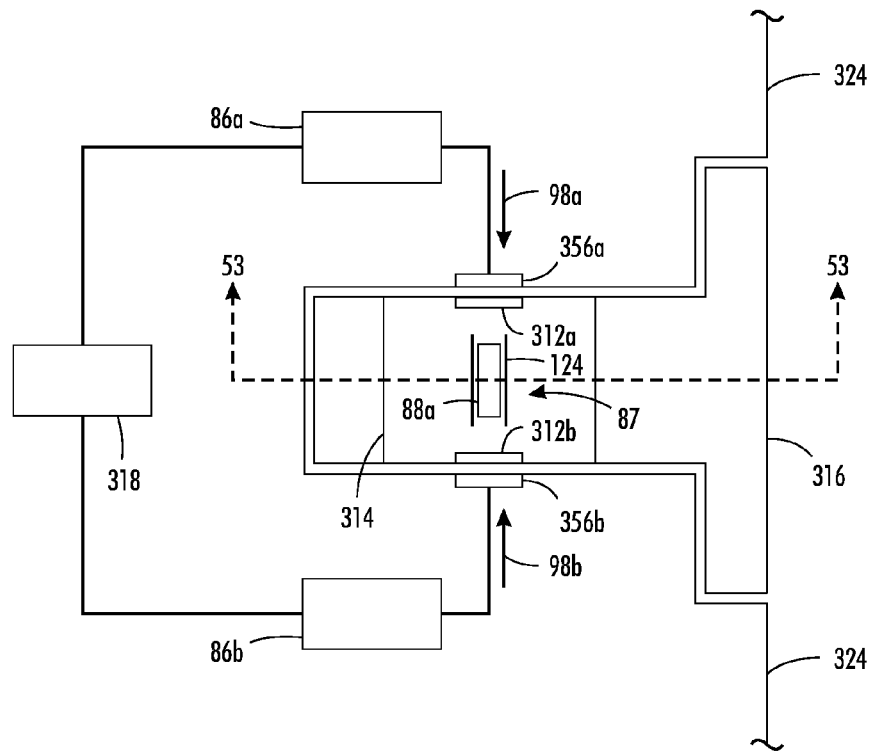
FIG. 52 is a partial cut-away top view of the point-of-care flow cytometer and disposable fluidic chip as shown in FIG. 51.
Figure 53:
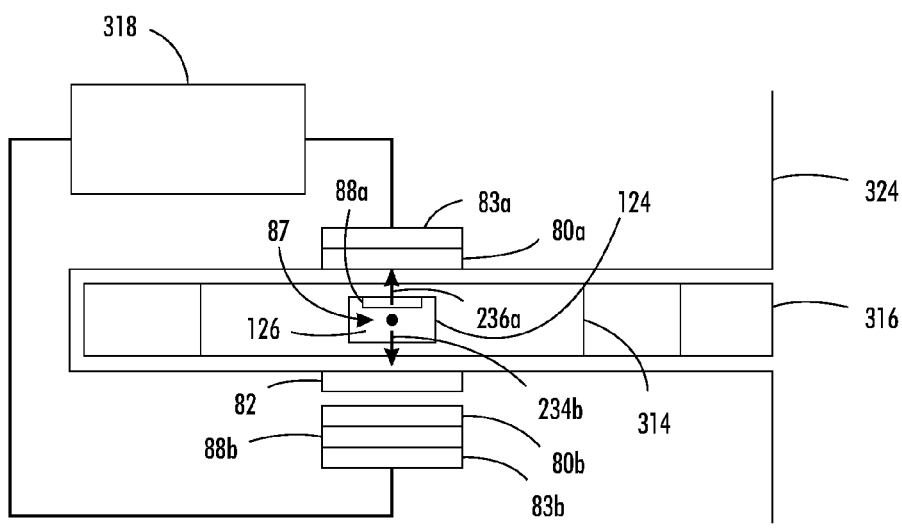
FIG. 53 is a partial cut-away side view of the point-of-care flow cytometer and disposable fluidic chip as shown in FIG. 51.

FIG. 51 shows a first exemplary embodiment of POC flow cytometer 308. In use, after taking a small analyte 96 volume (e.g., a sample of blood, not shown), a disposable production second fluidic chip 314 (that is held by fluidic chip holder (chip holder) 316), can be inserted into POC flow cytometer 308 in such a way that excitation area 87 is located between light source 86 and photo detector 83. FIGS. 52 and 53 are top and side cut-away view of POC flow cytometer 308 and second fluidic chip 314 that illustrate the interface between second fluidic chip 314, and POC flow cytometer 308 according to an exemplary embodiment. Positioning accuracy between POC flow cytometer 308 and second fluidic chip is relatively uncritical, so that placement between POC flow cytometer 308 and second fluidic chip 314 (and third fluidic chip 326) within about 100 μm is all that is necessary for accurate counting and detection.

Figure 58:
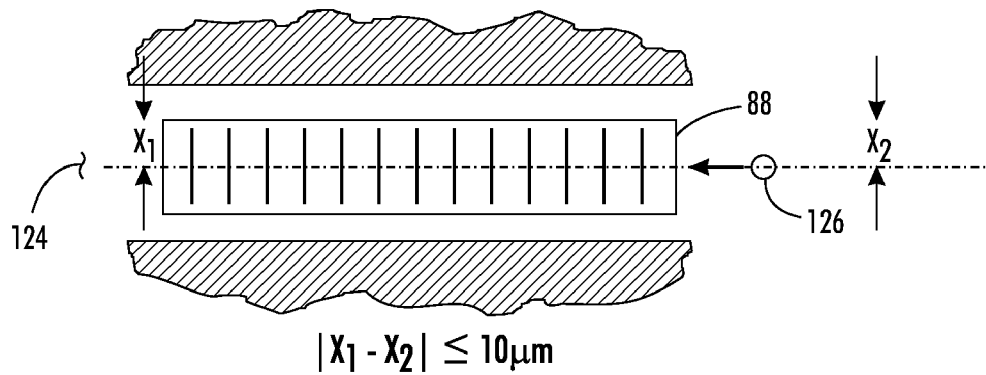
FIG. 58 illustrates a top view of a filter mask and channel of a fluidic chip indicating alignment along a centerline of the channel according to an embodiment of the present invention.
Figure 59:
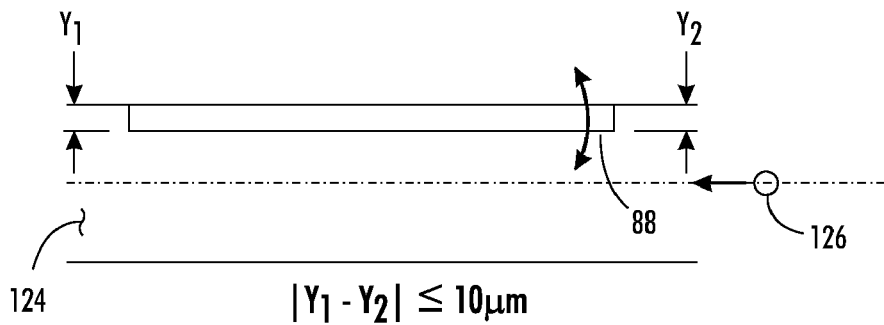
FIG. 59 illustrates a side view of a filter mask and channel of a fluidic chip indicating alignment along an upper boundary portion of the channel according to an embodiment of the present invention.
Figure 60:
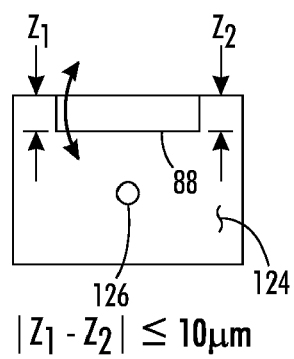
FIG. 60 illustrates a front view of a filter mask and channel of a fluidic chip in the direction of flow of the fluid indicating alignment along an upper boundary portion of the channel according to an embodiment of the present invention.

Substantially all of the various embodiments of second and third fluidic chips 314, 326 (third fluidic chip 326 is shown in FIG. 57) should align channel 124 with mask 88 to within about 10 μm; as those of ordinary skill in the art can appreciate, such alignment tolerances can be readily accomplished during fabrication of both second fluidic chip 314 and third fluidic chip 326. FIGS. 58-60 illustrate the 10 μm alignment tolerances: as shown in FIG. 58, a top view of channel 124 and mask 88, the 10 μm tolerance means that mask 88 should be aligned with an imaginary centerline of channel 124 such that the absolute different between $x_1$ and $x_2$ is less than or about 10 μm (meaning it must be parallel to the path of the centerline to within about 10 μm); as shown in FIG. 59, a side view of channel 58, mask 88 is to be positioned such that the absolute difference between $y_1$ and $y_2$ is less than or about 10 μm (i.e., mask 88 should be parallel with respect to the imaginary centerline to within about 10 μm); and as shown in FIG. 60, which is a front view of channel 124, in the direction of the flow of object 126, mask 88 is to be positioned such that the absolute difference between $z_1$ and $z_2$ is less than or about 10 μm (i.e., mask 88 is not rotated, or placed at an angle as shown in FIG. 60). Furthermore, according to an alternate exemplary embodiment, self-alignment techniques can also be applied to further reduce manufacturing costs if desired.

Referring again to FIG. 52, a partial side view of POC flow cytometer 308 that includes third host structure 324 and second fluidic chip 314 in chip holder 316 is shown. According to an exemplary embodiment, chip holder 316 is generally "T" shaped, and relatively thin. Chip holder 316 can be slid into the properly sized and shaped receptacle in third host structure 324, and there can be a detent mechanism, or some other similarly operating type of mechanism, that holds/retains chip holder 316 within third host structure 324. As discussed above, self-alignment occurs between second fluidic chip 314 and third host structure 324, such that an substantially lossless optical path if formed between light source(s) 86 of third host structure 324, and light interface(s) 312 of second fluidic chip 314. In FIGS. 52 and 53, there are shown a first and second light sources, a first and second mask, and first and second photo detectors; this is done merely for the purpose of description, as second fluidic chip 314 can comprise a single mask, and photo detector and the remotely located mask 88b does not necessarily need to be utilized. In FIG. 52, first light beam 98a enters light source interface mate 356a that provides a substantially lossless interface between the waveguide that carries first light beam 98a and first light source interface 312a of second fluidic chip 314. Once first light beam 98a enters second fluidic chop 314, it can be internally reflected via first mirror 320a, or via internal reflections, as discussed in detail above, to channel 124 and excitation area 87. First mask 88a is shown as attached within channel 124. A substantially similar situation occurs with second light beam 98b, which is generate by second light source 86b. FIG. 52 illustrates that there are two such light sources 86a, b, and two such light interfaces 312a, b, and of course both need to be optically interfaced between the light sources and light interfaces. Both first and second light sources 86a, b are controlled by host circuitry 318.

In FIG. 53, a partial cut-away side view is shown, along lines 53-53 of FIG. 52. In this particular exemplary embodiment of second fluidic chip 314, first photo detector 83a, and first filter 80a are located within POC host 324, and are aligned with excitation area 87 and first mask 88a to receive encoded emanating light 236a from the fluorescing object 126. On the bottom portion of second fluidic chip 314 shown in FIG. 53, lens 82 captures and guides emanating light 234b from fluorescing particle 126, and focuses it onto second filter 80b and then through second mask 88b, thereby providing second encoded light 236b to second photo detector 83b. Filter 82, second filter 80b, and second mask 88b, are aligned with excitation area 87 to receive emanating light 234b from the fluorescing object 126. Because there are two light sources 86a, b filters 80a, b are necessary to block out unintended light from entering their respective photo detectors 83.

As mentioned above, the particular configurations of second fluidic chip 314 can vary depending upon the intended objects to be measured; one or both of masks 88 can be located on the fluidic chips, or one can be remotely located, as shown in FIGS. 50 and 57, or both can be remotely located. POC flow cytometers 308 can be fabricated to accept one or more of the different variations of fluidic chips according to exemplary embodiments. If one or more photo detectors are located on the fluidic chip, then an interface must be used to transfer the electrical signals output from the one or more photo detectors to the host circuitry, as is discussed in greater detail below.

As described above, filtering of excitation light 98 can be performed with a conventional absorption filter 80. Absorption filters are generally compatible with the detection mode discussed herein due to the high background signal tolerance of the detection method according to exemplary embodiments. Note that the measurement shown in FIG. 47 was taken with the handheld unit (FIGS. 43 and 44) by using a conventional color filter (Schott OG570). This is particular true if dyes with pronounced stokes shift are used, for instance, 530 nm excitation in combination with PE-Cy5 or PE-Cy7. Higher quality filters can also be used, or inexpensive relay optics can be introduced between detector 83 and channel 124. The use of relay optics allows use of interference-based filters in the parallel section of the optical path to block excitation light 98 more efficiently. The complexity and the costs (filter, optics) added to POC flow cytometer 308 will be modest as the relay optics can be of low quality and could even be incorporated into second fluidic chip 314 (or third fluidic chip 326, as shown in FIG. 57) via injection molding. According to an exemplary embodiment, and for purposes of illustration, and not limitation, BrightLine® interference band pass filters from Semrock provide a suppression of the excitation light of 5-6 orders of magnitude.

According to a further exemplary embodiment, there is a broad range of approaches to implement data acquisition, evaluation, storage, and display. For example, and for purposes of illustration, and not limitation, real-time data evaluation on FPGAs or similar chips can provide real-time results. Alternatively, the data could be acquisitioned first into an intermediate storage and then the evaluation could be performed downstream either with an integrated low-cost processor or externally on a separate device such as, in further exemplary embodiments, a laptop, PDA or i-phone. According to still further exemplary embodiments, wireless technologies can be implemented to allow for remote data acquisition and evaluation.

According to a further exemplary embodiment, there is a need to check for the integrity of reagents, for example, due to heat exposure, especially in resource poor environments. A first exemplary embodiment includes the option to add suitable calibration beads to the staining solution that are designed to degrade at the same rate as the actual reagents. This provides a means to measure the quality of the sample preparation, as the calibration beads would establish an internal reference that would allow POC flow cytometer 308 to qualify the accuracy of the measurement. According to an alternative embodiment, reagents can be used that do not degrade when exposed to heat, e.g., reagent dried out in disposable chip.

According to further exemplary embodiments, barriers can be used to prevent certain types of objects 126, in particular bio-objects, from coming too close to the surfaces of channel 124 in POC flow cytometer 308 wherein otherwise van der Waal's forces can become problematic, and cause adhesion. Adhesion can occur when the molecules are sufficiently close (between about 1 nm to about 10 nm) to any surface. According to further exemplary embodiments, both Fluorad and polyethylene glycol (PEG) coatings work well to reduce adhesion, and others may exist that work even better to substantially reduce or eliminate adhesion.

FIG. 51 illustrates a preferred implementation of an exemplary embodiment of POC flow cytometer 308 as a hand-held device. Through use of POC flow cytometer 308 as shown in FIG. 50-52, the medical practitioner will have a hand-held point-of-care flow cytometer that includes a readout unit, as well as self contained means for excitation of objects 126, detection of encoded emanating light 236, fluidic handling and data processing. According to an exemplary embodiment, analyte sample containing objects 126 is introduced to the POC flow cytometer 308 via an inserted disposable second fluidic chip 314 (or third fluidic chip 326), which can be designed for one-time use or finite multiple measurements. Of course, as those of ordinary skill in the art can appreciate, multiple re-uses of second fluidic chip 314 (or third fluidic chip 326) can lead to contamination unless due care is taken to prevent the same from happening, or wherein contamination is not of significant concern. Dependent on a trade-off between cost targets and ease of use, second fluidic chip 314 and third fluidic chip 326 can be designed to also incorporate sample preparation. The high effective sensitivity as well as the low analyte volume will significantly reduce the consumption of reagents. Accordingly, a estimate of cost per test (for absolute CD4 count) can be as low as $1/test, which includes manufacturing costs of second fluidic chip 314 (or third fluidic chip 326) and the reagents.

According to several exemplary embodiments of POC flow cytometer 308, there are many advantages to be realized: these include (a) high S/N discrimination and distributed excitation that allows use of low cost components, namely, LEDs, LDs and PIN photo-diodes, to achieve high performance, robustness, compactness, and low cost; (b) improvements in fluidic handling and sample preparation; (c) determination of the speed of individual particles, as well as their identity and position, to provide true volumetric determination in a simple fluidic system with no requirement for sheath flow, which also reduces waste; (d) a robust system that is substantially insensitive to background noise and that can simplify sample preparation and waste disposal through use of whole blood without lysing; (e) insensitivity to essentially uniform background noise from optical scattering and fluorescence from major constituents of whole blood; and (f) insensitivity to unbound dye, and use of low or no analyte dilution.

FIG. 45 shows production fluidic chip 314 illustrating the incorporation of a spatial mask 88. However, as discussed above, spatial (black and white) mask 88 can easily be replaced with a patterned color mask 88, which allows for multi-color detection with a single large-area detector 83. In such a configuration, the different fluorescence channel signals are obtained by correlating the same measured time-dependent signal with the different expected signals for each particle type, as discussed in greater detail above. FIGS. 45 and 46 also shows that a first path of excitation light can be through first light source interface 312a, and a second light source 86b can be incorporated to input second light beam 98b through second light source interface 312b. Incorporating first and second light source interfaces 312a,b means that two different excitation wavelengths can be used to create a two-wavelength excitation pattern in excitation area 87, or a single light source with a single excitation wavelength can be used to create an interference pattern. For implementations using a single light source 86 to create interference patterns, the channel geometry can be used to tailor the expected time-modulated signal. For example, a periodic interference pattern in combination with a tapered channel, used to create an accelerating particle speed in the detection zone, will produce an expected time modulated signal that is chirped rather than periodic as would be expected from the excitation pattern alone.

Figure 54:
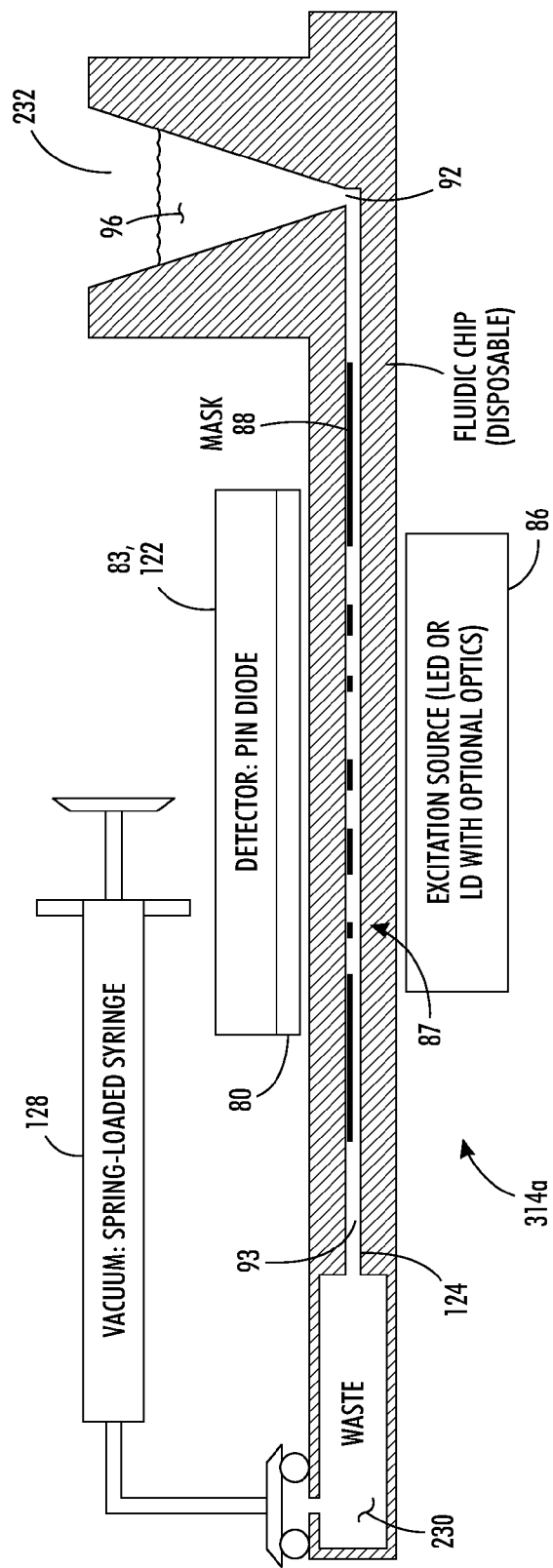
FIG. 54 illustrates a cut-away side view of an alternate embodiment of the fluidic-chip as shown in FIG. 45 with a sample and waste reservoir integrated within the fluidic-chip, according to an embodiment of the present invention.

Attention is now directed more specifically to FIG. 54, which is a block diagram of a first embodiment of second fluidic chip 314a that can be fabricated in the shape and form of second fluidic chip 314 shown in FIG. 45, and POC flow cytometer 308 being loaded with analyte 96 according to different exemplary embodiments.

FIG. 54 shows a schematic of a first embodiment of production fluidic chip 314a for the CD4 count. Disposable second fluidic chip 314a comprises a channel 124 with an integrated mask 88 on the inner wall of channel 124 that is closest to photo detector 83, sample reservoir 232 for holding analyte 96, waste reservoir 230 (for retaining sample liquid with analyte 96 after being measured), and an interface to connect second fluidic chip 314a to syringe 128 for drawing analyte 96 from sample reservoir 232 through channel 124 and into waste reservoir 230. The dimensions of second fluidic chip 314a shown in FIG. 54 (excluding pump and readout electronics), according to exemplary embodiments, will be approximately 2×1 cm² and the thickness will be approximately 1 mm. The sample reservoir 232 will have a capacity to hold about 30 µl of analyte 96. According to exemplary embodiments, disposable second fluidic chip 314a can be made from various types of plastics (e.g., TOPAS, PC, or PMMA) via injection molding or hot embossing. Both techniques will easily meet the required tolerances (+0.1 mm positioning accuracy of detection zone, ±2 µm for channel dimensions).

According to further exemplary embodiments, second fluidic chip 314a depicted in FIG. 54 illustrates measurement with pretreated samples; however, sample preparation can be accomplished on disposable second fluidic chip 314a according to an alternate exemplary embodiment, wherein it has been demonstrated that incubation times can be substantially reduced (by about 60×). Accordingly, advantages include supplying reagents from reservoirs on the disposable second fluidic chip 314a so that the operator only has to draw the blood sample into a capillary, thereby reducing errors arising from improper sample preparation. As those of skill in the art can appreciate, however, this technique would require more sophisticated fluidic handling which would add to the cost of the disposable second fluidic chip 314a, but would make POC flow cytometer 308 more robust against operator error.

The mechanism to insert second fluidic chip 314a into POC flow cytometer 308 can also be designed to properly engage syringe 128 (as shown in FIG. 54) and waste reservoir 232 (if not already integrated onto second fluidic chip 314a). Spring-loaded syringe 128 (with no consumption of battery power) can pump analyte fluid 96 through channel 124 in a few minutes, as discussed in greater detail above. A release button (not shown) for syringe 128 can be connected to light source 86, photo detector 83, and a real-time data evaluation system (consisting in part of host circuitry 318, to activate start of measurements). The real-time data evaluation system (host circuitry 318) can further optionally consist of one or more field-programmable gate array (FPGA) chips (which also can be part of host circuitry 318) and ultimately provide the user with a displayed result.

FIG. 42 is a schematic diagram of second fluidic chip 314b that can be fabricated in the shape and form as shown in FIG. 45. Light beam 98 enters first light source interface 312a, and is reflected off first mirror 320a into to an interior surface of a light transmissive region, and then back into excitation area 87 (of channel 124) that contains objects 126, wherein fluorescence occurs, resulting in emanating light 234. Emanating light 234 is received by mask 88, wherein spatial modulation occurs, and time varying information about objects 126 is contained in encoded emanating light 236. A substantially similar second fluidic chip 314c is shown in FIG. 50 (which also can be manufactured in the shape and form of second fluidic chip 314 as shown in FIG. 45), but this embodiment differs in that there are two light sources, 86a, b, with different wavelengths. Time sequential use, filtering, or a slight tilt between the optical paths of both light sources can be used to prevent unintentional cross talk or disturbance between both lasers. A second mirror 320b reflects second light beam 98b to the objects 126, substantially like first light beam 98a (as discussed above in regard to FIG. 42), and creates second emanating light 234b, that is focused by lens 82 to second mask 88b, resulting in second encoded emanating light 236b. Second encoded emanating light 236b is then filtered by second filter 80b, and then received by second photo detector 83b. As with second fluidic chip 314a of FIG. 42, the light sources, detectors, lens, and filters are all part of POC flow cytometer 308 according to an exemplary embodiment.

Figure 55:
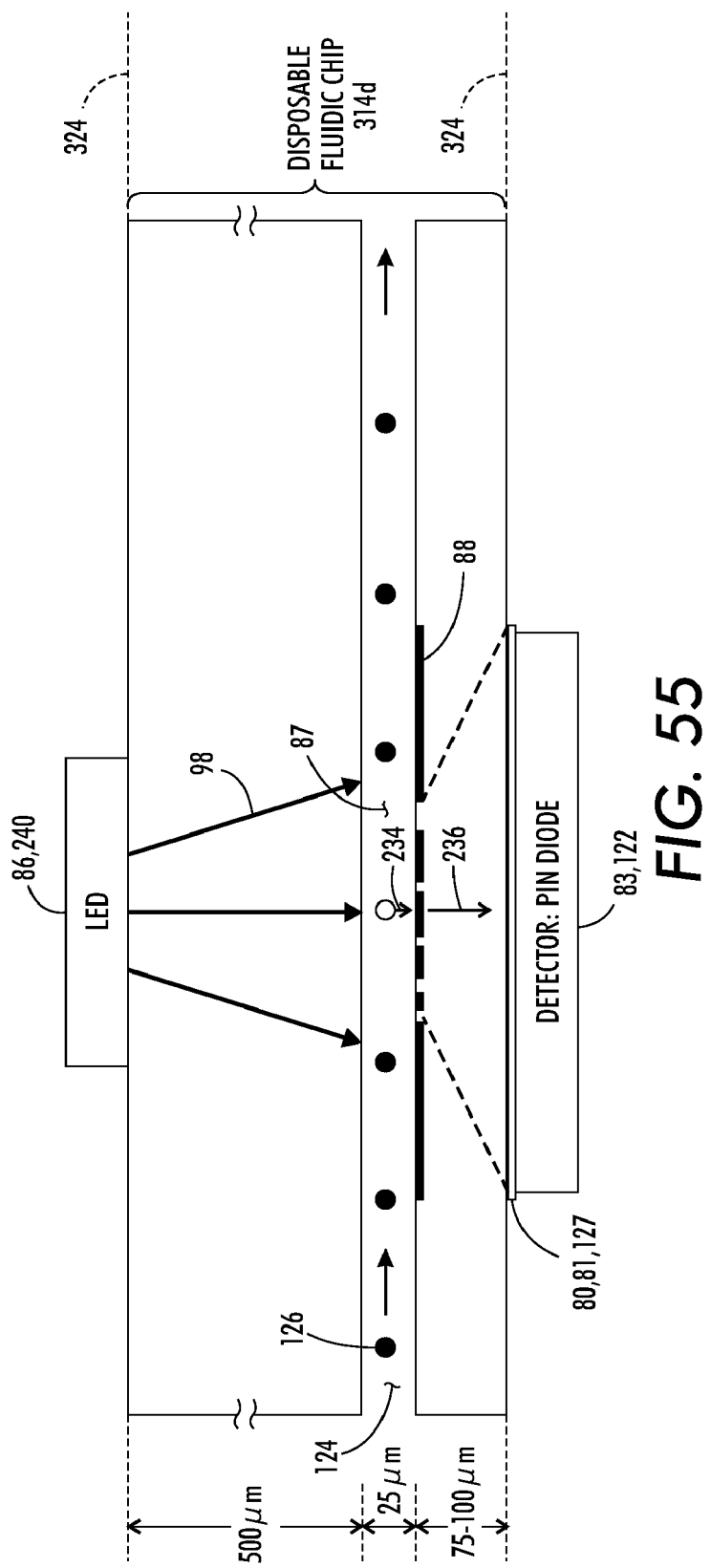
FIG. 55 illustrates a cut-away side view of alternate embodiment of a fluidic-chip and part of a host-structure according to an alternate embodiment of the present invention.

FIG. 55 is a schematic diagram of a fourth embodiment of second fluidic chip 314d that can be fabricated in the shape and form as shown in FIG. 45, and that utilizes a light emitting diode (LED) 240 as excitation light source 86. According to one exemplary embodiment, a large-area, high-power LED 240 (e.g., high brightness LEDs from Osram, Cree or Luminus, area: few mm$^2$, $\lambda$~530 nm, 5-30 W/cm$^2$) can be positioned within third host structure 324 to the outside surface of one channel wall of fourth fluidic chip 314d to introduce substantially highly uniform excitation along channel 124 over roughly one mm$^2$. In a first example of fourth fluidic chip 314d shown in FIG. 55, an off-the-shelf LED 240 was used, even though only about 20% of the LED 240 area was useable. In later configurations, custom LEDs 240 with an optimized area of about 0.1×1 mm$^2$ can be incorporated. Mask 88 is deposited on an inside surface of a wall of channel 124 on the side opposite to LED light source 240. Photo detector 83, according to a first exemplary embodiment can be a PIN diode detector 122 that includes an amplifier, and color filter 81 to block extraneous excitation light 98, both of which are attached to the outer channel wall.

As discussed, color filter 81, used in a bandpass configuration, can be used to block light beam 98 from LED 240 in the configuration where LED 240 is facing photo detector 83 (it is desired that only encoded emanating light 236 be received by PIN diode detector 122). According to an exemplary embodiment, the frequency and wavelength of light beam 98 will be sufficiently different from that of emanating light 234 and encoded emanating light 236, such that color filter 81 can allow substantially all of encoded emanating light 236 through to photo detector 83 (PIN diode detector 122), and substantially none of light beam 98 will pass through channel 124 and color filter 81 un-impeded. According to an exemplary embodiment, no significant differences exist between the use of simple color filters 81, and interference filters 127. The use of color filter 81 can be omitted if the lower part of the channel is fabricated from a suitable material (color filter). According to a further exemplary embodiment, the spatially modulated fluorescence emission detection technique is intrinsically insensitive to un-modulated background light (i.e., light beam 98 from light source 86, whatever type that it might be). The depth of channel 124 in fourth fluidic chip 314d is about 30 µm, and the mask 88 pattern is about 500×50 µm$^2$, with about a 10 µm minimum feature size. The width of channel 124 further depends on whether an embodiment utilizing sheath flow or a sheathless implementation is used.

Sheath flow, as those of ordinary skill in the art can appreciate, involves the flow of a first fluid (the sheath fluid 94) around a second fluid (analyte 96) that contains objects 126 that are being measured. The use of sheath fluid 94 provides many advantages including, but not limited to, analyte focusing, and separating the channel edges from excitation area 87, thus avoiding or at least substantially reducing the possibility of an additional source for scattering and background fluorescence. But, as those of skill in the art can further appreciate, sheath flow can make fluidic handling relatively more complex. According to an exemplary embodiment, POC flow cytometer 308 will use fourth fluidic chip 314d that does not involve or use sheath flow. Accordingly, the width of channel 124 in fourth fluidic chip 314d would be set to be at or about the width of spatial mask 88. Still further according to an exemplary embodiment, depending upon the typical concentration of cells under investigation, the channel width can be chosen to maintain an average cell distance in the detection zone that complies with the minimum cell distance the spatially modulated fluorescence emission detection technique can accommodate.

Taking by way of example only, and not in any limiting sense whatsoever, in CD4 counting, the typical upper limit for particle concentration (different types of white blood cells, reference beads) to be measured is about 8,000 cells per µl blood. Diluting the whole blood 1:2 with the antibody/dye and buffer solution and using a channel width of 50 µm would lead to an average of 2 cells in the detection volume at any given time during the measurement. For a pressure drop of 145 mbar along a 2 mm long rectangular (30 µm×50 µm) channel, the average flow speed would be about 0.33 m/s, and the throughput of the device would be 0.5 µl/s. For a statistically relevant initial blood sample of 10 µl (dilution 1:2→30 µl analyte), the total time for the measurement would be about 60 seconds. According to an exemplary embodiment, these measurements were performed with array-type APD detectors 84, and PIN diode detectors 122 in combination with a high-end, low noise amplifier (e.g., http://www.femto.de/index.html) that can provide the required amplification of about $2 \times 10^7$, with a sampling rate of about 200 kHz. According to further exemplary embodiments, however, a low cost transimpedance amplifier can be used that would require the reduction of the particle speed to be at or about 0.11 m/s and which will increase the time per test to about 180 seconds, or about three minutes. Further still, according to another exemplary embodiment, the measurements can also be preformed with little or no PBS dilution. According to a exemplary embodiment, minimizing the use of PBS dilution eases sample preparation and reduces uncertainty of the mixing ratio.

According to an exemplary embodiment, one advantage of the above described approach is the simplicity of the fluidic handling. Since the spatially modulated fluorescence emission detection technique yields concurrently both the fluorescent intensity of the particles and their speed distribution, it is possible to determine the actual flow rate and, therefore, the analyte volume from the data. Consequently, quantitative measurements do not require accurate flow control, and rather simple fluidic handling techniques can be used. This is in particular true for sheath-less implementations. Using sheath fluid 94 can introduce errors due to fluctuations of the ratio between sheath fluid 94 and analyte 96 and, therefore, requires more elaborate design of the fluidic channel 124. According to an exemplary embodiment, and as shown in FIG. 54 (discussed in greater detail above), fluidic handling can be as simple as connecting a spring operated syringe 128 to analyte outlet 93 and drawing analyte 96 from open well 232 through fluidic device 302 and channel 124 into waste reservoir 230. For applications where the duration of the measurement is less critical, according to further exemplary embodiments, gravity or capillary forces can be used to move analyte 96 through channel 124. According to a further exemplary embodiment, PIN diode detector 122 can be connected to a micro-processor, or a field-programmable gate array device (not shown) and data evaluation (through various algorithms) can be performed concurrently with the measurement.

Figure 56:
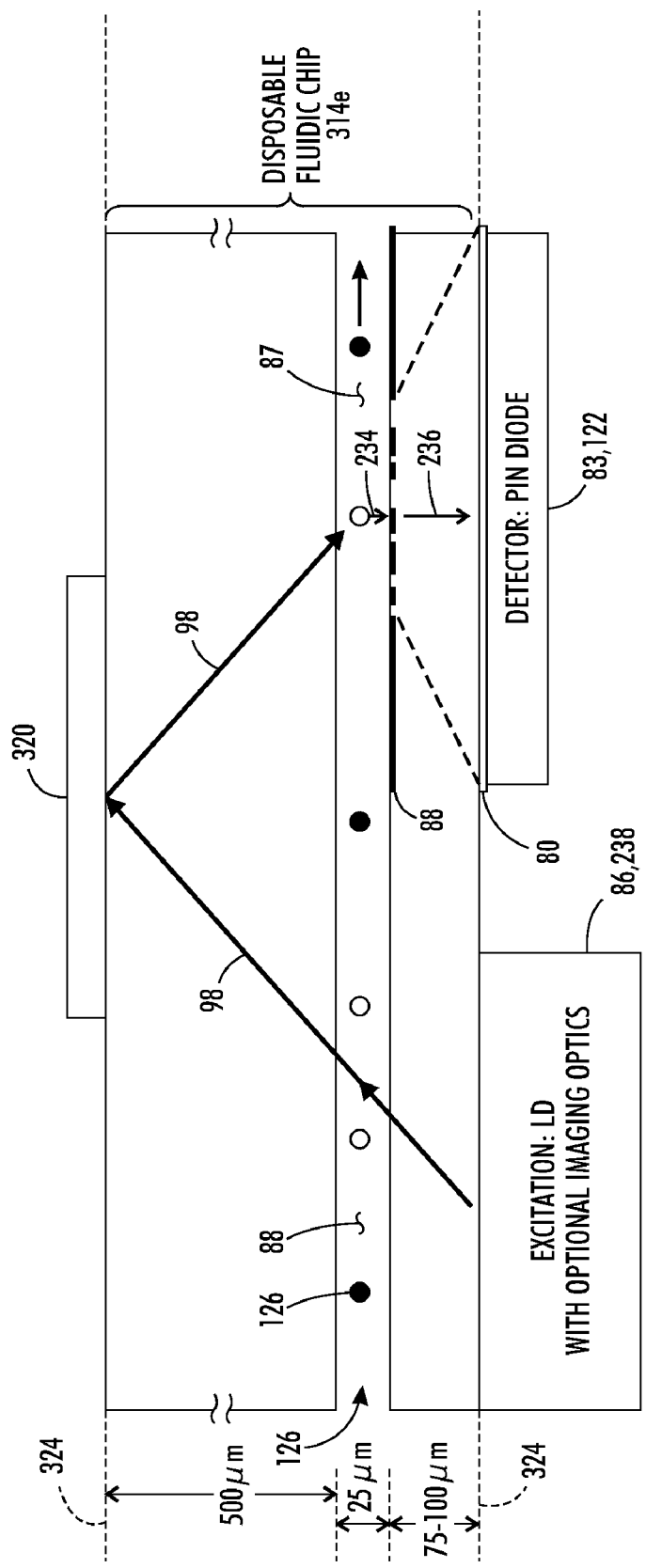
FIG. 56 illustrates a cut-away side view of alternate embodiment of a fluidic-chip and part of a host-structure according to an alternate embodiment of the present invention.

Through appropriate selection and design of mask 88, individual cells can be detected with the spatially modulated fluorescence emission detection technique. According to an exemplary embodiment, the minimum feature size of mask 88 is between about 10 μm to about 20 μm, and mask 88 is placed in close proximity to the cells in channel 124. As shown in the configurations of FIGS. 42 and 56 (FIG. 56 is discussed in detail below), mask 88 is deposited on an inside wall of channel 124. Due to the channel depth, about 30 μm, and the flow profile, the cells traverse the mask 88 at typical distances of between about 25 μm and about 5 μm. Accordingly, mask 88 will effectively modulate the fluorescent intensity recorded by PIN diode detector 122. It is important to note that the lateral alignment of PIN diode detector 122 and light source 86 with regard to channel 124 is not critical. The area of light source 86 and photo detector 83 simply need to overlap with the whole detection area defined by mask 88. According to an exemplary embodiment, this permits the use of disposable fourth fluidic chip 314*d* (or any of the other embodiments of second fluidic chip 314, or third fluidic chip 326) with rather low production tolerances. The required position accuracy between fourth fluidic chip 314*d*, photo detector 83, and light source 86 is only about 0.1 mm. Therefore, fourth fluidic chip 314*d* can be inserted between photo detector 83 and light source 86 by using simple self-aligning conical alignment marks.

Referring again to FIGS. 55 and 56, it can be seen that, according to an exemplary embodiment, the electro-optical components (filter 80, photo detector 83, and light source 86) are located in third host structure 324, and juxtaposed with the disposable fourth fluidic chip 314*d* (or fifth fluidic chip 314*e*) by inserting fourth fluidic chip 314*d*/fifth fluidic chip 314*e* into third host structure 324 (third host structure 324 can also be referred to as the "reader" as it contains the electro-optical components and signal processing circuitry according to a preferred exemplary embodiment). Since light source 86 and photo detector 83 are part of reader/host structure 324 and are not disposable, the cost constraints on these components are not as severe as for fourth fluidic chip 314*d*/fifth fluidic chip 314*e*. Accordingly, higher performance components can be used, and the inclusion of inexpensive relay optics as warranted. According to a further exemplary embodiment, relay optics (mirror) 320, as shown in FIG. 56, can be part of third host structure 324. Use of mirrors 320 provides for imaging of the high-brightness LED 240 onto excitation area 87 at an angle and strongly reduces the required filter performance since light source 86 (in this case LED 240) is no longer directly facing photo detector 83. According to a further exemplary embodiment, mirrors 320 can be made part of fifth fluidic chip 314*e* and be disposable as well.

FIG. 49 is a schematic diagram of a sixth embodiment of second fluidic chip 314*f* according to an exemplary embodiment that contains a first photo detector 83*a*, and a second photo detector 83*b*. First photo detector 83*a* can detect and distinguish different types of objects 126, and second photo (or additional detectors) 83*b* can be placed along the particle path to measure different absorption ratios. According to an exemplary embodiment, a first significant advantage of the technique described herein compared to conventional multi-color flow cytometry is that in the technique described herein, different light sources 86 excite analyte 96 at almost the same time and location and that is conducive to measuring differences in the excitation spectra with very high precision. According to further exemplary embodiments, substantially all errors induced by time-dependent factors such as bleaching, intermixing, and diffusion, as well as errors induced by differences in the excitation spot such as temperature gradients, and optical misalignment, are substantially eliminated.

Figure 61:
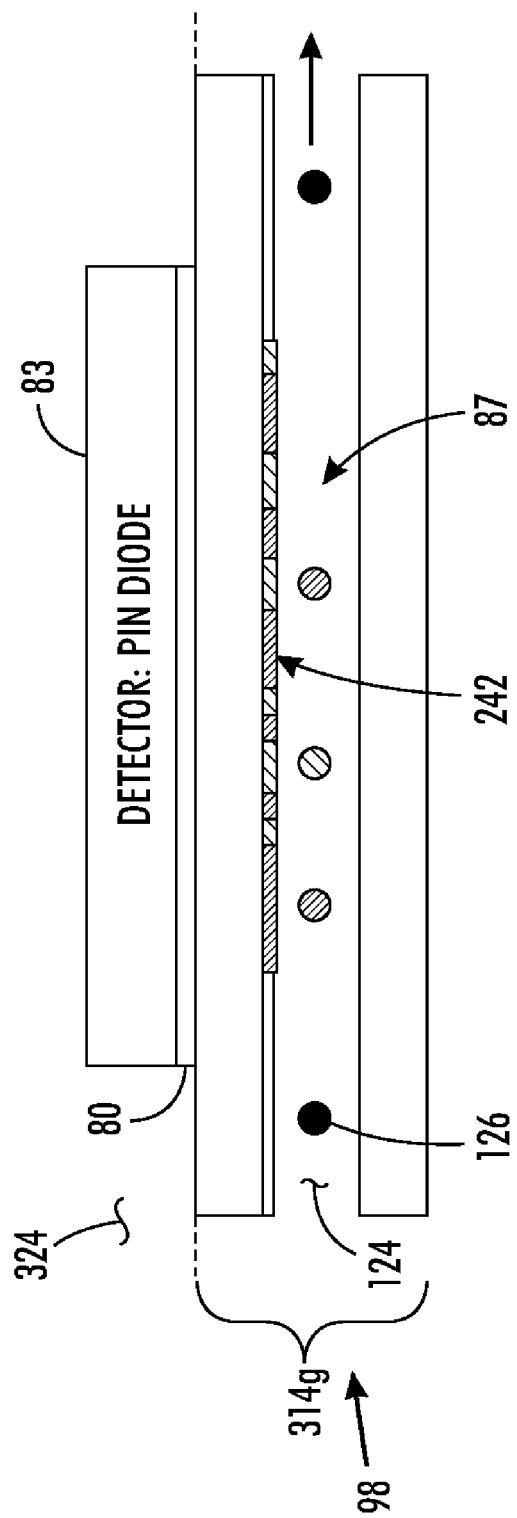
FIG. 61 illustrates a cut-away side view of alternate embodiment of a fluidic-chip and part of a host-structure according to an alternate embodiment of the present invention.
Figure 62:
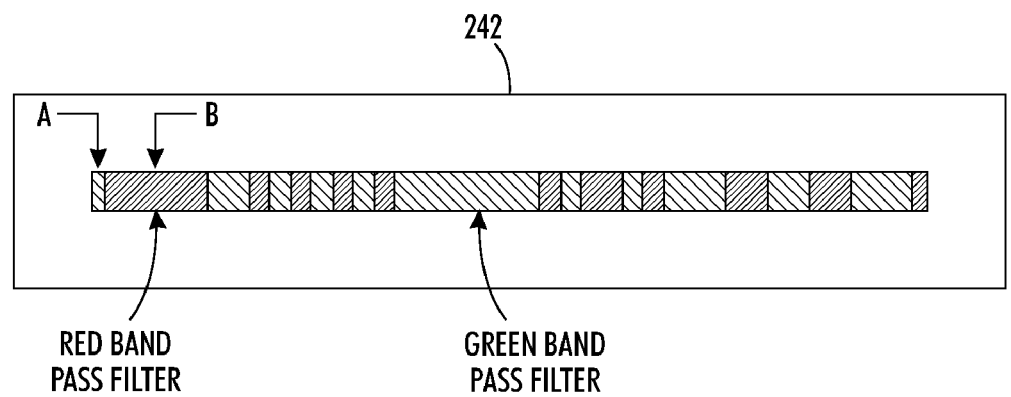
FIG. 62 illustrates a top view of a patterned colored mask filter-arrangement used in the fluidic-chip shown in FIG. 61.
Figure 63:
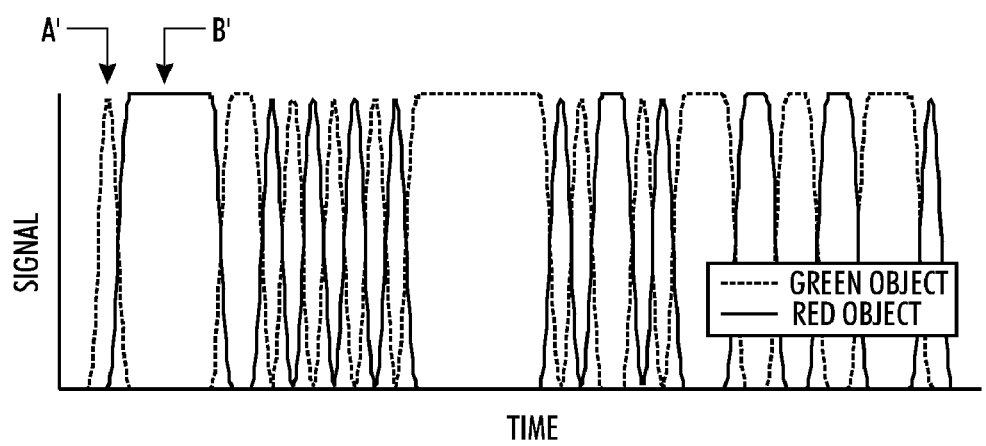
FIG. 63 illustrates complementary time-dependent, orthogonal detector signals of a red emitting particle and a green emitting particle according to an embodiment of the present invention.

Attention is directed towards FIGS. 61-63, which illustrate the basic concept of multicolor emission, and further illustrate a seventh embodiment of second fluidic chip 314*g* that can be manufactured in the same shape and form as second fluidic chip 314 as shown in FIG. 45. For multi-color emission detection, shadow mask 88 with binary transmission of 1 or 0) is replaced with patterned color band pass filter masks (color mask) 242 in order to be selective to different wavelengths ranges. FIG. 61 shows an exemplary embodiment of second fluidic chip 314*g* that allows detection of two colors (e.g., red and green) with pseudo-random patterns of red and green band pass filters. The red and green color mask 242 is shown in FIG. 62. According to a further exemplary embodiment, and dependent on the application, it can be favorable to use a pattern containing multiple band pass filters in order to allow for the simultaneous detection of multiple colors in the excitation area 87. In this configuration, the modulation of fluorescence optical output signal is caused by the specific spectral emission of object 126, and therefore, is necessarily color sensitive. The modulation depth (i.e., the difference between the non-normalized high and low intensities of the received encoded emanating light 236), as well as the resulting pattern of the output signal, contain wavelength information. For example, in second fluidic chip 314*g* that uses color mask 242 as shown in FIG. 62, red and green emitting objects 126a can produce complementary modulated patterns as shown in FIG. 63. In such a case the object color can be identified based on information obtained by correlation and, therefore, allows for reliable discrimination with high SNR after data processing in comparison to the SNR in the measured signal. Said another way, information contained in the absorption or emission spectrum of object 126 is encoded in the time-dependent signal. By using array-type detector 84 (e.g. array of pixilated APD as offered by SensL) combined with different spatially modulated color masks 242, many different objects 126 can be distinguished. Referring to FIGS. 62 and 63, note that for areas in FIG. 62 that show green band-pass areas (e.g., at the very left-most portion of color mask 242, in FIG. 62 (labeled "A")), there is a corresponding green object signal in FIG. 63 (e.g., at the very left most portion of the output signal diagram shown in FIG. 63 (labeled "A")). The "B" and "B'" designations point to a red band-pass area, and red object signal, respectfully.

According to an exemplary embodiment, multicolor excitation is realized by changing the wavelengths of the excitation within excitation area 87. Along the path of object 126, the wavelength is changed with a defined (periodic, chirped or pseudo-random) pattern. The resulting time-dependent signal (i.e., encoded emanating light 236), mainly reflects the excitation (absorption) difference of object 126 with respect to the different excitation wavelengths. For example, consider two types of objects 126 that absorb at two different excitation wavelengths. If the objects 126a, b have identical or similar emission behavior (i.e., efficiency and wavelength), this will result in complementary time-dependent detector signals similar to that shown in FIG. 63. An exemplary embodiment would be the combination of the dyes Pacific Orange and phycoerythrin (PE) that can be excited with 405 nm and 488 nm excitation lasers (i.e., light beams 98a, b), respectively. The emission of these dyes can be detected in the yellow/orange spectral range (e.g. 585 and 540 nm spectral ranges). Since the modulation depth of the signal depends on the absorption contrast at the two excitation wavelengths, even multiple particles exhibiting different absorption contrasts can be distinguished.

FIG. 57 is a schematic diagram of third fluidic chip 326 that can be fabricated in the shape and form of second fluidic chip 314 shown in FIG. 45. First light beam 98a enters first light source interface 312a, and is reflected off first mirror 320a and is then subsequently reflected off an interior surface of a light transmissive region, and back into excitation area 87 that contains objects 126, wherein fluorescence occurs, resulting in first emanating light 234a. First emanating light 234a is received by first mask 88a, wherein spatial modulation occurs, and time varying information about objects 126 is contained in first encoded emanating light 236a. First encoded emanating light 236a and any extraneous light from second light source 86b is then filtered by first filter 80a. A second light source 86b, with a different wavelength, transmits second light beam 98b, and a second mirror 320b reflects second light beam 98b to the objects 126, substantially similar to first light beam 98a (as discussed above), and creates second emanating light 234b, that is focused by lens 82 to second mask 88b, resulting in second encoded emanating light 236b. Second encoded emanating light 236b and any extraneous light from first light source 86a is then filtered by second filter 80b, and then received by second photo detector 83b. Both first and second light sources 86a, b, lens 82, and second filter are all part of POC flow cytometer 308 according to an exemplary embodiment. First detector 83a, first filter 80a, and first connector 322a are components of third fluidic chip 326. First connector 322a connects to second connector 322b to carry the electrical signals from first photo detector 83a to host circuitry 318.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. An article of manufacture, comprising:
a fluid-engaging structure, wherein the fluid-engaging structure includes
(a) a channel that in use can contain fluid and through which objects can move;
(b) one or more bounding parts that bound the channel, and wherein at least one of the one or more bounding parts include one or more light transmissive portions, wherein at least one of the one or more light transmissive portions is configured to receive excitation light and provide the received excitation light, and wherein excitation light enters the channel and interacts with an object resulting in emanating light; and
(c) one or more mask arrangements configured to receive at least part of the emanating light and in response, provide encoded emanating light,
wherein the one or more mask arrangements and the channel are further configured so that the encoded emanating light includes time variation resulting from relative movement between the one or more mask arrangements and the object, the time variation including information about the object;
wherein the fluid-engaging structure further comprises:
a first of the one or more mask arrangements configured to receive at least part of the emanating light and in response provide encoded emanating light to received emanating light, and is located on a first portion of the bounding parts;
one or more mirrors, at least one of the one or more mirrors configured to substantially reflect the excitation light through the one or more light transmissive portions; and
an internal reflecting surface, wherein the internal reflecting surface is configured to retransmit the reflected excitation light into the channel with the fluid and objects, and wherein
the article of manufacturing is configured for use with a host structure, and wherein the host structure includes:
at least one excitation light source;
a filter configured to receive and filter the encoded emanating light; and
a photo-sensor configured to receive the filtered encoded emanating light and detect time variation resulting from relative movement between the one or more mask arrangements and the objects, the time variation including information about the objects, and wherein the photosensor is further configured to provide an electrical signal indicating one or more sensed time-varying waveforms.

2. An article of manufacture, comprising:
a fluid-engaging structure, wherein the fluid-engaging structure includes
(a) a channel that in use can contain fluid and through which objects can move;
(b) one or more bounding parts that bound the channel, and wherein at least one of the one or more bounding parts include one or more light transmissive portions, wherein at least one of the one or more light transmissive portions is configured to receive excitation light and provide the received excitation light, and wherein excitation light enters the channel and interacts with an object resulting in emanating light; and
(c) one or more mask arrangements configured to receive at least part of the emanating light and in response, provide encoded emanating light, wherein the one or more mask arrangements and the channel are further configured so that the encoded emanating light includes time variation resulting from relative movement between the one or more mask arrangements and the object, the time variation including information about the object;

wherein the fluid-engaging structure further comprises:
at least two mirrors, wherein
a first mirror is configured to substantially reflect first excitation light from a first excitation light source through the one or more light transmissive portions, and
a second mirror is configured to substantially reflect second excitation light from a second excitation light source through the one or more light transmissive portions;
an internal reflecting surface, wherein
the internal reflecting surface is configured to re-transmit the first reflected excitation light into the channel with the fluid and objects, and
the internal reflecting surface is configured to re-transmit the second reflected excitation light into the channel with the fluid and objects, and wherein
the re-transmitted first and second excitation light interacts with the object resulting in a combined emanating light, wherein
a first of the one or more mask arrangements is located on a first portion of the bounding parts, wherein,
the first of the one or more mask arrangements is configured to receive at least part of the combined emanating light at a first range of photon energies and, in response, provide encoded combined emanating light at the first range of photon energies; and a host structure, the host structure including
the first excitation light source configured to transmit the first excitation light;
the second excitation light source configured to transmit the second excitation light;
a first photo-sensor;
a second photo-sensor;
a second of the one or more mask arrangements, and wherein
the second of the one or more mask arrangements is configured to receive at least part of the combined emanating light and, in response, provide encoded combined emanating light at a second range of photon energies;
a first filter located substantially adjacent to the first photo-sensor, wherein the first filter is configured to pass a first portion of the encoded combined emanating light that corresponds to the first range of photon energies to the first photo-sensor; and
a second filter located substantially adjacent to the second photo-sensor, wherein the second filter is configured to pass a second portion of the encoded combined emanating light that corresponds to the second range of photon energies to the second photo-sensor, and wherein, the first photo-sensor is configured to receive the filtered first portion of the encoded combined emanating light that corresponds to the first range of photon energies and detect time variation resulting from relative movement between the one or more mask arrangements and the objects, the time variation including information about the objects, and wherein the first photo-sensor is further configured to provide a first set of electrical signals indicating one or more sensed time-varying waveforms to host structure circuitry, and the second photo-sensor is configured to receive the filtered second portion of the encoded combined emanating light that corresponds to the second range of photon energies and detect time variation resulting from relative movement between the one or more mask arrangements and the objects, the time variation including information about the objects, and wherein the second photo-sensor is further configured to provide a second set of electrical signals indicating one or more sensed time-varying waveforms to host circuitry.

3. An article of manufacture, comprising:
a fluid-engaging structure, wherein the fluid-engaging structure includes
(a) a channel that in use can contain fluid and through which objects can move;
(b) one or more bounding parts that bound the channel, and wherein at least one of the one or more bounding parts include one or more light transmissive portions, wherein at least one of the one or more light transmissive portions is configured to receive excitation light and provide the received excitation light, and wherein excitation light enters the channel and interacts with an object resulting in emanating light; and
(c) one or more mask arrangements configured to receive at least part of the emanating light and in response, provide encoded emanating light, wherein the one or more mask arrangements and the channel are further configured so that the encoded emanating light includes time variation resulting from relative movement between the one or more mask arrangements and the object, the time variation including information about the object;

wherein the fluid-engaging structure comprises:
a first of the one or more mask arrangements is configured to receive at least part of the emanating light and, in response, provide color-dependent encoded emanating light and is located on a first portion of the bounding parts, and wherein
the fluid engaging structure is configured for use with a host structure, and wherein the host structure includes:
at least one excitation light source;
a filter configured to receive and filter the color-dependent encoded emanating light; and
a photo-sensor configured to receive the filtered color-dependent encoded emanating light and detect time variation resulting from relative movement between the one or more mask arrangements and the objects, the time variation including information about the objects, and wherein the photo-sensor is further configured to provide an electrical signal indicating one or more sensed time-varying waveforms.

4. An article of manufacture, comprising:
a fluid-engaging structure, wherein the fluid-engaging structure includes
  (a) a channel that in use can contain fluid and through which objects can move;
  (b) one or more bounding parts that bound the channel, and wherein at least one of the one or more bounding parts include one or more light transmissive portions, wherein at least one of the one or more light transmissive portions is configured to receive excitation light and provide the received excitation light, and wherein excitation light enters the channel and interacts with an object resulting in emanating light; and
  (c) one or more mask arrangements configured to receive at least part of the emanating light and in response, provide encoded emanating light,
wherein the one or more mask arrangements and the channel are further configured so that the encoded emanating light includes time variation resulting from relative movement between the one or more mask arrangements and the object, the time variation including information about the object;
wherein the fluid-engaging structure comprises:
  a first of the one or more mask arrangements configured to receive at least part of the emanating light and, in response, provide first color-dependent encoded emanating light and is located on a first portion of the bounding parts;
  a second of the one or more mask arrangements configured to receive at least part of the emanating light and, in response, provide second color-dependent encoded emanating light and is located on a second portion of the bounding parts, and wherein
    the fluid engaging structure is configured for use with a host structure, and wherein the host structure includes:
      a first excitation light source;
      a second excitation light source;
      a first filter configured to receive and filter the first color-dependent encoded emanating light, the first filter located substantially adjacent to the first of the one or more mask arrangements;
      a second filter configured to receive and filter the second color-dependent encoded emanating light, the second filter located substantially adjacent to the second of the one or more mask arrangements;
      a first photo-sensor located substantially adjacent to the first filter, and wherein the first photo-sensor is configured to receive the first filtered color-dependent encoded emanating light and detect time variation resulting from relative movement between the one or more mask arrangements and the objects, the time variation including information about the objects, and wherein the first photo-sensor is further configured to provide a first electrical signal indicating one or more sensed time-varying waveforms; and
      a second photo-sensor located substantially adjacent to the second filter, and wherein the second photo-sensor is configured to receive the second filtered color-dependent encoded emanating light and detect time variation resulting from relative movement between the one or more mask arrangements and the objects, the time variation including information about the objects, and wherein the second photo-sensor is further configured to provide a second electrical signal indicating one or more sensed time-varying waveforms.

5. An article of manufacture, comprising:
a host structure, wherein the host structure includes
  (a) at least one excitation light source;
  (b) one or more support parts structured to support a fluid-engaging structure on the host structure, wherein the fluid-engaging structure includes
    a channel that in use can contain fluid and through which objects can move;
    one or more bounding parts that bound the channel, and wherein at least one of the one or more bounding parts include
      one or more light transmissive portions, wherein at least one of the one or more light transmissive portions is configured to receive excitation light and provide the received excitation light, and wherein
      excitation light enters the channel and interacts with an object resulting in emanating light; and
    one or more mask arrangements configured to receive at least part of the emanating light and, in response, provide encoded emanating light, and wherein
      the one or more mask arrangements and the channel are further configured so that the encoded emanating light includes time variation resulting from relative movement between the one or more mask arrangements and the object, the time variation including information about the object;
  (c) at least one filter configured to receive and filter the encoded emanating light;
  (d) at least one photo-sensor configured to receive the filtered encoded emanating light and detect time variation resulting from relative movement between the one or more mask arrangements and the objects, the time variation including information about the objects, and wherein the photo-sensor is further configured to provide a first electrical signal indicating one or more sensed time-varying waveforms; and
  (e) circuitry configured to receive the first electrical signals and which is further configured to provide second electrical signals in response to the first electrical signals resulting from photosensing of the encoded emanating light, and wherein the second electrical signals indicate the information about the objects;
wherein the host structure further comprises:
  a first excitation light source configured to transmit first excitation light;
  a second excitation light source configured to transmit the second excitation light, and wherein
    the fluid-engaging structure is configured to provide combined emanating light resulting from interaction between the first excitation light and the objects, and the second excitation light and the objects, and wherein the fluid-engaging structure further includes
      a first of the one or more mask arrangements that is located on a first portion of the bounding parts, and wherein,
      the first of the one or more mask arrangements is configured to receive at least part of the combined emanating light at a first range of photon energies and, in response, provide encoded combined emanating light;

a first photo-sensor;

a second photo-sensor;

a second of the one or more mask arrangements, and wherein
the second of the one or more mask arrangements is configured to receive at least part of the combined emanating light and, in response, provide encoded combined emanating light at a second range of photon energies;

a first filter located substantially adjacent to the first photo-sensor, wherein the first filter is configured to pass a first portion of the encoded combined emanating light that corresponds to the first range of photon energies to the first photo-sensor; and a second filter located substantially adjacent to the second photo-sensor, wherein the second filter is configured to pass a second portion of the encoded combined emanating light that corresponds to the second range of photon energies to the second photo-sensor, and wherein the first photo-sensor is configured to receive the filtered first portion of the encoded combined emanating light that corresponds to the first range of photon energies and detect time variation resulting from relative movement between the one or more mask arrangements and the objects, the time variation including information about the objects, and wherein the first photosensor is further configured to provide a first set of electrical signals indicating one or more sensed time-varying waveforms to host structure circuitry, and the second photo-sensor is configured to receive the filtered second portion of the encoded combined emanating light that corresponds to the second range of photon energies and detect time variation resulting from relative movement between the one or more mask arrangements and the objects, the time variation including information about the objects, and wherein the second photo-sensor is further configured to provide a second set of electrical signals indicating one or more sensed time-varying waveforms to host circuitry.

* * * * *